(12) United States Patent
Shiota et al.

(10) Patent No.: US 10,597,398 B2
(45) Date of Patent: Mar. 24, 2020

(54) SUPPRESSION AND REGENERATION PROMOTING EFFECT OF LOW MOLECULAR WEIGHT COMPOUND ON CANCER AND FIBROSIS

(71) Applicants: NATIONAL UNIVERSITY CORPORATION TOTTORI UNIVERSITY, Tottori-shi (JP); KanonCure, Inc., Yonago-shi (JP)

(72) Inventors: Goshi Shiota, Yonago (JP); Noriko Itaba, Yonago (JP); Minoru Morimoto, Tottori (JP); Hiroyuki Oka, Tottori (JP); Kenichiro Abe, Yonago (JP); Hiroki Shimizu, Yonago (JP); Yohei Kouno, Yonago (JP); Satoshi Yokogi, Yonago (JP)

(73) Assignees: National University Corporation Tottori University, Tottori-shi (JP); KanonCure, Inc., Yonago-shi (JP)

( * ) Notice: Subject to any disclaimer, the term of this patent is extended or adjusted under 35 U.S.C. 154(b) by 0 days.

(21) Appl. No.: 15/760,374

(22) PCT Filed: Sep. 16, 2016

(86) PCT No.: PCT/JP2016/077475
§ 371 (c)(1),
(2) Date: Mar. 15, 2018

(87) PCT Pub. No.: WO2017/047762
PCT Pub. Date: Mar. 23, 2017

(65) Prior Publication Data
US 2019/0055249 A1 Feb. 21, 2019

(30) Foreign Application Priority Data
Sep. 18, 2015 (JP) .................. 2015-185988

(51) Int. Cl.
*A61K 31/695* (2006.01)
*C07D 487/04* (2006.01)
(Continued)

(52) U.S. Cl.
CPC .......... *C07D 487/04* (2013.01); *A61K 31/085* (2013.01); *A61K 31/513* (2013.01);
(Continued)

(58) Field of Classification Search
CPC ... C07D 487/04; C07F 7/1804; A61K 31/695; A61K 31/085; A61K 31/519; A61K 31/513; A61P 35/00
(Continued)

(56) References Cited

U.S. PATENT DOCUMENTS 3,449,418 A 6/1969 Werner
3,651,128 A 3/1972 Nikawitz
(Continued)

FOREIGN PATENT DOCUMENTS

JP S51-40142 B1 11/1976
JP 2011-518773 A 6/2011
(Continued)

OTHER PUBLICATIONS

International Search Report dated Nov. 8, 2016 for International Patent Application No. PCT/JP2016/077475, Shiota et al., "Suppression and Regeneration Promoting Effect of Low Molecular Weight Compound on Cancer and Fibrosis," filed Sep. 16, 2016 (9 pages).

(Continued)

*Primary Examiner* — Taylor V Oh
(74) *Attorney, Agent, or Firm* — Clark & Elbing LLP; Susan M. Michaud

(57) ABSTRACT

To obtain a novel therapeutic drug for a malignant tumor or fibrosis.

(Continued)

Used is a compound represented by formula (1), a salt thereof, or a solvate thereof. Also used is a therapeutic drug for a malignant tumor or a therapeutic drug for fibrosis, comprising a compound represented by formula (1), a salt thereof, or a solvate thereof.

4 Claims, 49 Drawing Sheets

(51) Int. Cl.
    *A61K 31/513* (2006.01)
    *A61K 31/519* (2006.01)
    *A61K 31/085* (2006.01)
    *A61P 35/00* (2006.01)
    *C07F 7/18* (2006.01)

(52) U.S. Cl.
    CPC .......... *A61K 31/519* (2013.01); *A61K 31/695* (2013.01); *A61P 35/00* (2018.01); *C07F 7/1804* (2013.01)

(58) Field of Classification Search
    USPC .......................................................... 514/63
    See application file for complete search history.

(56) References Cited

U.S. PATENT DOCUMENTS

| | | |
|---|---|---|
| 7,671,054 B1 | 3/2010 | Moon et al. |
| 2007/0021425 A1 | 1/2007 | Moon et al. |
| 2007/0021431 A1 | 1/2007 | Moon et al. |
| 2007/0043052 A1 | 2/2007 | Moon et al. |
| 2010/0222303 A1 | 9/2010 | Moon et al. |
| 2010/0228027 A1 | 9/2010 | Chung et al. |
| 2011/0085973 A1 | 4/2011 | Kao et al. |
| 2011/0092459 A1 | 4/2011 | Odagami et al. |
| 2013/0267482 A1 | 10/2013 | Odagami et al. |
| 2014/0112892 A1* | 4/2014 | Shiota .................. C07C 251/86 424/93.7 |
| 2018/0028536 A1 | 2/2018 | Shiota et al. |

FOREIGN PATENT DOCUMENTS

| | | |
|---|---|---|
| JP | 2011-522037 A | 7/2011 |
| WO | WO-2012/141038 A1 | 10/2012 |
| WO | WO-2015/147107 A1 | 10/2015 |

OTHER PUBLICATIONS

Noble et al., "Pirfenidone in patients with idiopathic pulmonary fibrosis (Capacity): two randomised trials," Lancet. 377(9779):1760-9 (2011).

Sakabe et al., Liver. 53(Suppl:1):A226, WS-54 (1 page) (2012).
Seto et al., Liver. 54(Suppl:1):A261, p. 12 (3 pages) (2013).

* cited by examiner

Fig. 10

| | |
|---|---|
| IC-2-Ar-Cl, MW: 517.03 | ¹H-NMR (600 MHz, CDCl₃) δ = 2.32–2.39 (m, 1H), 2.39–2.49 (m, 1H), 3.00 (dd, J = 11.5, 3.7 Hz, 1H), 3.11 (td, J = 13.2, 3.6 Hz, 1H), 3.28 (dd, J = 13.7, 5.3 Hz, 1H), 3.33 (t, J = 11.1 Hz, 1H), 3.48 (dd, J = 13.7, 5.7 Hz, 1H), 3.94 (dd, J = 14.1, 5.7 Hz, 1H), 4.16–4.26 (m, 2H), 4.31–4.42 (m, 2H), 4.73 (d, J = 14.7 Hz, 1H), 4.80 (d, J = 10.4 Hz, 1H), 5.42 (t, J = 5.6 Hz, 1H), 7.00 (t, J = 7.3 Hz, 1H), 7.10–7.21 (m, 8H), 7.29 (d, J = 8.5 Hz, 2H), 7.31–7.39 (m, 3H). ESI-HRMS m/z calcd for C₂₉H₂₉ClN₄NaO₃ [M+Na]⁺ 539.183, found 539.181. |
| IC-2-506-1, MW: 520.59 | ¹H-NMR (600 MHz, CDCl₃) δ = 2.34–2.41 (m, 1H), 2.41–2.50 (m, 1H), 3.08–3.20 (m, 2H), 3.29 (dd, J = 13.7, 5.3 Hz, 1H), 3.38–3.49 (m, 2H), 3.93 (dd, J = 14.1, 5.7 Hz, 1H), 4.25 (dd, J = 14.0, 4.7 Hz, 1H), 4.34 (br t, J = 5.0 Hz, 1H), 4.39 (dd, J = 14.1, 5.6 Hz, 1H), 4.63 (d, J = 15.4 Hz, 1H), 4.84 (d, J = 15.4 Hz, 1H), 4.97 (dd, J = 10.4, 3.4 Hz, 1H), 5.43 (t, J = 5.6 Hz, 1H), 7.04–7.11 (m, 2H), 7.14–7.19 (m, 5H), 7.21 (d, J = 7.3 Hz, 2H), 7.31–7.39 (m, 3H), 7.42 (dd, J = 7.9, 1.5 Hz, 1H). ESI-HRMS m/z calcd for C₂₉H₂₈Cl₂N₄NaO₃ [M+Na]⁺ 573.144, found 573.144. |
| IC-2-506-2, MW: 399.49 | ¹H-NMR (600 MHz, CDCl₃) δ = 2.34–2.41 (m, 1H), 2.41–2.50 (m, 1H), 3.08 (dd, J = 11.6, 3.7 Hz, 1H), 3.14 (td, J = 13.1, 3.6 Hz, 1H), 3.28 (dd, J = 13.7, 5.4 Hz, 1H), 3.40 (t, J = 11.1 Hz, 1H), 3.46 (dd, J = 13.8, 5.7 Hz, 1H), 3.93 (dd, J = 14.2, 5.7 Hz, 1H), 4.24 (dd, J = 14.3, 4.8 Hz, 1H), 4.32 (br t, 1H), 4.40 (dd, J = 14.2, 5.7 Hz, 1H), 4.56 (d, J = 15.3 Hz, 1H), 4.80 (d, J = 15.3 Hz, 1H), 4.93 (dd, J = 10.4, 3.5 Hz, 1H), 5.42 (t, J = 5.6 Hz, 1H), 7.04–7.09 (m, 1H), 7.12–7.22 (m, 8H), 7.32–7.40 (m, 4H). ESI-HRMS m/z calcd for C₂₉H₂₈Cl₂N₄NaO₃ [M+Na]⁺ 573.144, found 573.143. |
| IC-2-506-3, MW: 442.52 | ¹H-NMR (600 MHz, CDCl₃) δ = 2.33–2.40 (m, 1H), 2.40–2.49 (m, 1H), 3.01 (dd, J = 11.5, 3.8 Hz, 1H), 3.13 (td, J = 13.1, 3.6 Hz, 1H), 3.28 (dd, J = 13.7, 5.5 Hz, 1H), 3.35 (t, J = 11.1 Hz, 1H), 3.48 (dd, J = 13.8, 5.7 Hz, 1H), 3.92 (dd, J = 14.1, 5.7 Hz, 1H), 4.19–4.28 (m, 2H), 4.32–4.40 (m, 2H), 4.72 (d, J = 14.8 Hz, 1H), 4.82 (dd, J = 10.3, 3.4 Hz, 1H), 5.42 (t, J = 5.5 Hz, 1H), 6.99–7.06 (m, 2H), 7.14–7.22 (m, 6H), 7.30–7.42 (m, 5H). ESI-HRMS m/z calcd for C₂₉H₂₈Cl₂N₄NaO₃ [M+Na]⁺ 573.144, found 573.143. |
| IC-2-Ar-F, MW: 500.57 | ¹H-NMR (600 MHz, CDCl₃) δ = 2.31–2.39 (m, 1H), 2.39–2.49 (m, 1H), 3.00 (dd, J = 11.6, 3.8 Hz, 1H), 3.10 (td, J = 13.1, 3.6 Hz, 1H), 3.28 (dd, J = 13.7, 5.4 Hz, 1H), 3.32 (t, J = 11.1 Hz, 1H), 3.48 (dd, J = 13.7, 5.7 Hz, 1H), 3.95 (dd, J = 14.1, 5.7 Hz, 1H), 4.14–4.24 (m, 2H), 4.31–4.43 (m, 2H), 4.70–4.82 (m, 2H), 5.41 (t, J = 5.6 Hz, 1H), 6.97–7.03 (m, 3H), 7.11–7.21 (m, 8H), 7.31–7.38 (m, 3H). ESI-HRMS m/z calcd for C₂₉H₂₉FN₄NaO₃ [M+Na]⁺ 523.212, found 523.211. |

Fig. 11

| | |
|---|---|
| IC-2-Ar-OMe, MW: 512.61 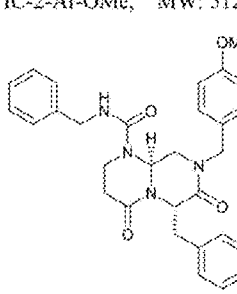 | ¹H-NMR (600 MHz, CDCl₃) δ = 2.30–2.37 (m, 1H), 2.37–2.47 (m, 1H), 3.00 (dd, $J$ = 11.6, 3.7 Hz, 1H), 3.08 (td, $J$ = 13.1, 3.5 Hz, 1H), 3.24–3.34 (m, 2H), 3.49 (dd, $J$ = 13.8, 5.6 Hz, 1H), 3.80 (s, 3H), 3.97 (dd, $J$ = 14.1, 5.7 Hz, 1H), 4.12–4.23 (m, 2H), 4.32 (dd, $J$ = 14.4, 5.7 Hz, 1H), 4.38 (d, $J$ = 14.4 Hz, 1H), 4.65–4.76 (m, 2H), 5.39 (t, $J$ = 5.5 Hz, 1H), 6.85 (d, $J$ = 8.7 Hz, 2H), 6.95 (t, $J$ = 7.4 Hz, 1H), 7.09–7.16 (m, 6H), 7.19 (d, $J$ = 8.0 Hz, 2H), 7.30–7.38 (m, 3H). ESI-HRMS m/z calcd for $C_{30}H_{32}N_4NaO_4$ [M+Na]⁺ 535.232, found 535.231. |
| IC-2-Ar-NO₂, MW: 527.58 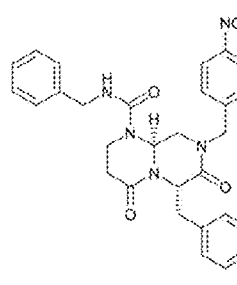 | ¹H-NMR (600 MHz, CDCl₃) δ = 2.34–2.41 (m, 1H), 2.41–2.50 (m, 1H), 3.08 (dd, $J$ = 11.4, 3.7 Hz, 1H), 3.17 (td, $J$ = 12.9, 3.7 Hz, 1H), 3.31 (dd, $J$ = 13.7, 5.3 Hz, 1H), 3.40 (t, $J$ = 11.1 Hz, 1H), 3.45 (dd, $J$ = 13.8, 6.1 Hz, 1H), 3.86 (dd, $J$ = 7.0, 5.6 Hz, 1H), 4.23 (dd, $J$ = 16.2, 6.7 Hz, 1H), 4.34–4.44 (m, 2H), 4.53 (d, $J$ = 15.3 Hz, 1H), 4.83 (d, $J$ = 15.3 Hz, 1H), 5.03 (dd, $J$ = 10.3, 3.5 Hz, 1H), 5.47 (t, $J$ = 5.7 Hz, 1H), 7.08–7.14 (m, 1H), 7.16–7.22 (m, 6H), 7.30–7.38 (m, 5H), 8.17 (d, $J$ = 8.9 Hz, 2H). ESI-HRMS m/z calcd for $C_{29}H_{29}N_5NaO_5$ [M+Na]⁺ 550.207, found 550.206. |
| IC-2-Ar-OH, MW: 498.58 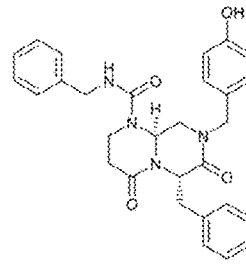 | ¹H-NMR (600 MHz, CDCl₃) δ = 2.24–2.33 (m, 1H), 2.33–2.43 (m, 1H), 2.99–3.12 (m, 2H), 3.23–3.34 (m, 2H), 3.42 (dd, $J$ = 13.8, 6.1 Hz, 1H), 3.87 (dd, $J$ = 13.9, 5.6 Hz, 1H), 4.22 (dd, $J$ = 14.5, 5.0 Hz, 1H), 4.34 (dd, $J$ = 14.5, 5.7 Hz, 1H), 4.43 (d, $J$ = 14.4 Hz, 1H), 4.47 (br t, 1H), 4.54 (d, $J$ = 14.4 Hz, 1H), 4.90 (dd, $J$ = 10.1, 3.2 Hz, 1H), 5.39 (t, $J$ = 5.7 Hz, 1H), 6.75 (d, $J$ = 8.6 Hz, 2H), 6.95–7.01 (m, 2H), 7.03 (d, $J$ = 8.5 Hz, 2H), 7.11 (t, $J$ = 7.6 Hz, 2H), 7.14–7.19 (m, 4H), 7.28–7.37 (m, 3H). ESI-HRMS m/z calcd for $C_{29}H_{30}N_4NaO_4$ [M+Na]⁺ 521.216, found 521.215. |
| IC-2-OTBS, MW: 662.91 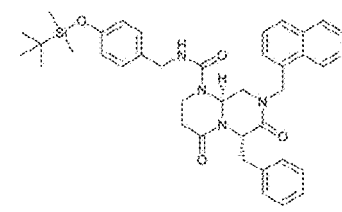 | ¹H-NMR (600 MHz, CDCl₃) δ = 0.22 (s, 6H), 1.01 (s, 9H), 2.25–2.33 (m, 1H), 2.35–2.44 (m, 1H), 2.91–3.02 (m, 2H), 3.13 (t, $J$ = 11.2 Hz, 1H), 3.31 (dd, $J$ = 13.7, 5.6 Hz, 1H), 3.55 (dd, $J$ = 13.7, 5.2 Hz, 1H), 3.85–3.98 (m, 2H), 4.07 (dd, $J$ = 14.2, 4.8 Hz, 1H), 4.13 (dd, $J$ = 14.2, 5.7 Hz, 1H), 4.63 (d, $J$ = 10.2 Hz, 1H), 5.04 (d, $J$ = 14.6 Hz, 1H), 5.17 (d, $J$ = 14.7 Hz, 1H), 5.43 (t, $J$ = 5.4 Hz, 1H), 6.77 (d, $J$ = 8.5 Hz, 2H), 6.88–6.94 (m, 3H), 7.05 (t, $J$ = 7.7 Hz, 2H), 7.20 (d, $J$ = 7.0 Hz, 1H), 7.26 (d, $J$ = 7.0 Hz, 1H), 7.39 (t, $J$ = 7.6 Hz, 1H), 7.55 (t, $J$ = 7.4 Hz, 1H), 7.59 (t, $J$ = 7.6 Hz, 1H), 7.85 (d, $J$ = 8.2 Hz, 1H), 7.90 (d, $J$ = 8.1 Hz, 1H), 8.12 (d, $J$ = 8.2 Hz, 1H). ESI-HRMS m/z calcd for $C_{39}H_{46}N_4NaO_4Si$ [M+Na]⁺ 685.319, found 685.317. |
| 7c-NT, MW: 520.59 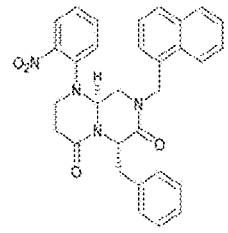 | ¹H-NMR (600 MHz, CDCl₃) δ = 2.33–2.48 (m, 2H), 2.94 (dd, $J$ = 12.3, 3.5 Hz, 1H), 3.00–3.10 (m, 1H), 3.20–3.28 (m, 1H), 3.28–3.37 (m, 1H), 3.43 (dd, $J$ = 14.1, 5.9 Hz, 1H), 3.66 (dd, $J$ = 14.1, 5.1 Hz, 1H), 4.24 (dd, $J$ = 10.3, 3.5 Hz, 1H), 4.87 (d, $J$ = 14.7 Hz, 1H), 5.31 (d, $J$ = 14.7 Hz, 1H), 5.59 (t, $J$ = 5.5 Hz, 1H), 6.33 (dd, $J$ = 7.9, 1.4 Hz, 1H), 7.10–7.19 (m, 2H), 7.20–7.34 (m, 6H), 7.38 (t, $J$ = 7.6 Hz, 1H), 7.51–7.61 (m, 3H), 7.81 (d, $J$ = 8.3 Hz, 1H), 7.87 (d, $J$ = 8.1 Hz, 1H), 8.12 (d, $J$ = 8.3 Hz, 1H). ESI-HRMS m/z calcd for $C_{31}H_{28}N_4NaO_4$ [M+Na]⁺ 543.201, found 543.201. |

Fig. 12

| 9b,   MW: 399.49 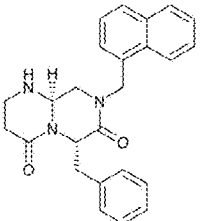 | ¹H-NMR (600 MHz, CDCl₃) $\delta$ = 1.14 (br s, 1H), 2.27–2.42 (m, 2H), 2.64–2.75 (m, 1H), 2.85–2.99 (m, 3H), 3.33–3.43 (m, 2H), 3.62 (dd, $J$ = 13.5, 3.5 Hz, 1H), 4.86 (d, $J$ = 14.8 Hz, 1H), 5.32–5.39 (m, 2H), 7.15–7.21 (m, 5H), 7.23 (d, $J$ = 6.9 Hz, 1H), 7.38 (t, $J$ = 7.6 Hz, 1H), 7.55 (td, $J$ = 7.5, 1.1 Hz, 1H), 7.60 (td, $J$ = 7.6, 1.4 Hz, 1H), 7.82 (d, $J$ = 8.2 Hz, 1H), 7.88 (d, $J$ = 8.1 Hz, 1H), 8.14 (d, $J$ = 8.4 Hz, 1H). <br> ESI-HRMS $m/z$ calcd for $C_{25}H_{25}N_3NaO_2$ [M+Na]⁺ 422.184, found 422.183. |
|---|---|
| 9b-CONH₂,   MW: 442.52 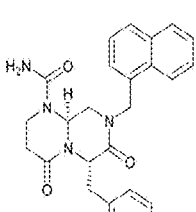 | ¹H-NMR (600 MHz, CDCl₃) $\delta$ = 2.26–2.34 (m, 1H), 2.35–2.46 (m, 1H), 2.93–3.05 (m, 2H), 3.10 (t, $J$ = 11.2 Hz, 1H), 3.33 (dd, $J$ = 13.7, 5.5 Hz, 1H), 3.55 (dd, $J$ = 13.7, 5.5 Hz, 1H), 3.84 (dd, $J$ = 13.8, 5.4 Hz, 1H), 4.18 (s, 2H), 4.76 (br s, 1H), 5.02 (d, $J$ = 14.7 Hz, 1H), 5.21 (d, $J$ = 14.7 Hz, 1H), 5.43 (t, $J$ = 5.5 Hz, 1H), 7.19–7.30 (m, 6H), 7.40 (t, $J$ = 7.5 Hz, 1H), 7.51–7.61 (m, 2H), 7.84 (d, $J$ = 8.3 Hz, 1H), 7.88 (d, $J$ = 8.1 Hz, 1H), 8.09 (d, $J$ = 8.3 Hz, 1H). <br> ESI-HRMS $m/z$ calcd for $C_{26}H_{27}N_4O_3$ [M+H]⁺ 443.208, found 443.207. |

Fig. 13

| IC-2-Cl, MW: 567.09 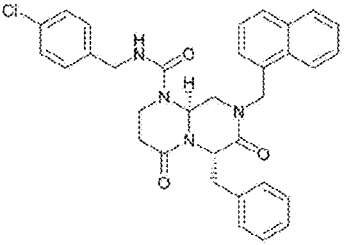 | $^1$H-NMR (600 MHz, CDCl$_3$) δ = 2.26–2.34 (m, 1H), 2.34–2.44 (m, 1H), 2.91 (dd, $J$ = 11.8, 3.7 Hz, 1H), 2.98 (td, $J$ = 13.1, 3.5 Hz, 1H), 3.15 (t, $J$ = 11.2 Hz, 1H), 3.31 (dd, $J$ = 13.7, 5.6 Hz, 1H), 3.57 (dd, $J$ = 13.6, 5.1 Hz, 1H), 3.92 (dd, $J$ = 14.0, 5.9 Hz, 1H), 3.97 (br t, 1H), 4.05 (dd, $J$ = 14.7, 5.1 Hz, 1H), 4.17 (dd, $J$ = 14.7, 5.9 Hz, 1H), 4.60 (d, $J$ = 10.3 Hz, 1H), 4.98 (d, $J$ = 14.6 Hz, 1H), 5.23 (d, $J$ = 14.6 Hz, 1H), 5.43 (t, $J$ = 5.3 Hz, 1H), 6.96 (d, $J$ = 8.4 Hz, 2H), 7.00 (t, $J$ = 7.3 Hz, 1H), 7.09 (t, $J$ = 7.6 Hz, 2H), 7.21 (d, $J$ = 7.6 Hz, 2H), 7.24–7.27 (m, 3H), 7.38 (t, $J$ = 7.6 Hz, 1H), 7.55 (t, $J$ = 7.4 Hz, 2H), 7.59 (t, $J$ = 7.5 Hz, 2H), 7.84 (d, $J$ = 8.3 Hz, 1H), 7.90 (d, $J$ = 8.0 Hz, 1H), 8.10 (d, $J$ = 8.3 Hz, 1H). ESI-HRMS m/z calcd for C$_{33}$H$_{31}$ClN$_4$NaO$_3$ [M+Na]$^+$ 589.198, found 589.197. |
| --- | --- |
| IC-2-F, MW: 550.63 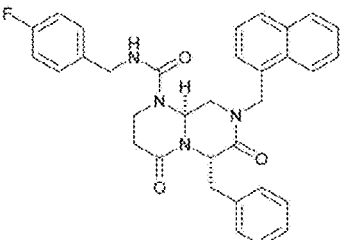 | $^1$H-NMR (600 MHz, CDCl$_3$) δ = 2.26–2.39 (m, 1H), 2.35–2.45 (m, 1H), 2.93 (dd, $J$ = 11.8, 3.6 Hz, 1H), 2.98 (td, $J$ = 13.2, 3.5 Hz, 1H), 3.14 (t, $J$ = 11.2 Hz, 1H), 3.31 (dd, $J$ = 13.7, 5.6 Hz, 1H), 3.56 (dd, $J$ = 13.7, 5.2 Hz, 1H), 3.91 (dd, $J$ = 14.0, 5.8 Hz, 1H), 3.99 (br t, 1H), 4.07 (dd, $J$ = 14.6, 5.0 Hz, 1H), 4.17 (dd, $J$ = 14.5, 5.9 Hz, 1H), 4.62 (d, $J$ = 10.3 Hz, 1H), 4.99 (d, $J$ = 14.7 Hz, 1H), 5.22 (d, $J$ = 14.7 Hz, 1H), 5.43 (t, $J$ = 5.4 Hz, 1H), 6.95–7.03 (m, 5H), 7.08 (t, $J$ = 7.6 Hz, 2H), 7.21 (d, $J$ = 7.5 Hz, 2H), 7.26 (d, $J$ = 6.6 Hz, 1H), 7.38 (t, $J$ = 7.6 Hz, 1H), 7.55 (t, $J$ = 7.4 Hz, 2H), 7.59 (t, $J$ = 7.5 Hz, 2H), 7.84 (d, $J$ = 8.3 Hz, 1H), 7.90 (d, $J$ = 8.0 Hz, 1H), 8.11 (d, $J$ = 8.2 Hz, 1H). ESI-HRMS m/z calcd for C$_{33}$H$_{31}$FN$_4$NaO$_3$ [M+Na]$^+$ 573.228, found 573.226. |
| IC-2-OMe, MW: 562.67 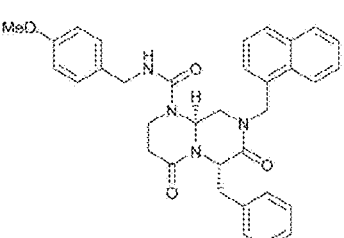 | $^1$H-NMR (600 MHz, CDCl$_3$) δ = 2.24–2.32 (m, 1H), 2.34–2.43 (m, 1H), 2.92–3.01 (m, 2H), 3.13 (t, $J$ = 11.2 Hz, 1H), 3.31 (dd, $J$ = 13.6, 5.6 Hz, 1H), 3.54 (dd, $J$ = 13.7, 5.4 Hz, 1H), 3.82 (s, 3H), 3.88 (dd, $J$ = 14.0, 5.7 Hz, 1H), 3.97 (br t, 1H), 4.07 (dd, $J$ = 14.2, 4.8 Hz, 1H), 4.15 (dd, $J$ = 14.3, 5.7 Hz, 1H), 4.67 (d, $J$ = 10.4 Hz, 1H), 5.05 (d, $J$ = 14.7 Hz, 1H), 5.15 (d, $J$ = 14.6 Hz, 1H), 5.43 (t, $J$ = 5.5 Hz, 1H), 6.83 (d, $J$ = 8.7 Hz, 2H), 6.96 (t, $J$ = 7.4 Hz, 1H), 6.98 (d, $J$ = 8.7 Hz, 2H), 7.08 (t, $J$ = 7.7 Hz, 2H), 7.21 (d, $J$ = 7.7 Hz, 2H), 7.25 (d, $J$ = 7.3 Hz, 1H), 7.38 (t, $J$ = 8.2 Hz, 1H), 7.55 (t, $J$ = 7.4 Hz, 1H), 7.59 (t, $J$ = 7.6 Hz, 1H), 7.84 (d, $J$ = 8.2 Hz, 1H), 7.90 (d, $J$ = 8.0 Hz, 1H), 8.11 (d, $J$ = 8.3 Hz, 1H). ESI-HRMS m/z calcd for C$_{34}$H$_{34}$N$_4$NaO$_4$ [M+Na]$^+$ 585.248, found 585.246. |
| IC-2-NO2, MW: 577.64 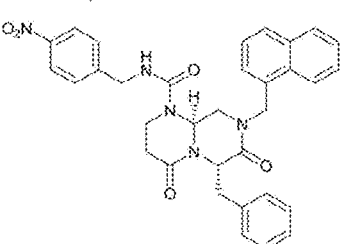 | $^1$H-NMR (600 MHz, CDCl$_3$) δ = 2.30–2.38 (m, 1H), 2.38–2.49 (m, 1H), 2.91 (dd, $J$ = 11.8, 3.7 Hz, 1H), 3.02 (td, $J$ = 13.1, 3.5 Hz, 1H), 3.19 (t, $J$ = 11.2 Hz, 1H), 3.31 (dd, $J$ = 13.7, 5.7 Hz, 1H), 3.60 (dd, $J$ = 13.7, 4.9 Hz, 1H), 3.97 (dd, $J$ = 14.0, 5.8 Hz, 1H), 4.06–4.18 (m, 2H), 4.32 (dd, $J$ = 16.9, 7.5 Hz, 1H), 4.58 (d, $J$ = 10.0 Hz, 1H), 4.91 (d, $J$ = 14.7 Hz, 1H), 5.33 (d, $J$ = 14.7 Hz, 1H), 5.45 (t, $J$ = 5.3 Hz, 1H), 7.05 (t, $J$ = 7.4 Hz, 1H), 7.09–7.15 (m, 4H), 7.24 (d, $J$ = 7.5 Hz, 2H), 7.28 (d, $J$ = 7.0 Hz, 2H), 7.40 (t, $J$ = 7.6 Hz, 1H), 7.55 (t, $J$ = 7.5 Hz, 1H), 7.59 (t, $J$ = 7.6 Hz, 1H), 7.85 (d, $J$ = 8.3 Hz, 1H), 7.89 (d, $J$ = 8.0 Hz, 1H), 8.08–8.14 (m, 3H). ESI-HRMS m/z calcd for C$_{33}$H$_{31}$N$_5$NaO$_5$ [M+Na]$^+$ 600.222, found 600.221. |
| IC-2-OMOM, MW: 592.70 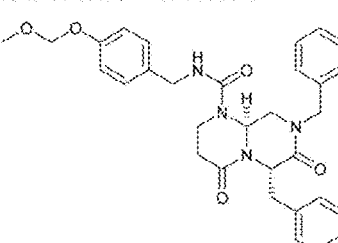 | $^1$H-NMR (600 MHz, CDCl$_3$) δ = 2.24–2.32 (m, 1H), 2.33–2.43 (m, 1H), 2.91–3.02 (m, 2H), 3.13 (t, $J$ = 11.2 Hz, 1H), 3.31 (dd, $J$ = 13.7, 5.6 Hz, 1H), 3.50 (s, 3H), 3.54 (dd, $J$ = 13.7, 5.3 Hz, 1H), 3.89 (dd, $J$ = 14.0, 5.9 Hz, 1H), 3.97 (br t, 1H), 4.06 (dd, $J$ = 14.2, 4.8 Hz, 1H), 4.16 (dd, $J$ = 14.2, 5.7 Hz, 1H), 4.66 (d, $J$ = 10.4 Hz, 1H), 5.03 (d, $J$ = 14.6 Hz, 1H), 5.17 (d, $J$ = 14.7 Hz, 1H), 5.19 (s, 2H) 5.43 (t, $J$ = 5.4 Hz, 1H), 6.92–6.99 (m, 5H), 7.07 (t, $J$ = 7.6 Hz, 2H), 7.20 (d, $J$ = 6.9 Hz, 2H), 7.26 (d, $J$ = 6.5 Hz, 1H), 7.39 (t, $J$ = 7.6 Hz, 1H), 7.55 (t, $J$ = 7.4 Hz, 1H), 7.58 (t, $J$ = 7.5 Hz, 1H), 7.85 (d, $J$ = 8.2 Hz, 1H), 7.90 (d, $J$ = 8.0 Hz, 1H), 8.11 (d, $J$ = 8.4 Hz, 1H). ESI-HRMS m/z calcd for C$_{35}$H$_{37}$N$_4$O$_5$ [M+H]$^+$ 593.276, found 593.275. |

Fig. 14

| | |
|---|---|
| IC-2-OPMB, MW: 668.79 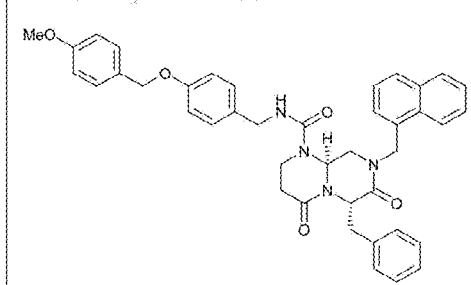 | $^1$H-NMR (600 MHz, CDCl$_3$) $\delta$ = 2.24–2.31 (m, 1H), 2.32–2.43 (m, 1H), 2.90–3.01 (m, 2H), 3.12 (t, $J$= 11.2 Hz, 1H), 3.31 (dd, $J$= 13.7, 5.6 Hz, 1H), 3.53 (dd, $J$= 13.6, 5.4 Hz, 1H), 3.80 (s, 3H), 3.87 (dd, $J$= 14.0, 5.8 Hz, 1H), 3.98 (br t, 1H), 4.07 (dd, $J$= 14.2, 4.9 Hz, 1H), 4.14 (dd, $J$= 14.2, 5.7 Hz, 1H), 4.67 (d, $J$= 10.4 Hz, 1H), 5.00 (s, 2H), 5.04 (d, $J$= 14.7 Hz, 1H), 5.15 (d, $J$= 14.7 Hz, 1H), 5.42 (t, $J$= 5.4 Hz, 1H), 6.87–6.96 (m, 5H), 6.97 (d, $J$= 8.6 Hz, 2H), 7.06 (t, $J$= 7.6 Hz, 2H), 7.20 (d, $J$= 7.7 Hz, 2H), 7.24 (d, $J$= 7.0 Hz, 1H), 7.34–7.40 (m, 3H), 7.54 (t, $J$= 7.4 Hz, 1H), 7.57 (t, $J$= 7.6 Hz, 1H), 7.83 (d, $J$= 8.2 Hz, 1H), 7.88 (d, $J$= 8.0 Hz, 1H), 8.10 (d, $J$= 8.3 Hz, 1H). ESI-HRMS $m/z$ calcd for C$_{41}$H$_{40}$N$_4$NaO$_5$ [M+Na]$^+$ 691.290, found 691.289. |
| IC-2-MOTBS, MW: 676.93 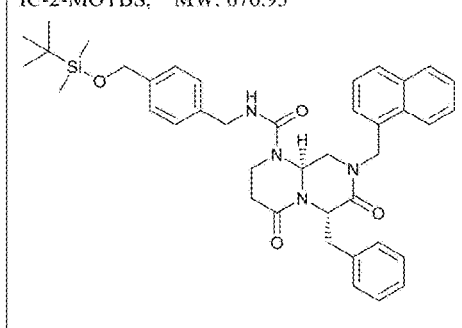 | $^1$H-NMR (600 MHz, CDCl$_3$) $\delta$ = 0.12 (s, 6H), 0.96 (s, 9H), 2.23–2.32 (m, 1H), 2.33–2.45 (m, 1H), 2.91–3.04 (m, 2H), 3.13 (t, $J$ = 11.2 Hz, 1H), 3.31 (dd, $J$ = 13.6, 5.5 Hz, 1H), 3.54 (dd, $J$ = 13.7, 5.4 Hz, 1H), 3.88 (dd, $J$ = 13.9, 5.7 Hz, 1H), 4.01 (br t, 1H), 4.12 (dd, $J$ = 14.4, 4.9 Hz, 1H), 4.21 (dd, $J$ = 14.4, 5.7 Hz, 1H), 4.70 (d, $J$ = 10.4 Hz, 1H), 4.75 (s, 2H), 5.08 (d, $J$ = 14.6 Hz, 1H), 5.14 (d, $J$ = 14.7 Hz, 1H), 5.43 (t, $J$ = 5.4 Hz, 1H), 6.96 (t, $J$ = 7.4 Hz, 1H), 7.03 (d, $J$ = 8.0 Hz, 2H), 7.08 (t, $J$ = 7.7 Hz, 2H), 7.21 (d, $J$ = 7.5 Hz, 2H), 7.23–7.30 (m, 3H), 7.38 (t, $J$ = 7.6 Hz, 1H), 7.54 (t, $J$ = 7.4 Hz, 1H), 7.58 (t, $J$ = 7.6 Hz, 1H), 7.84 (d, $J$ = 8.2 Hz, 1H), 7.89 (d, $J$ = 8.0 Hz, 1H), 8.10 (d, $J$ = 8.3 Hz, 1H). ESI-HRMS $m/z$ calcd for C$_{40}$H$_{48}$N$_4$NaO$_4$Si [M+Na]$^+$ 699.334, found 699.333. |
| IC-2-OH, MW: 548.64 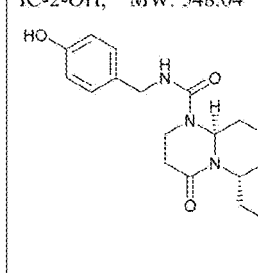 | $^1$H-NMR (600 MHz, DMSO-$d_6$) $\delta$ = 2.00–2.07 (m, 2H), 3.09–3.18 (m, 2H), 3.19–3.29 (m, 2H), 3.58 (t, $J$ = 11.2 Hz, 1H), 3.84 (d, $J$ = 13.7, 1H), 4.07 (dd, $J$ = 14.9, 5.4 Hz, 1H), 4.20 (dd, $J$ = 14.9, 5.9 Hz, 1H), 4.92 (d, $J$ = 15.0 Hz, 1H), 5.15 (d, $J$ = 15.0 Hz, 1H), 5.22 (dd, $J$ = 9.3, 4.7 Hz, 1H), 5.78 (dd, $J$ = 10.7, 4.1 Hz, 1H), 6.70 (d, $J$= 8.6 Hz, 2H), 7.34 (d, $J$ = 8.5 Hz, 2H), 7.11–7.20 (m, 5H), 7.41 (d, $J$ = 6.9 Hz, 1H), 7.45–7.53 (m, 2H), 7.54–7.62 (m, 2H), 7.91 (d, $J$ = 8.3 Hz, 1H), 7.98 (d, $J$ = 7.9 Hz, 1H), 8.16 (d, $J$ = 8.1 Hz, 1H), 9.31 (s, 1H). ESI-HRMS $m/z$ calcd for C$_{33}$H$_{32}$N$_4$NaO$_4$ [M+Na]$^+$ 571.232, found 571.231. |
| IC-2-MOH, MW: 562.67 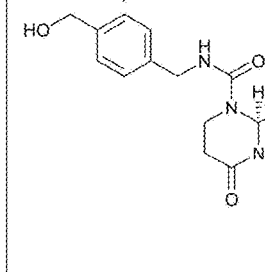 | $^1$H-NMR (600 MHz, CDCl$_3$) $\delta$ = 2.08 (br s, 1H), 2.17–2.24 (m, 1H), 2.24–2.34 (m, 1H), 2.89–3.01 (m, 2H), 3.11 (t, $J$ = 11.2 Hz, 1H), 3.30 (dd, $J$ = 13.7, 5.4 Hz, 1H), 3.48 (dd, $J$ = 13.7, 5.7 Hz, 1H), 3.82 (dd, $J$ = 14.0, 5.7 Hz, 1H), 4.12 (dd, $J$ = 14.5, 5.1 Hz, 1H), 4.23 (dd, $J$ = 14.5, 5.7 Hz, 1H), 4.30 (br t, 1H), 4.68 (s, 2H), 4.81 (d, $J$ = 10.2 Hz, 1H), 5.04–5.13 (m, 2H), 5.39 (t, $J$ = 5.7 Hz, 1H), 7.01 (t, $J$ = 7.4 Hz, 1H), 7.06 (d, $J$= 8.1 Hz, 2H), 7.10 (t, $J$ = 7.6 Hz, 2H), 7.20 (d, $J$ = 7.5 Hz, 2H), 7.25 (d, $J$ = 7.1 Hz, 1H), 7.29 (d, $J$ = 8.0 Hz, 2H), 7.38 (t, $J$ = 7.6 Hz, 1H), 7.53 (t, $J$ = 7.4 Hz, 1H), 7.57 (t, $J$ = 7.5 Hz, 1H), 7.83 (d, $J$ = 8.2 Hz, 1H), 7.88 (d, $J$ = 8.0 Hz, 1H), 8.08 (d, $J$ = 8.3 Hz, 1H). ESI-HRMS $m/z$ calcd for C$_{34}$H$_{34}$N$_4$NaO$_4$ [M+Na]$^+$ 585.248, found 585.247. |

Fig. 15
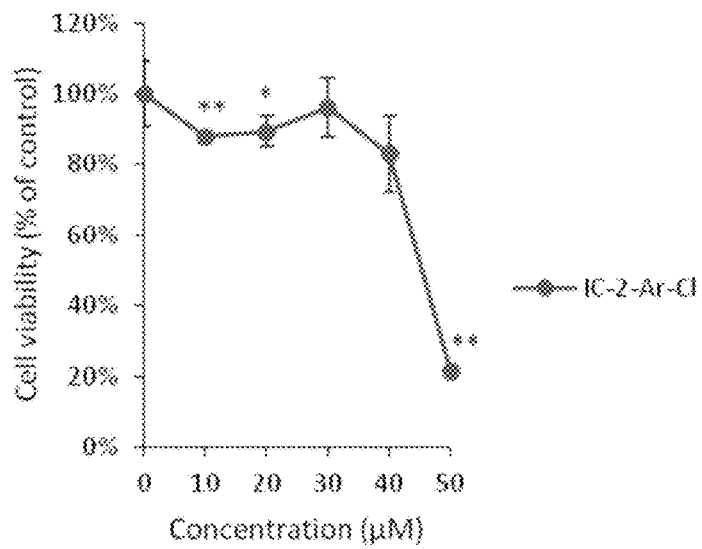
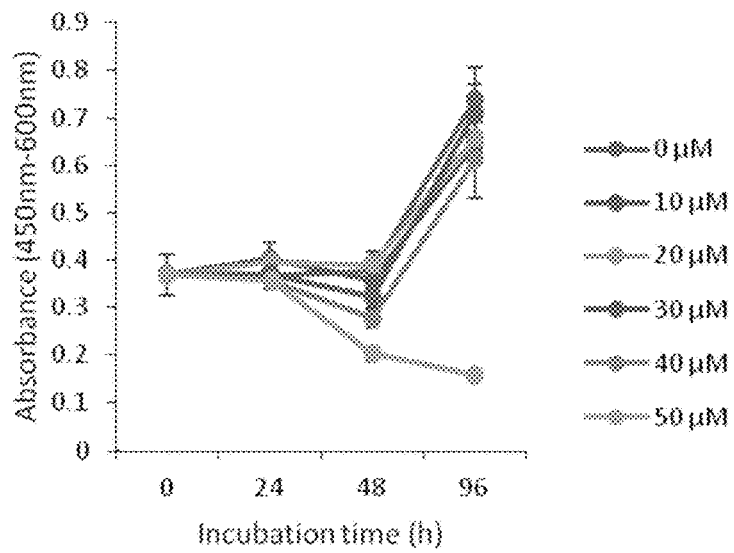

Fig. 16
Growth Inhibition Rate After 96 h (HuH-7 Cells)
IC-2-506-1
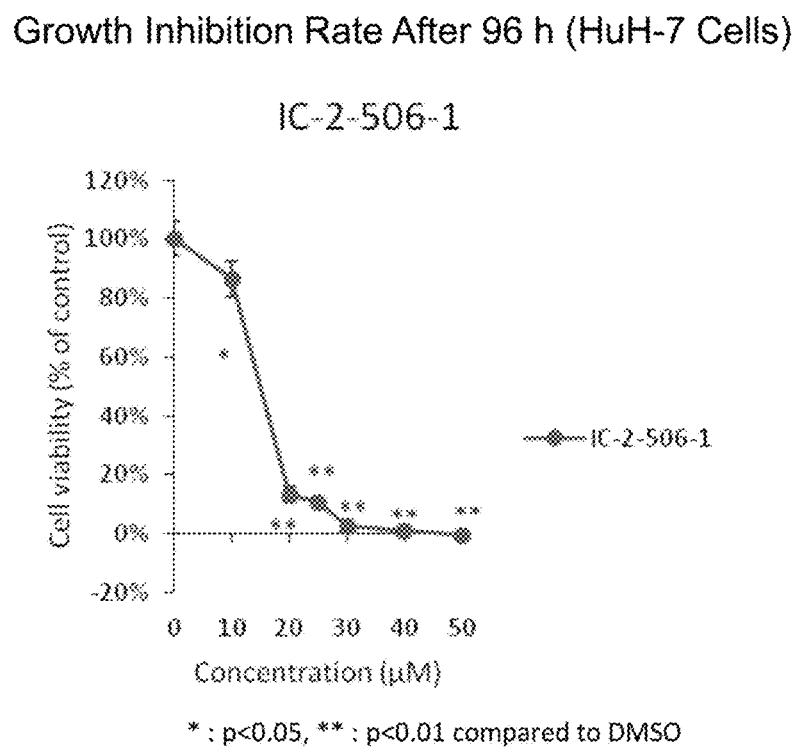
*: p<0.05, **: p<0.01 compared to DMSO
Treatment Time and Cell Viability Curve (HuH-7 Cells)
IC-2-506-1
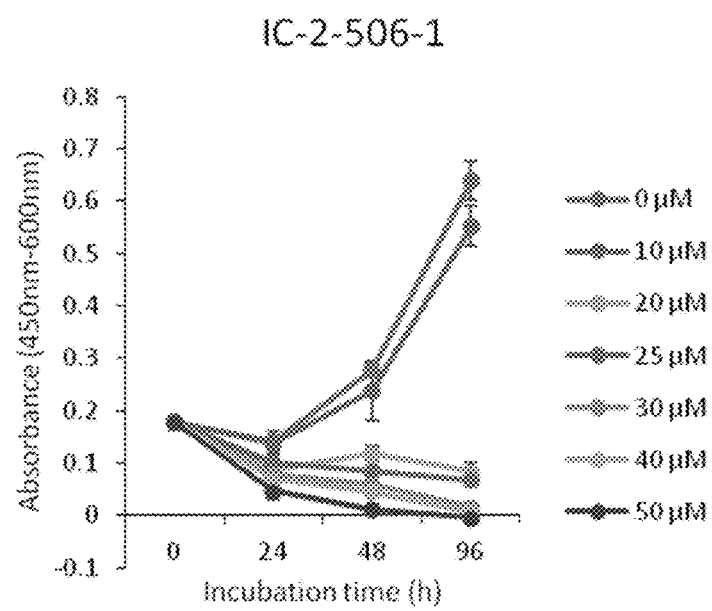

Fig. 17
Growth Inhibition Rate After 96 h (HuH-7 Cells)
IC-2-506-2
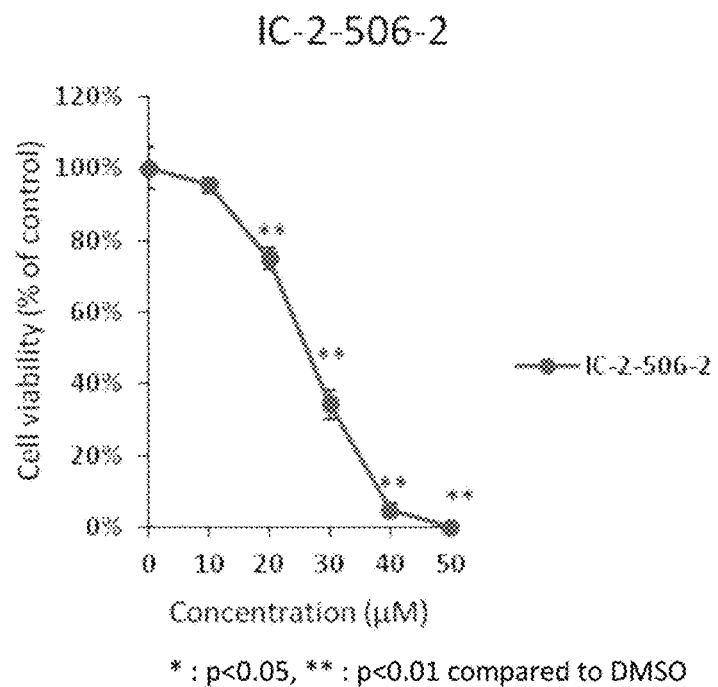
*: p<0.05, **: p<0.01 compared to DMSO
Treatment Time and Cell Viability Curve (HuH-7 Cells)
IC-2-506-2
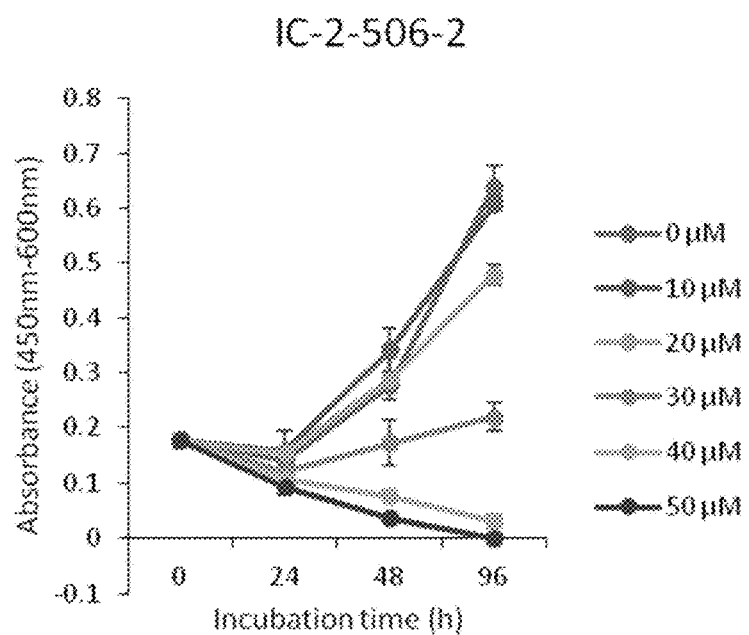

Fig. 18
Growth Inhibition Rate After 96 h (HuH-7 Cells)
IC-2-506-3
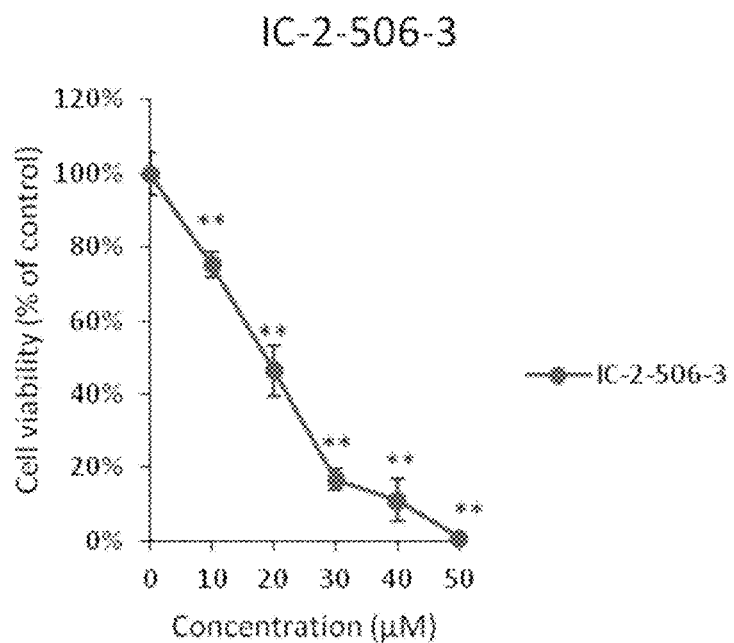
*: p<0.05, **: p<0.01 compared to DMSO
Treatment Time and Cell Viability Curve (HuH-7 Cells)
IC-2-506-3
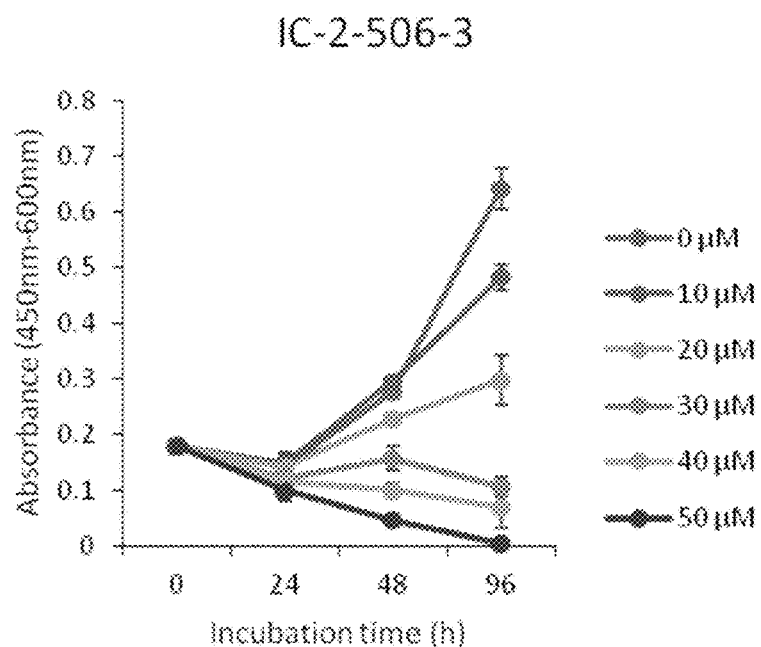

Fig. 19
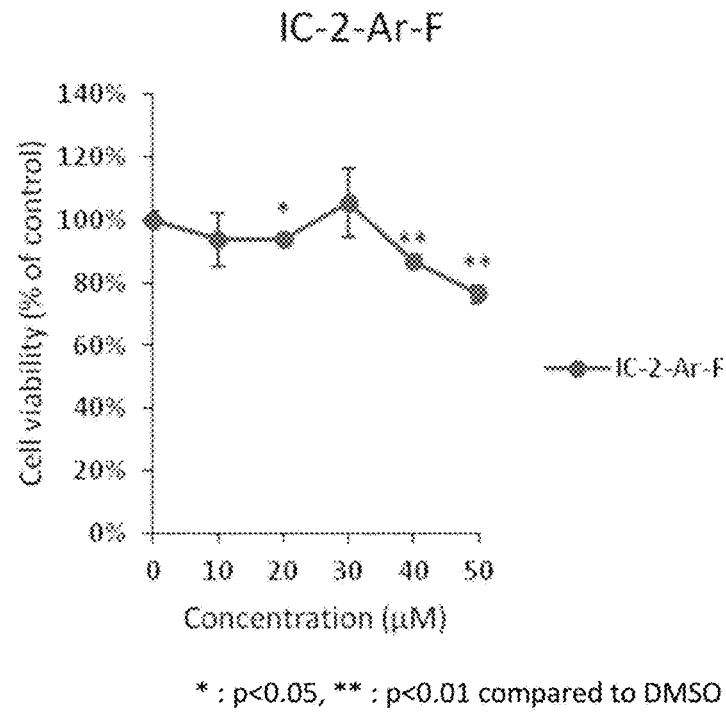
Growth Inhibition Rate After 96 h (HuH-7 Cells)
IC-2-Ar-F
*: p<0.05, **: p<0.01 compared to DMSO
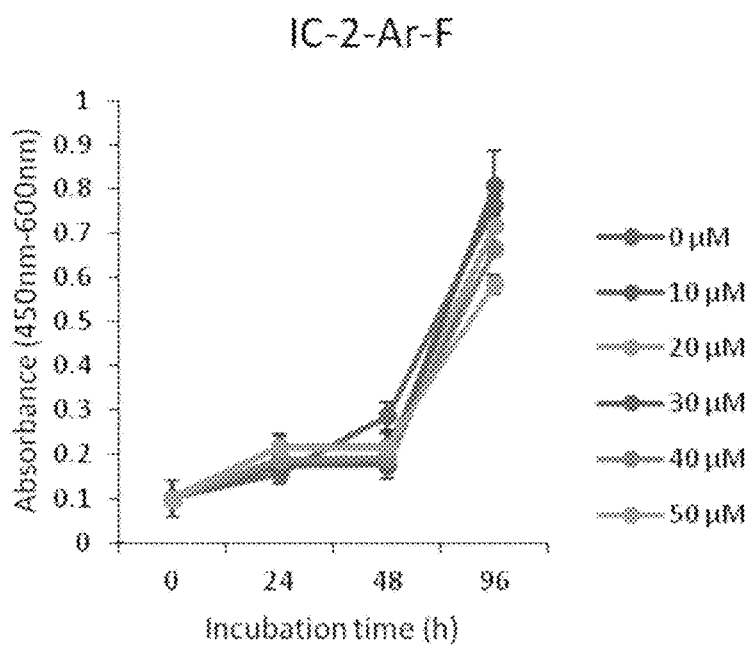
Treatment Time and Cell Viability Curve (HuH-7 Cells)
IC-2-Ar-F Fig. 20
Growth Inhibition Rate After 96 h (HuH-7 Cells)
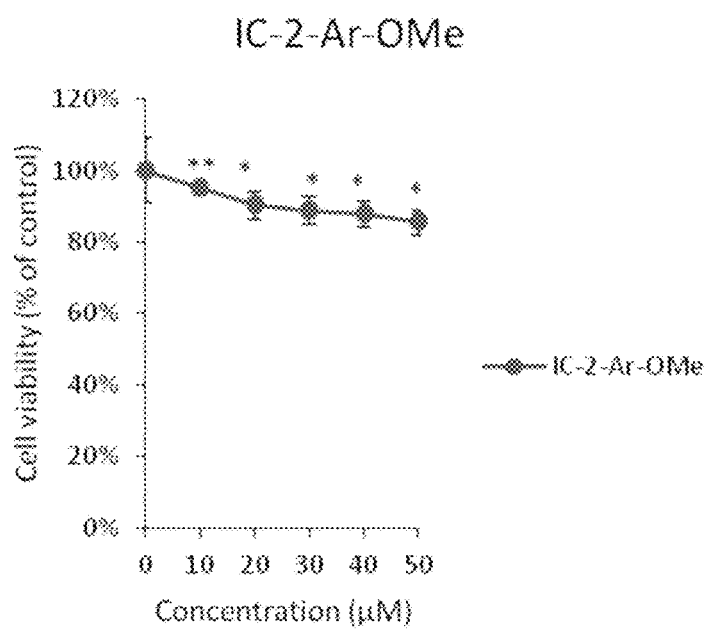
*: p<0.05, **: p<0.01 compared to DMSO
Treatment Time and Cell Viability Curve (HuH-7 Cells)
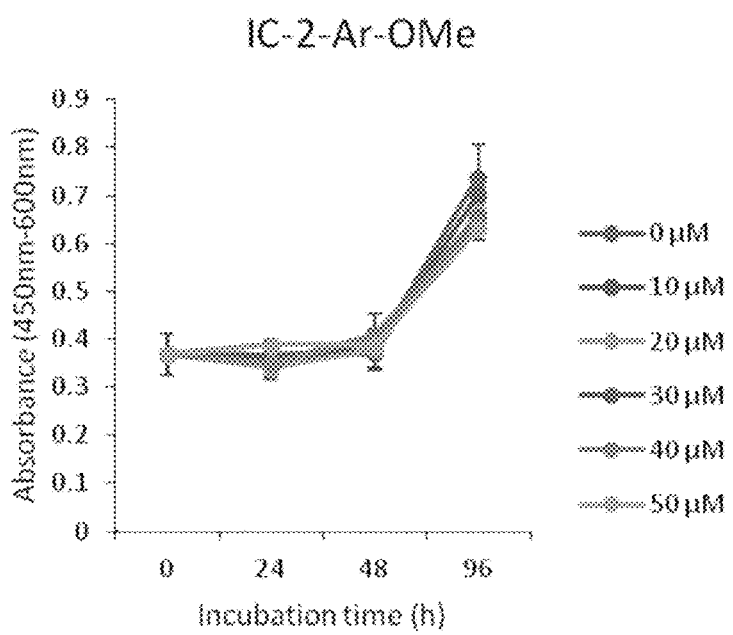

Fig. 21
Growth Inhibition Rate After 96 h (HuH-7 Cells)
IC-2-Ar-NO2
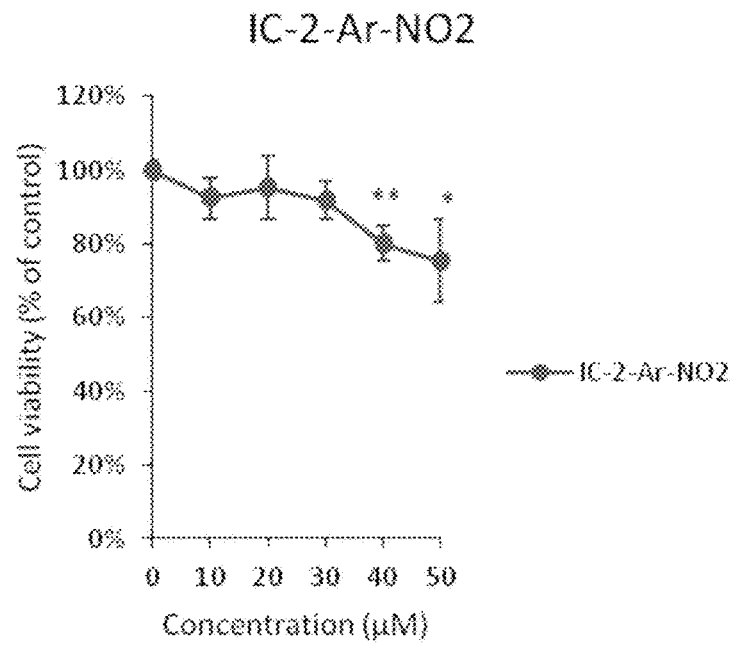
*: $p<0.05$, **: $p<0.01$ compared to DMSO
Treatment Time and Cell Viability Curve (HuH-7 Cells)
IC-2-Ar-NO2
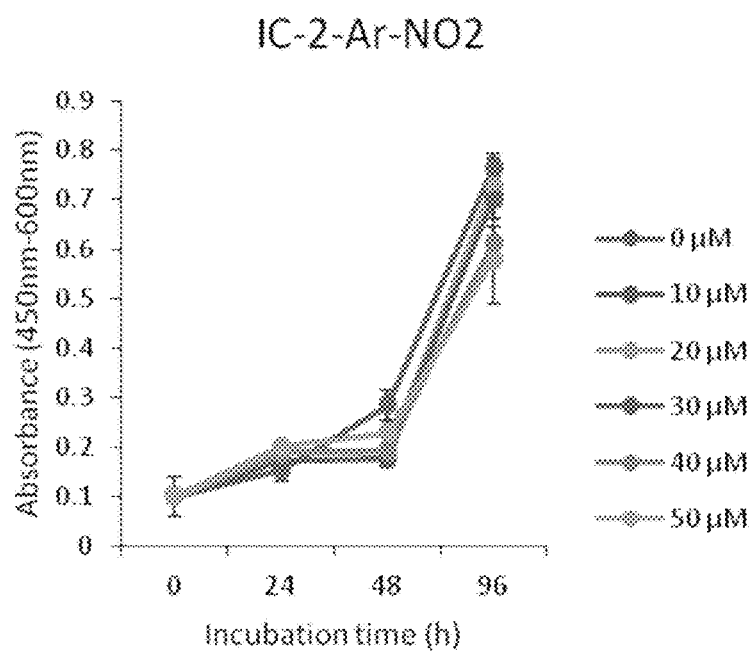

Fig. 22
Growth Inhibition Rate After 96 h (HuH-7 Cells)
IC-2-OTBS
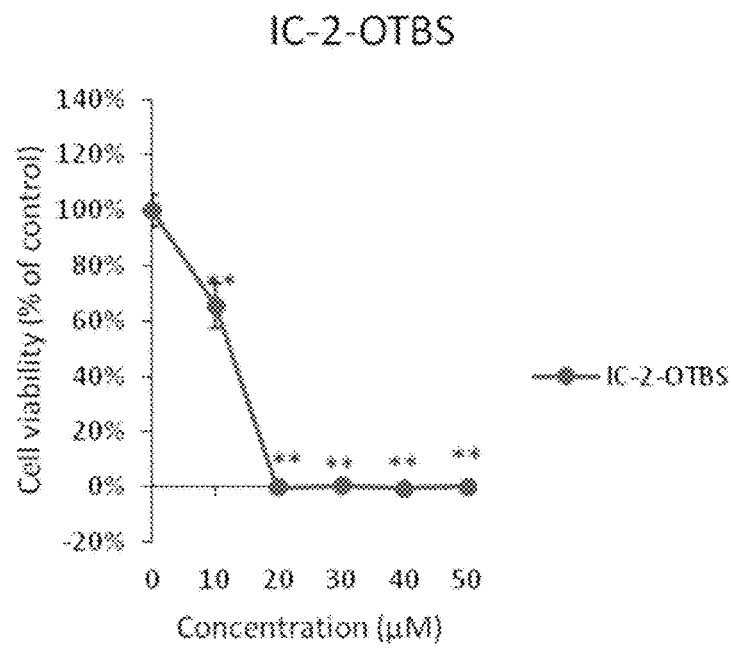
*: p<0.05, **: p<0.01 compared to DMSO
Treatment Time and Cell Viability Curve (HuH-7 Cells)
IC-2-OTBS
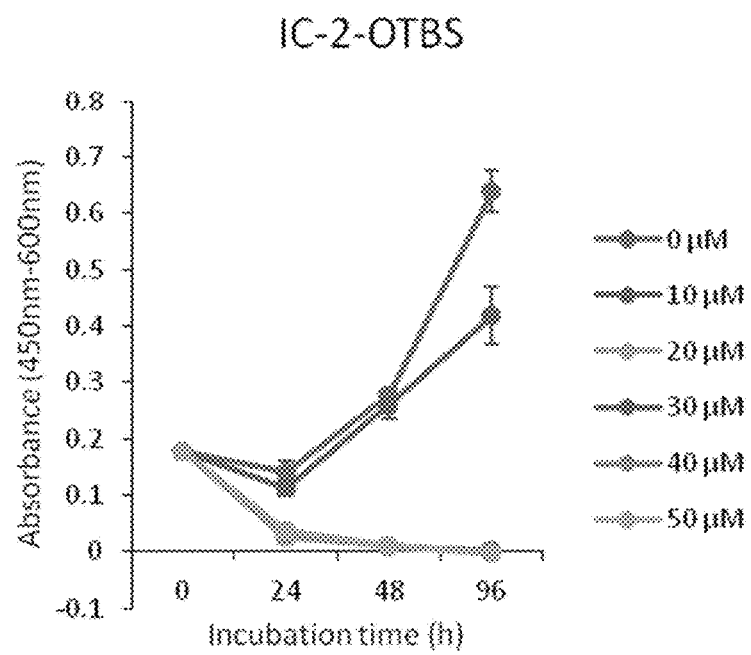

Fig. 23
Growth Inhibition Rate After 96 h (HuH-7 Cells)
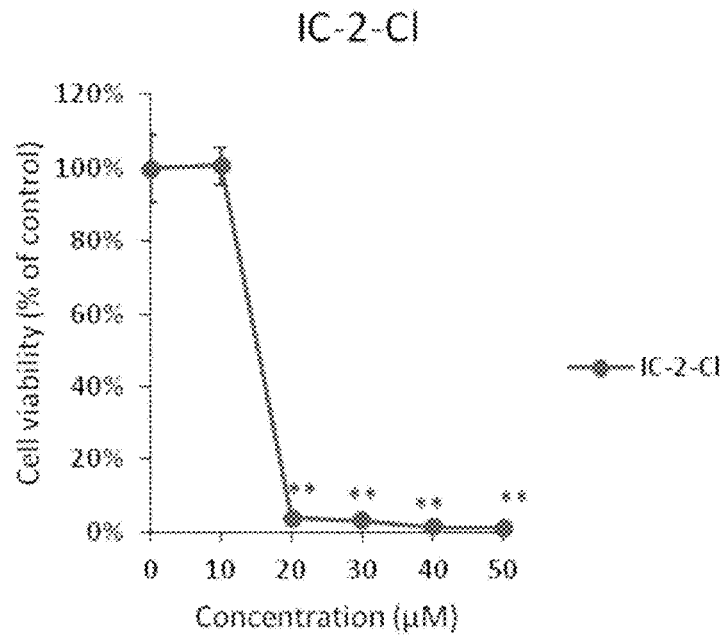
\* : p<0.05, \*\* : p<0.01 compared to DMSO
Treatment Time and Cell Viability Curve (HuH-7 Cells)
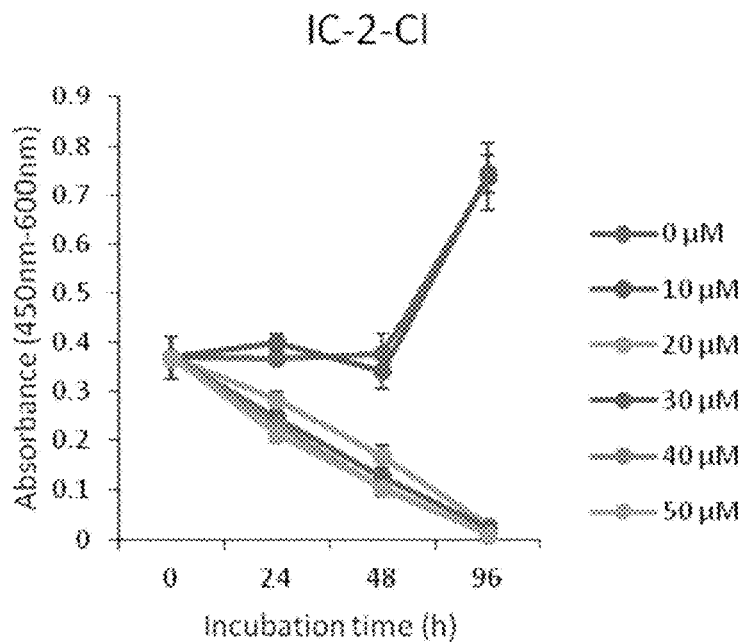

Fig. 24
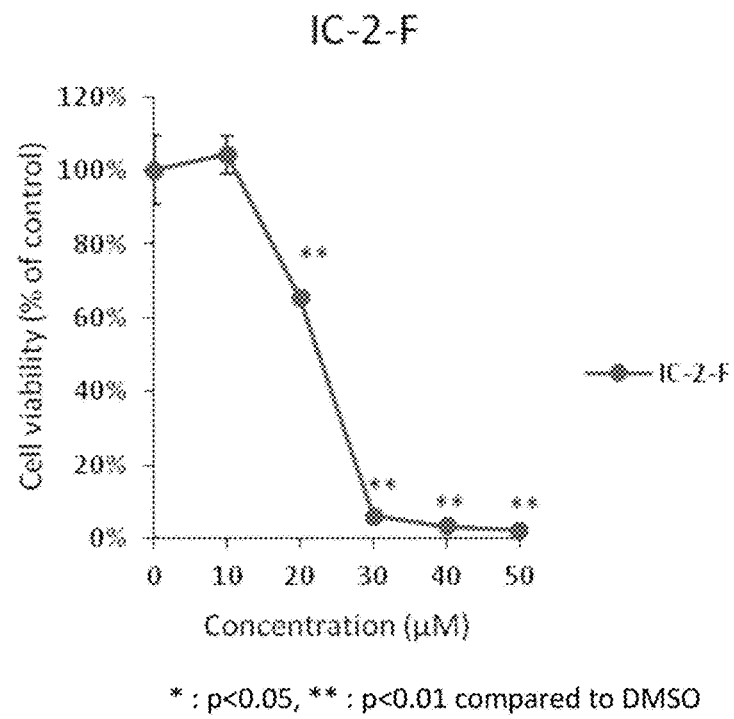
\* : p<0.05, \*\* : p<0.01 compared to DMSO
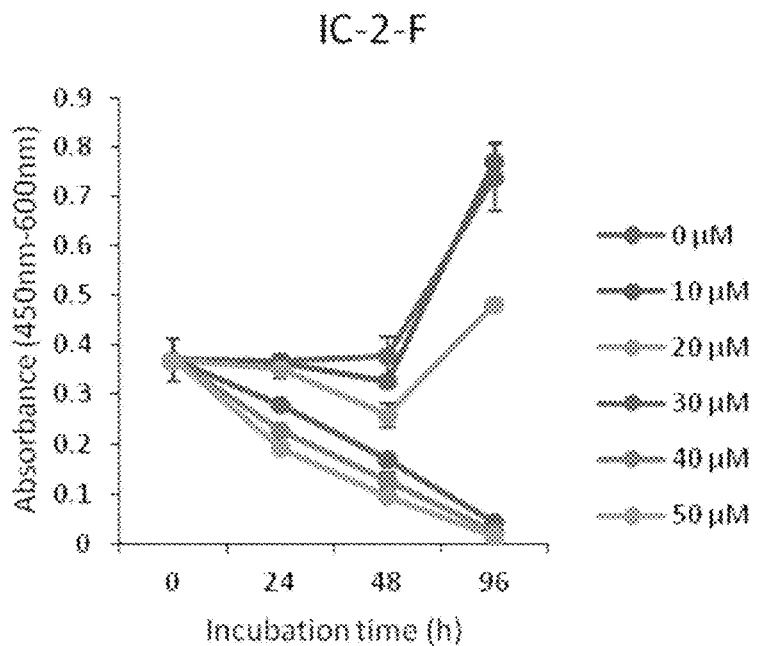

Fig. 25
Growth Inhibition Rate After 96 h (HuH-7 Cells)
IC-2-OMe
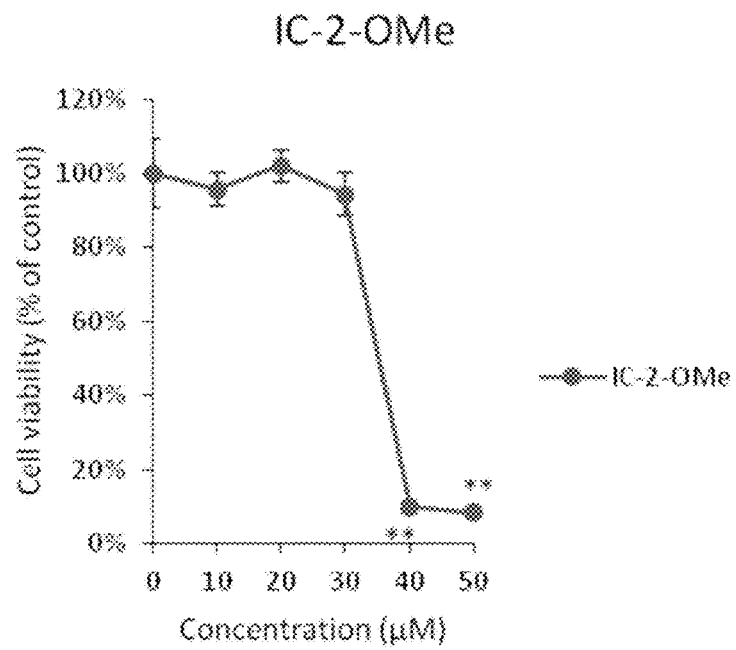
*: p<0.05, **: p<0.01 compared to DMSO
Treatment Time and Cell Viability Curve (HuH-7 Cells)
IC-2-OMe
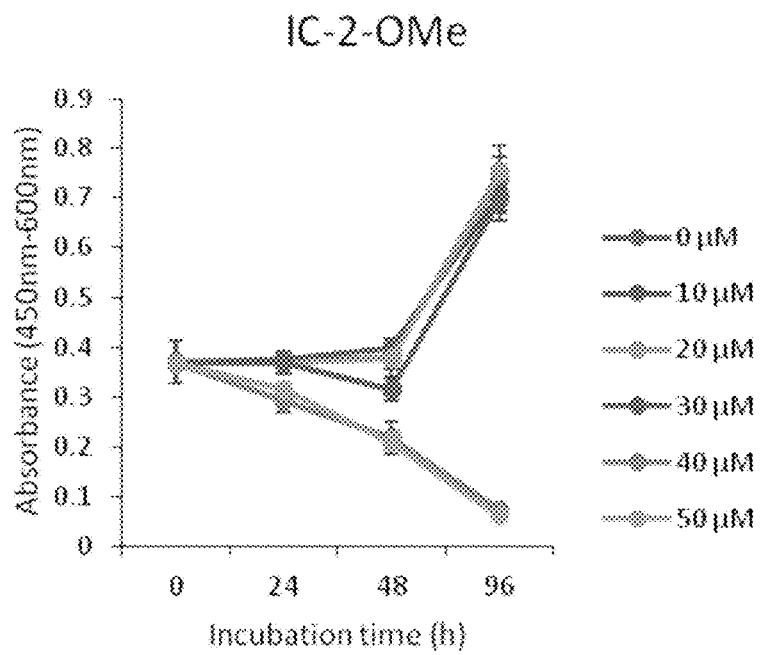

Fig. 26
Growth Inhibition Rate After 96 h (HuH-7 Cells)
IC-2-NO2
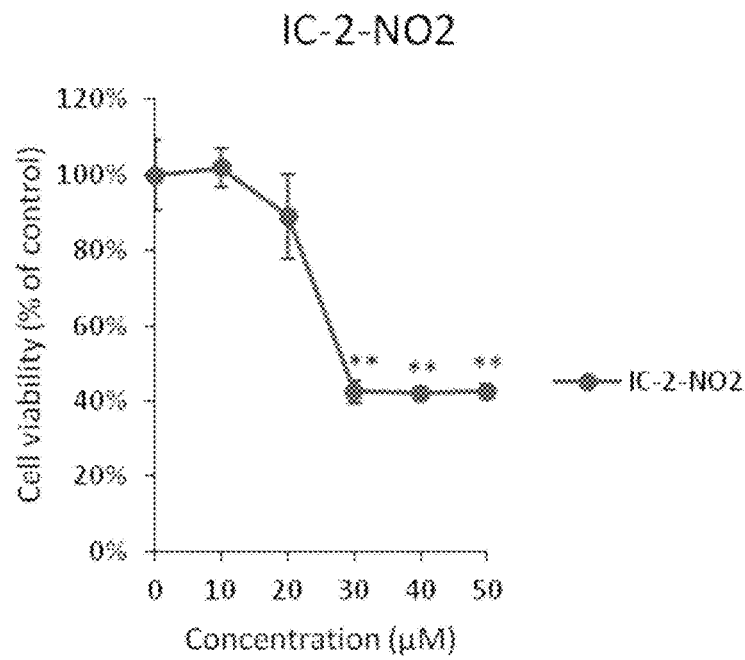
*: $p<0.05$, **: $p<0.01$ compared to DMSO
Treatment Time and Cell Viability Curve (HuH-7 Cells)
IC-2-NO2
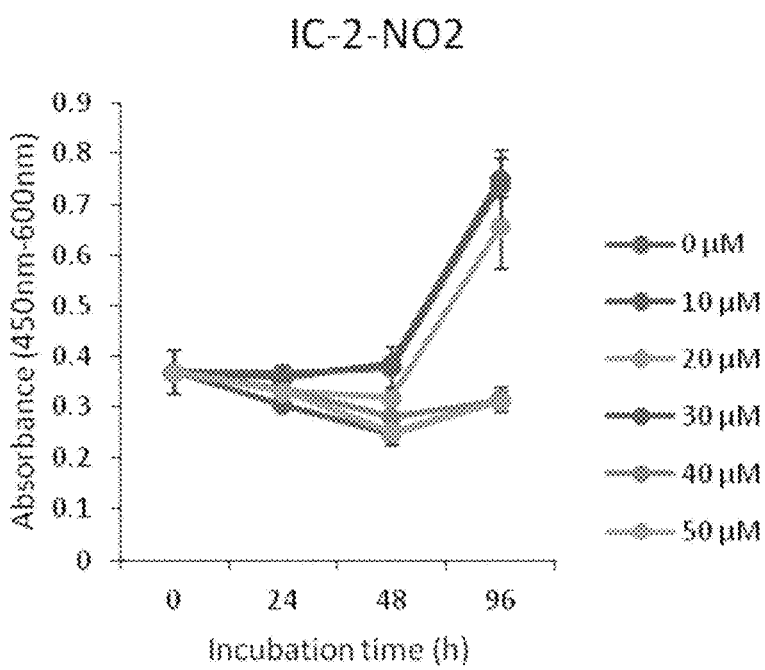

Fig. 27
Growth Inhibition Rate After 96 h (HuH-7 Cells)
IC-2-OMOM
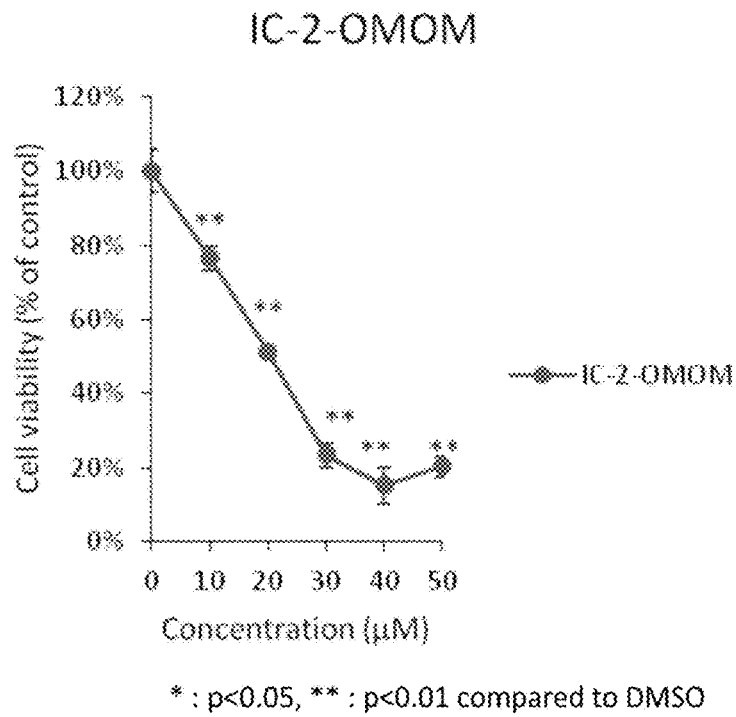
*: $p<0.05$, **: $p<0.01$ compared to DMSO
Treatment Time and Cell Viability Curve (HuH-7 Cells)
IC-2-OMOM
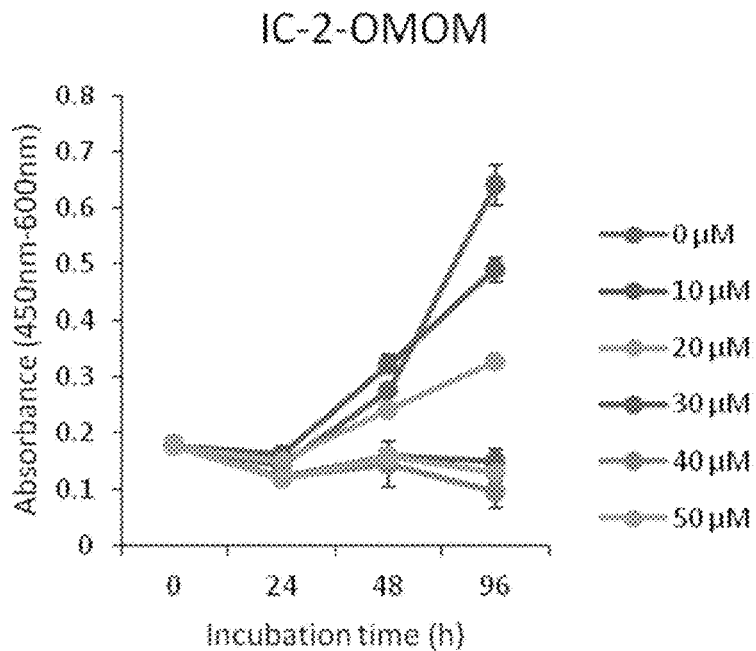

Fig. 28
Growth Inhibition Rate After 96 h (HuH-7 Cells)
IC-2-OPMB
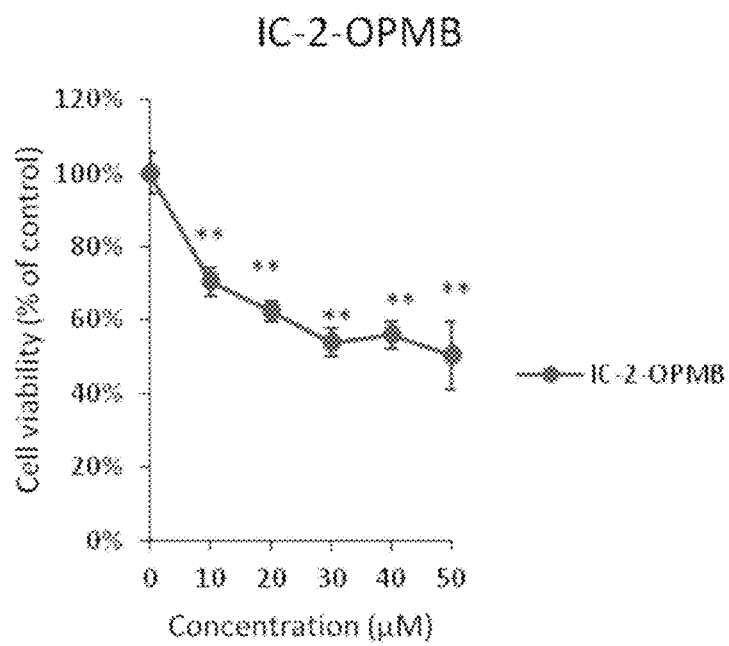
*: p<0.05, **: p<0.01 compared to DMSO
Treatment Time and Cell Viability Curve (HuH-7 Cells)
IC-2-OPMB
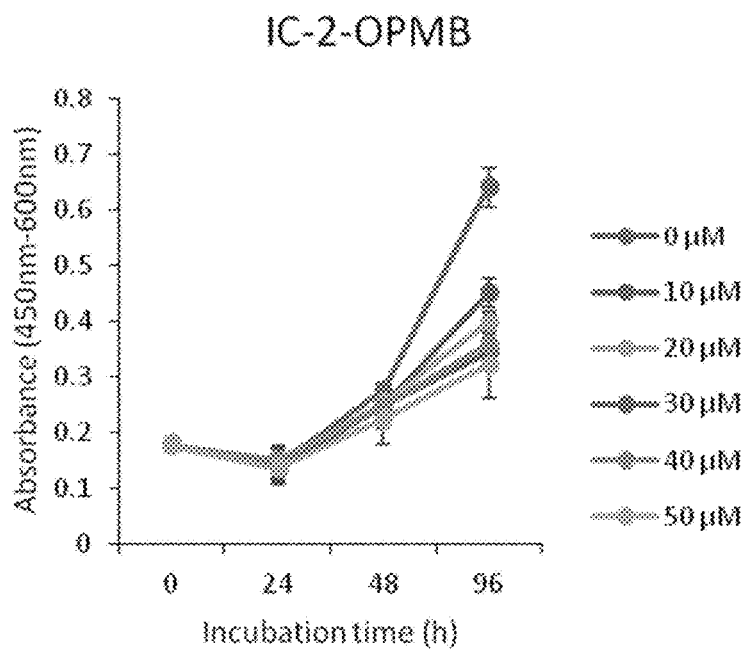

Fig. 29
Growth Inhibition Rate After 96 h (HuH-7 Cells)
IC-2-OH
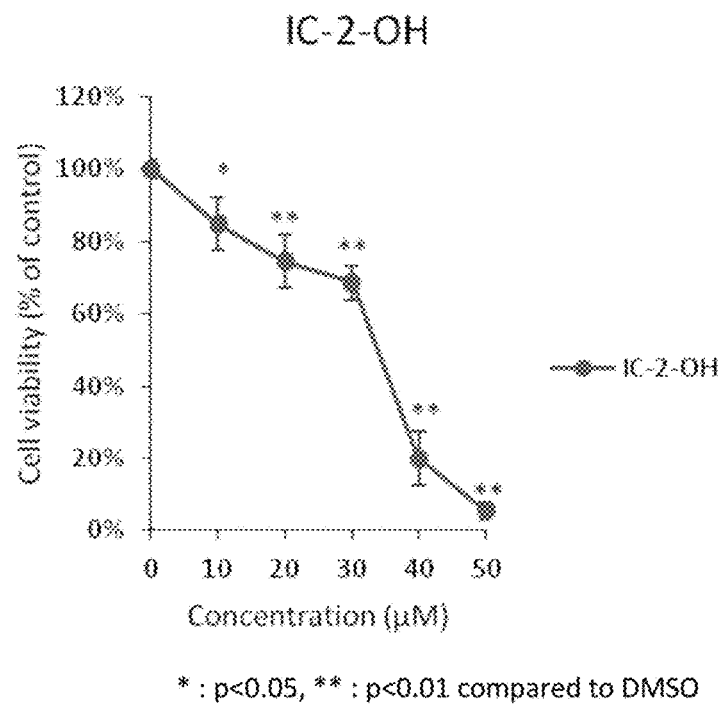
*: p<0.05, **: p<0.01 compared to DMSO
Treatment Time and Cell Viability Curve (HuH-7 Cells)
IC-2-OH
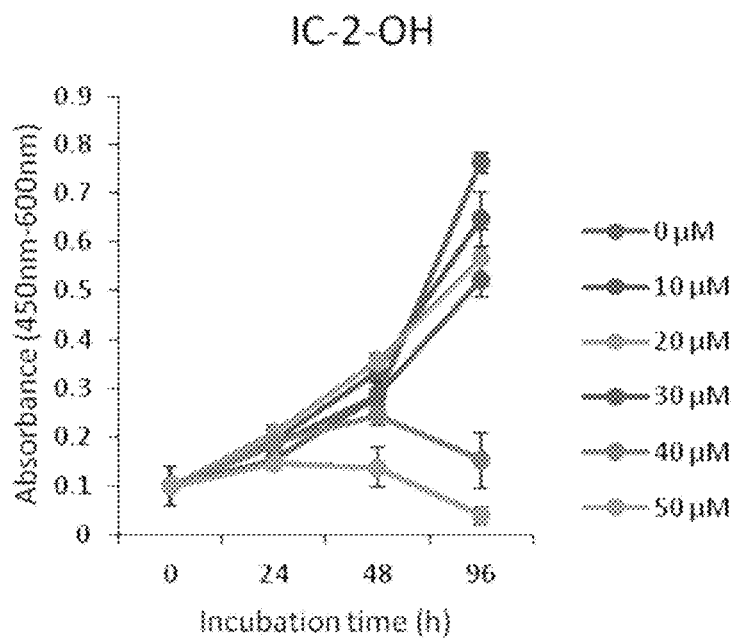

Fig. 30
Growth Inhibition Rate After 96 h (HuH-7 Cells)
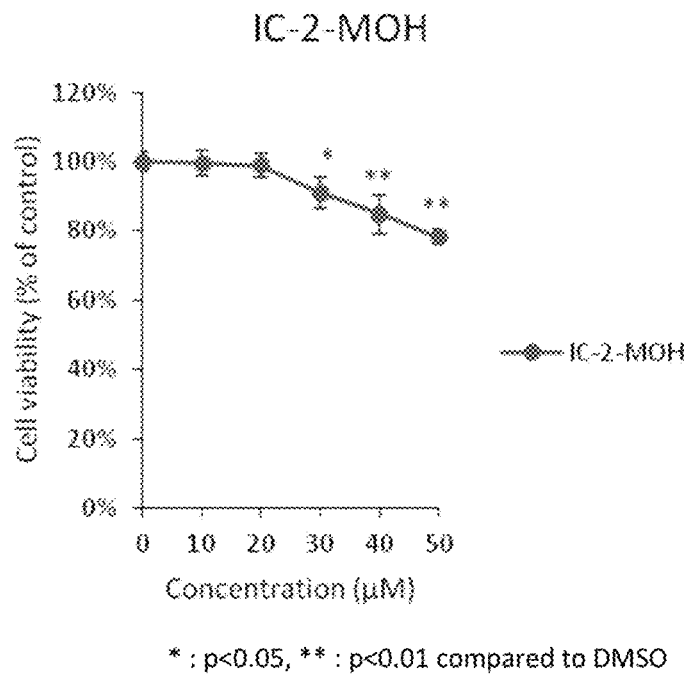
*: p<0.05, **: p<0.01 compared to DMSO
Treatment Time and Cell Viability Curve (HuH-7 Cells)
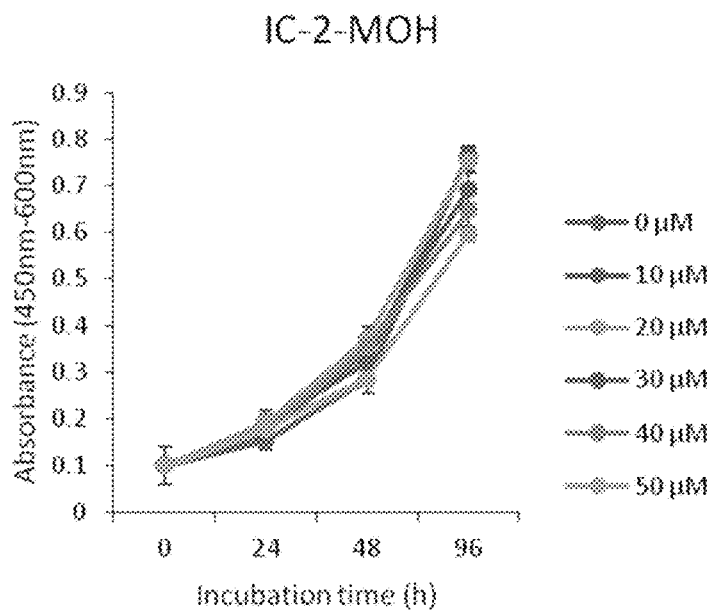

Fig. 31
Growth Inhibition Rate After 96 h (HuH-7 Cells)
7c-NT
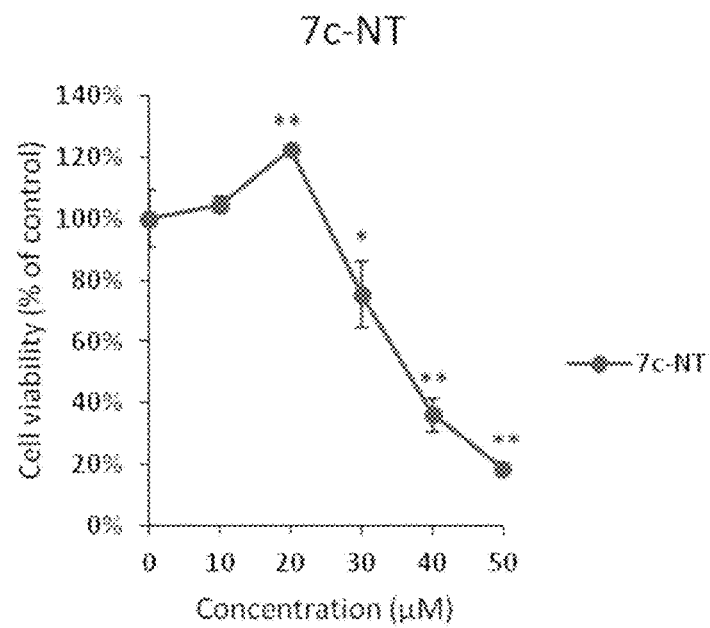
*: p<0.05, **: p<0.01 compared to DMSO
Treatment Time and Cell Viability Curve (HuH-7 Cells)
7c-NT
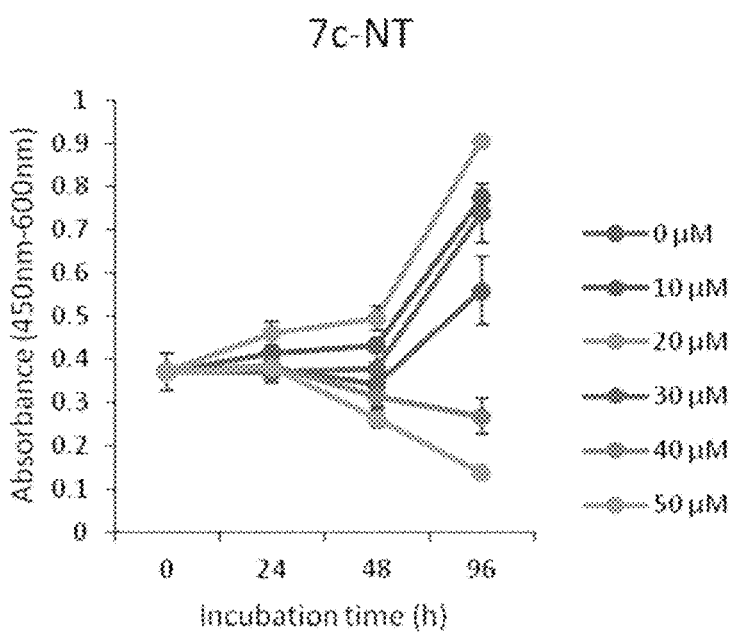

** : p<0.01 compared to DMSO

** : p<0.01 compared to DMSO

Glycogen Synthesis at Day 8 (UE7T-13 Cells)

Fig. 47
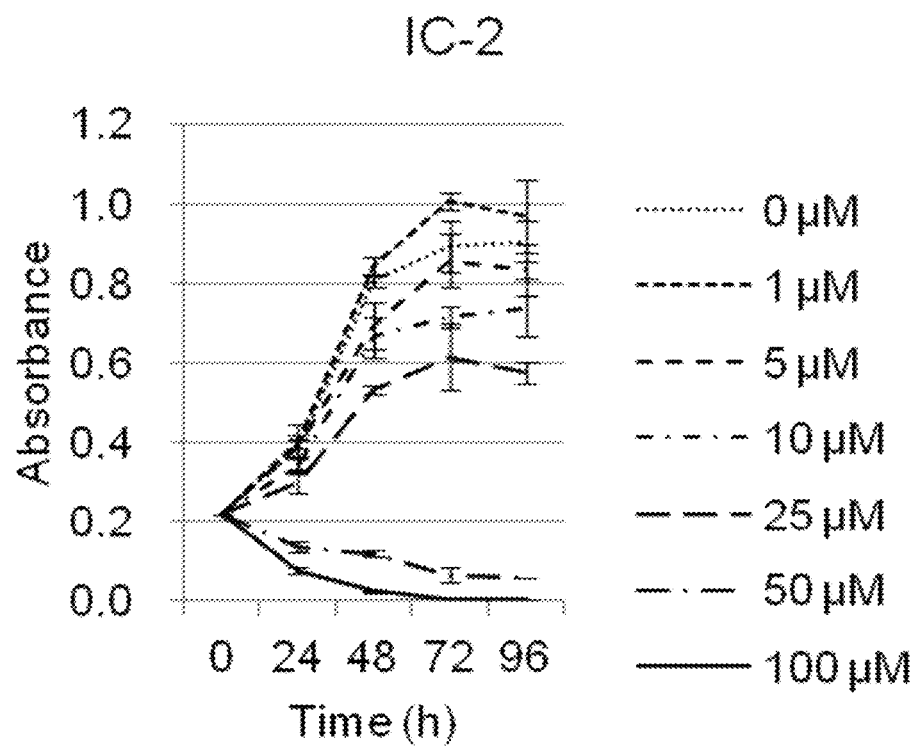
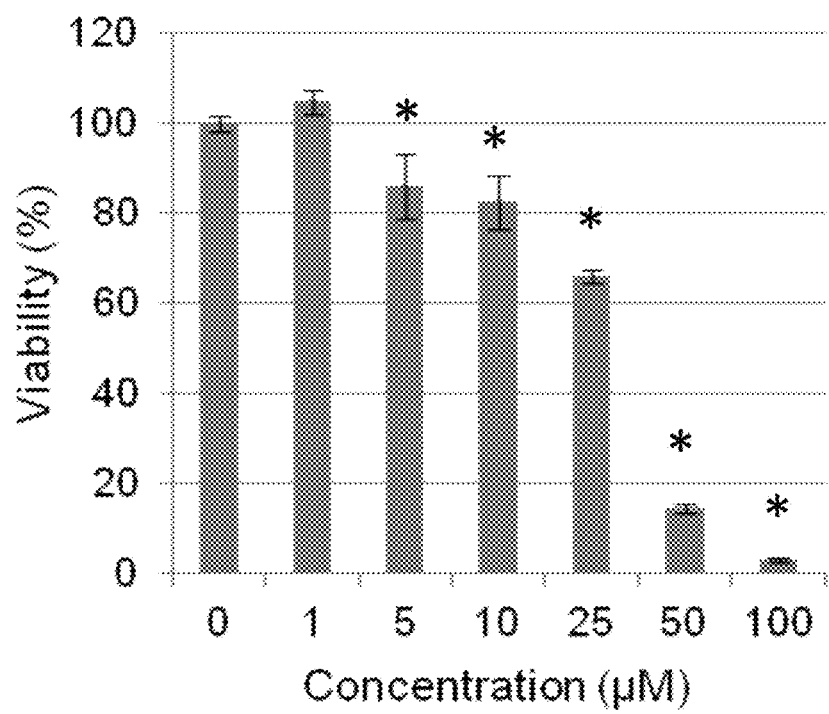

Fig. 50
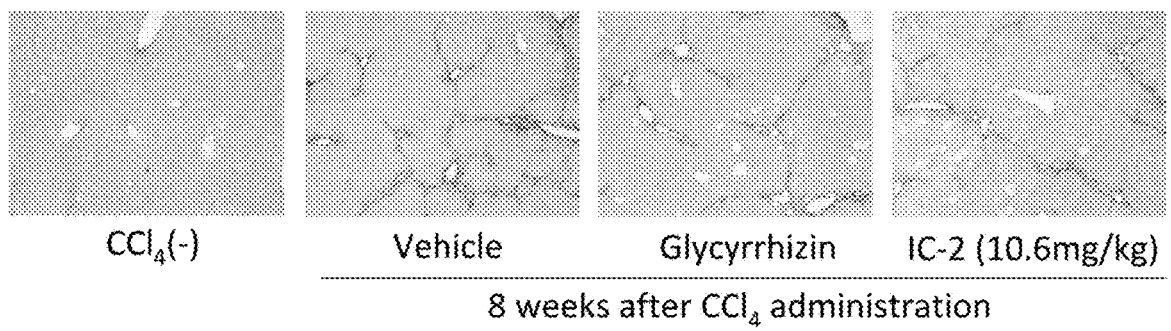
8 weeks after CCl₄ administration
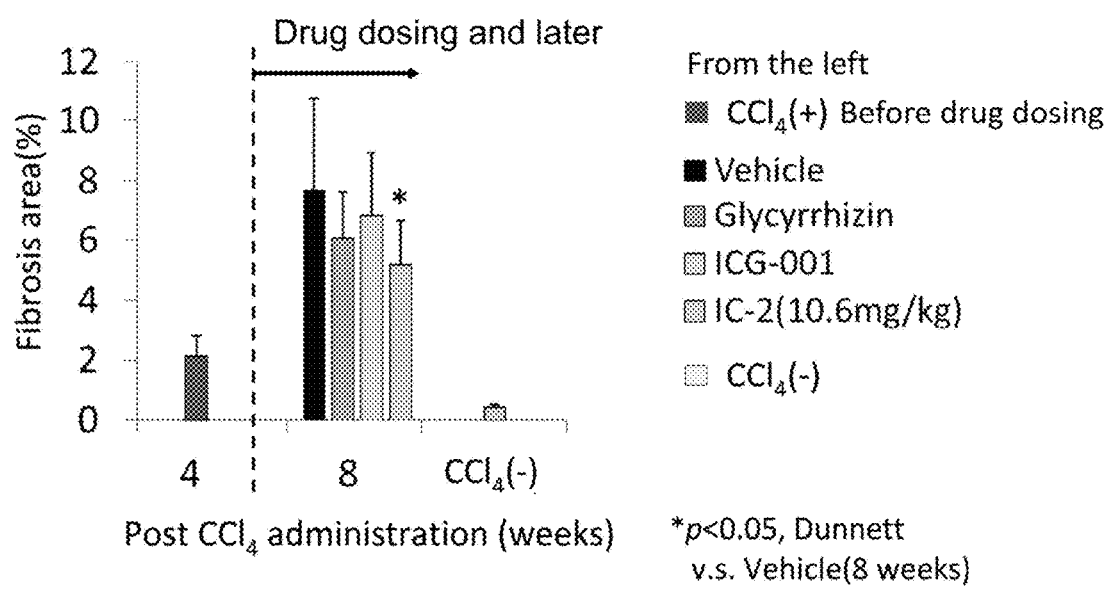
From the left
- CCl₄(+) Before drug dosing
- Vehicle
- Glycyrrhizin
- ICG-001
- IC-2(10.6mg/kg)
- CCl₄(-)
*$p<0.05$, Dunnett v.s. Vehicle(8 weeks)

Fig. 52
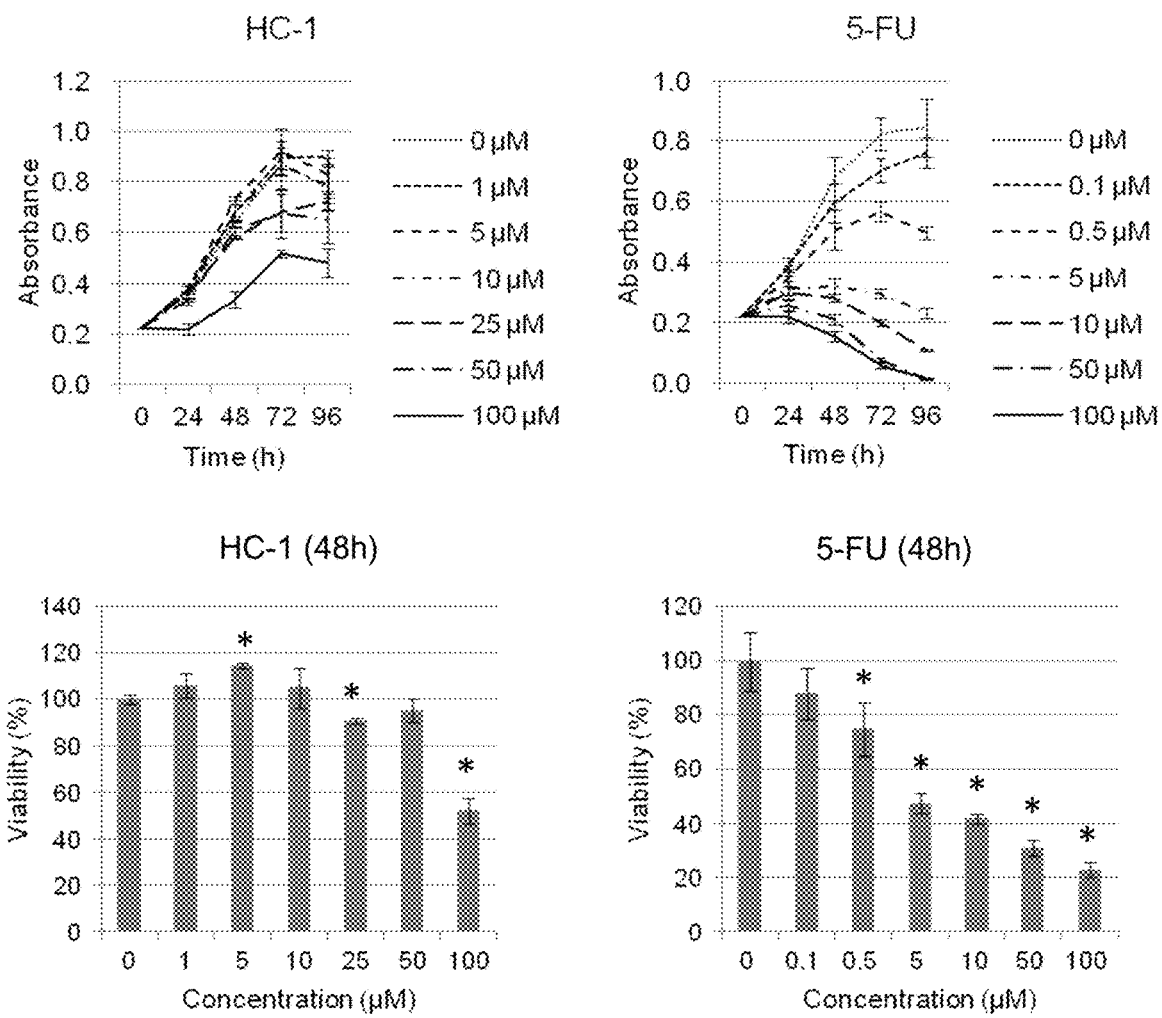
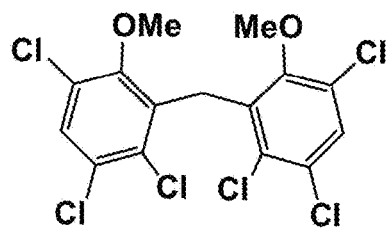
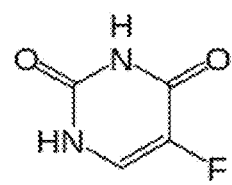

Red: Annexin V
Green: PI

SUPPRESSION AND REGENERATION PROMOTING EFFECT OF LOW MOLECULAR WEIGHT COMPOUND ON CANCER AND FIBROSIS

TECHNICAL FIELD

The present invention relates to therapeutic drugs for malignant tumors or fibrosis.

BACKGROUND ART

Examples of the leading causes of human death include malignant tumors, heart disease, and cerebrovascular disease. Among them, the mechanism of causing malignant tumors is complicated, so that the malignant tumors, in particular, can be said to be a hard-to-prevent and hard-to-treat disease.

Examples of a symptom that causes malignant tumors include tissue fibrosis. For instance, when liver fibrosis advances, this causes hepatic cirrhosis, leading to liver cancer. In addition, fibrosis occurs in the lung, kidney, heart, skin, etc. Non-Patent Literature 1 describes the outcome of a clinical trial on pirfenidone involved with fibrosis treatment.

The present inventors have reported low-molecular-weight compounds in three publications (Non-Patent Literatures 2 and 3 and Patent Literature 1). Non-Patent Literatures 2 and 3 describe low-molecular-weight compounds that exert an inhibitory effect on proliferation of liver cancer cells and an inhibitory effect on a Wnt/β-catenin signal. However, neither Non-Patent Literature 2 nor 3 describes what kinds of the structure and function of a compound cause the compound to exert a growth inhibitory effect on liver cancer cells.

Patent Literature 1 describes that PN-1-2, PN-3-4, PN-3-13, HC-1, and IC-2 inhibit a Wnt/β-catenin signal in a mesenchymal stem cell, thereby inducing differentiation of the mesenchymal stem cell into hepatocytes. This literature, however, discloses nothing about inhibition of proliferation of cancer cells.

CITATION LIST

Patent Literature

[Patent Literature 1] WO02012/141038

Non-Patent Literature

[Non-Patent Literature 1] Noble et al., Lancet, 2011, May 21; 377(9779): 1760-9.
[Non-Patent Literature 2] Sakabe et al., "Kanzo (Liver)", vol. 53, Supplement 1, 2012, A226, WS-54.
[Non-Patent Literature 3] Seto et al., "Kanzo (Liver)", vol. 54, Supplement 1, 2013, P-12.

SUMMARY OF INVENTION

Technical Problem

Malignant tumors are one of the leading causes of human death. Hence, conventional treatment strategies are simply insufficient. In the field of treatment of malignant tumors, it is known that the pharmacological effect of a low-molecular-weight compound administered largely varies depending on characteristics of the structure of the individual compound. Also, this field involves considerable uncertainty. Whether or not a desirable pharmacological effect can be achieved is difficult to predict during development of a novel treatment protocol. Because of this, it has been uneasy to identify a novel low-molecular-weight compound that exerts an effect of treating malignant tumors.

Furthermore, as described above, there is an increasing number of reports on research regarding fibrosis treatment. However, there are only a few therapeutic drugs effective in treating fibrosis. Besides, an adverse effect may cause a problem to some patients. Hence, conventional anti-fibrosis agents are simply insufficient.

The present invention has been made in view of the above situations. The purpose of the present invention is to provide a novel therapeutic drug for malignant tumors or fibrosis.

Solution to Problem

The present inventors have conducted intensive research and, as a result, have discovered that the low-molecular-weight compound represented by the following formula (1) exerts an anti-malignant tumor effect. In addition, it has been found that the low-molecular-weight compound represented by the following formula (1) also exerts an inhibitory effect on fibrosis. Then, the present inventors have completed the present invention on the basis of these findings.

Specifically, an embodiment of the present invention provides a compound, a salt thereof, or a solvate thereof, the compound represented by formula (1):

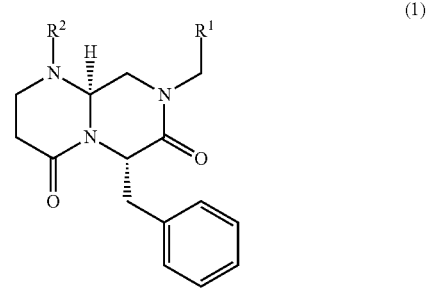

(1)

wherein substituents $R^1$ and $R^2$ represent the following case (a) or (b):
(a) $R^1$ is optionally substituted phenyl, and
$R^2$ is H, optionally substituted phenyl, or —C(O)NHR$^3$ where the $R^3$ is H, $C_{1-6}$ alkyl, or optionally substituted benzyl; or
(b) $R^1$ is optionally substituted naphthyl or optionally substituted phenyl, and
$R^2$ is optionally substituted phenyl or —C(O)NHR$^4$ where the $R^4$ is H, $C_{1-6}$ alkyl, or optionally substituted siloxybenzyl.

This compound, a salt thereof, or a solvate thereof may be used to treat malignant tumors or fibrosis.

Another aspect of the present invention provides a therapeutic drug for a malignant tumor or fibrosis, which drug includes a compound represented by formula (1), a salt thereof, or a solvate thereof.

Another embodiment of the present invention provides a therapeutic drug for a malignant tumor, comprising a compound, a salt thereof, or a solvate thereof, wherein the therapeutic drug is used in combination therapy using 5-FU and the compound, or the salt thereof, or the solvate thereof, the compound represented by formula (2):

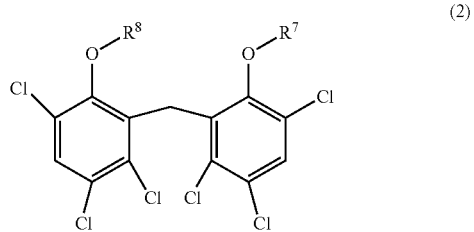

(2)

wherein $R^7$ and $R^8$ are the same or different and each represent optionally substituted $C_{1-6}$ alkyl or optionally substituted $C_{2-6}$ alkenyl.

Another embodiment of the present invention provides a 5-FU-containing therapeutic drug for a malignant tumor, wherein the therapeutic drug is used in combination therapy using 5-FU and a compound represented by formula (2), a salt thereof, or a solvate thereof.

Advantages

Malignant tumors or fibrosis can be treated in accordance with the present invention.

BRIEF DESCRIPTION OF THE DRAWINGS

FIGS. 10 to 14 are tables listing the structural formula and spectrum data of each of the low-molecular-weight compounds of Example 1.

FIGS. 15 to 31 are graphs showing the results of examining an anti-tumor effect of each low-molecular-weight compound.

FIGS. 46 to 48 are graphs showing the results of examining an anti-tumor effect of each low-molecular-weight compound.

FIG. 50 to 51 are photographs and graphs showing the results of testing an anti-fibrosis effect of each low-molecular-weight compound.

FIG. 52 is graphs showing the results of examining an anti-tumor effect of each low-molecular-weight compound.

DESCRIPTION OF EMBODIMENTS

Figure 1:
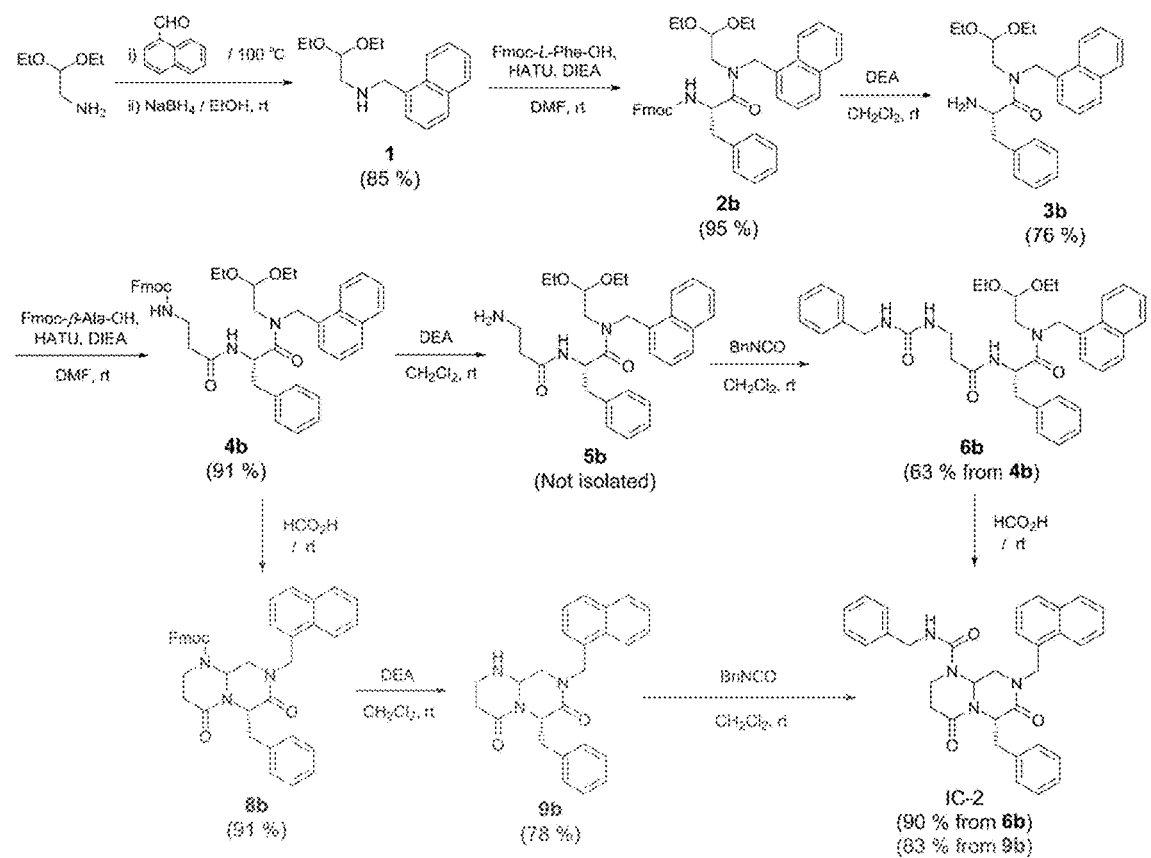
FIGS. 1 to 9 are diagrams illustrating synthetic schemes of low-molecular-weight compounds of Example 1.
Figure 2:
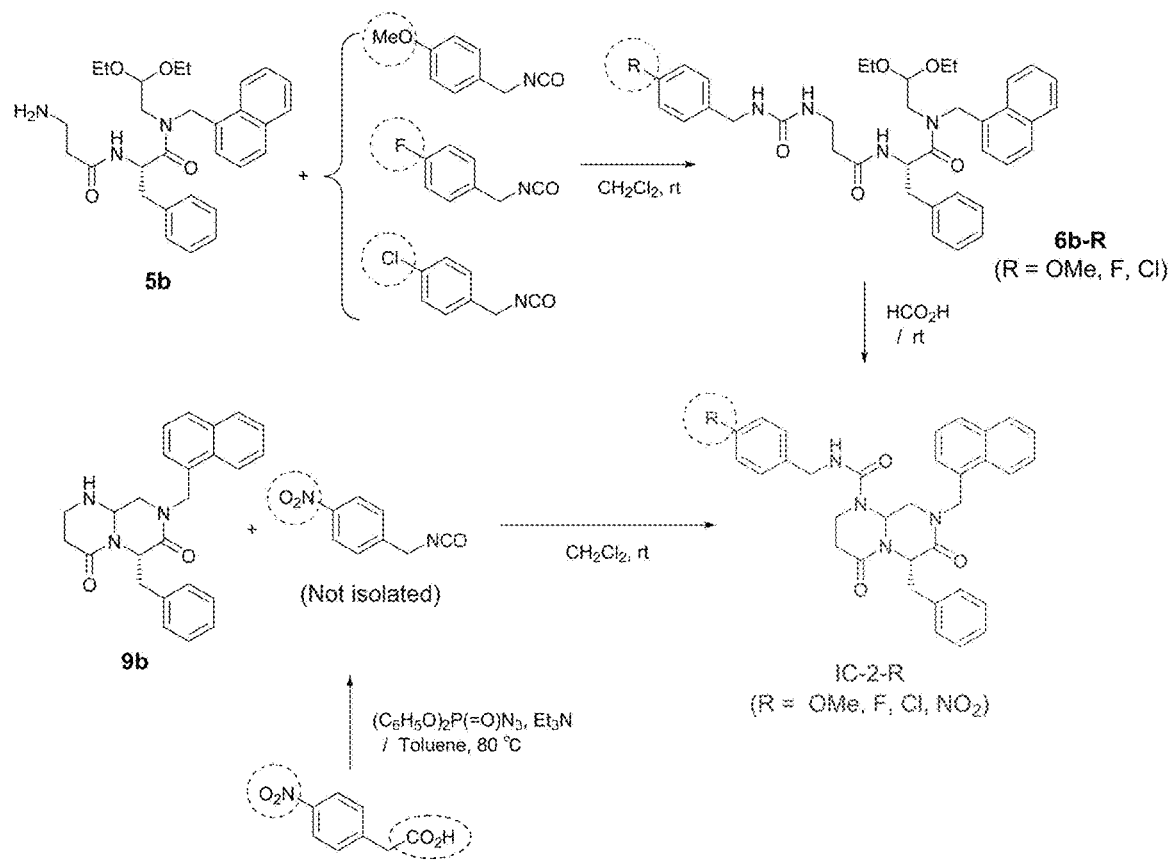
Figure 3:
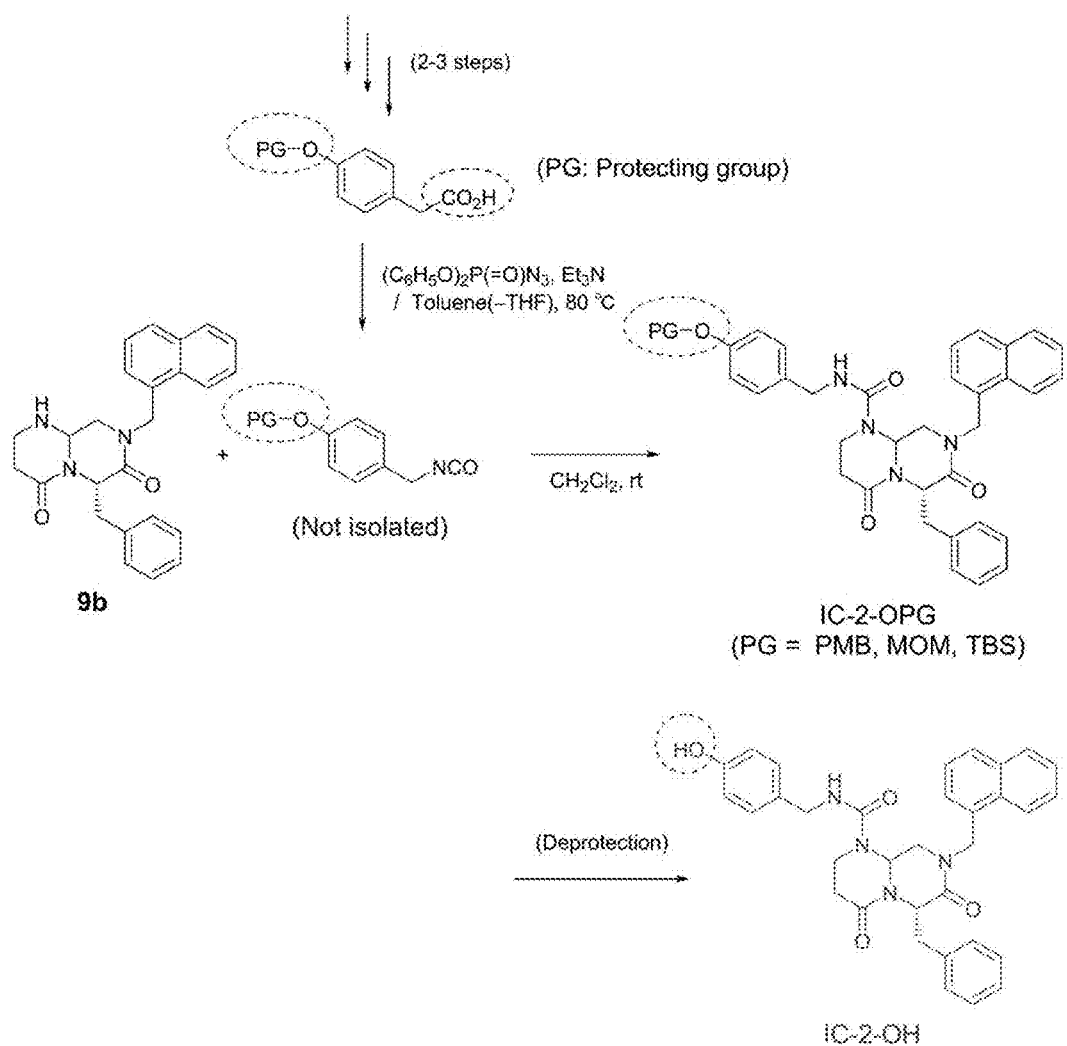
Figure 4:
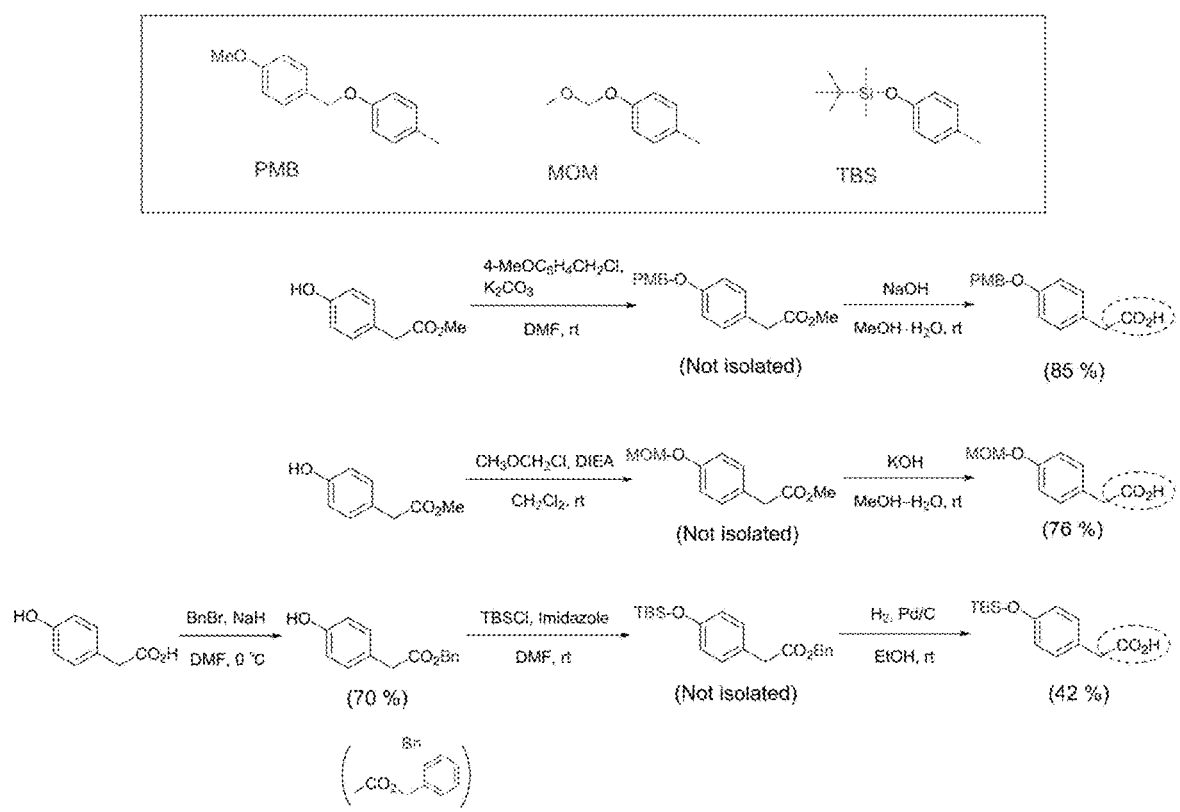
Figure 5:
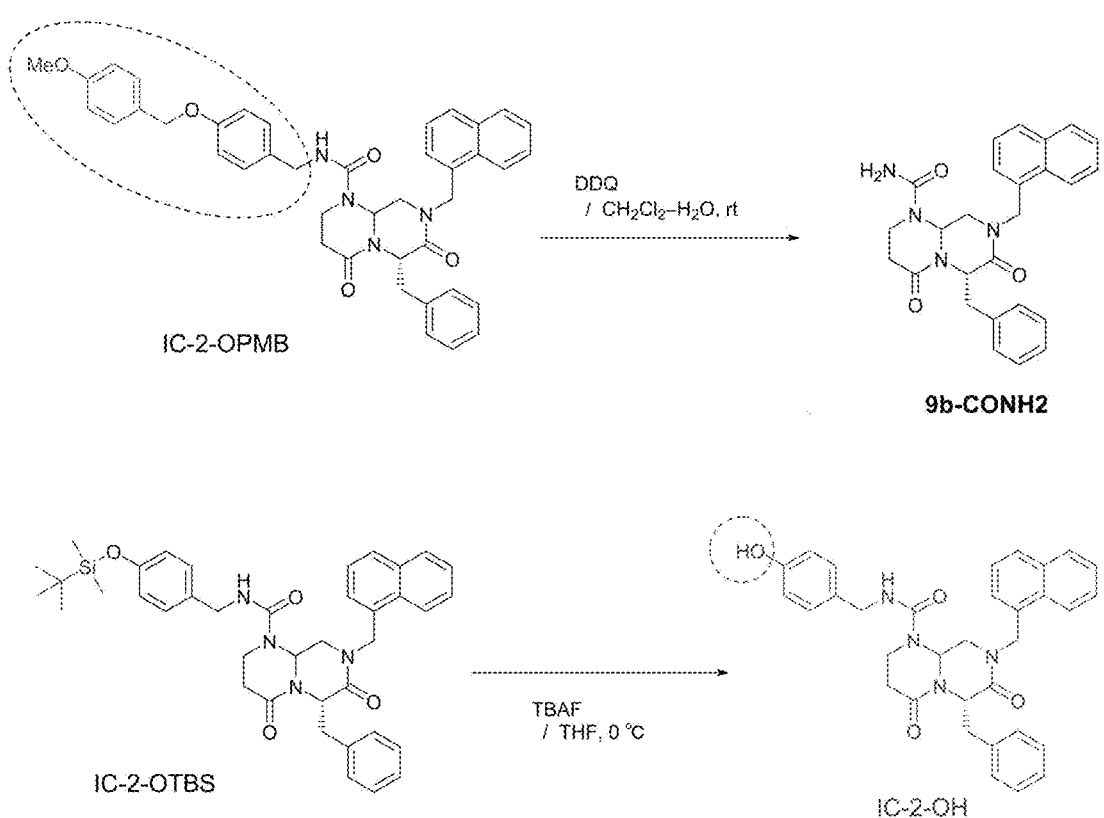
Figure 6:
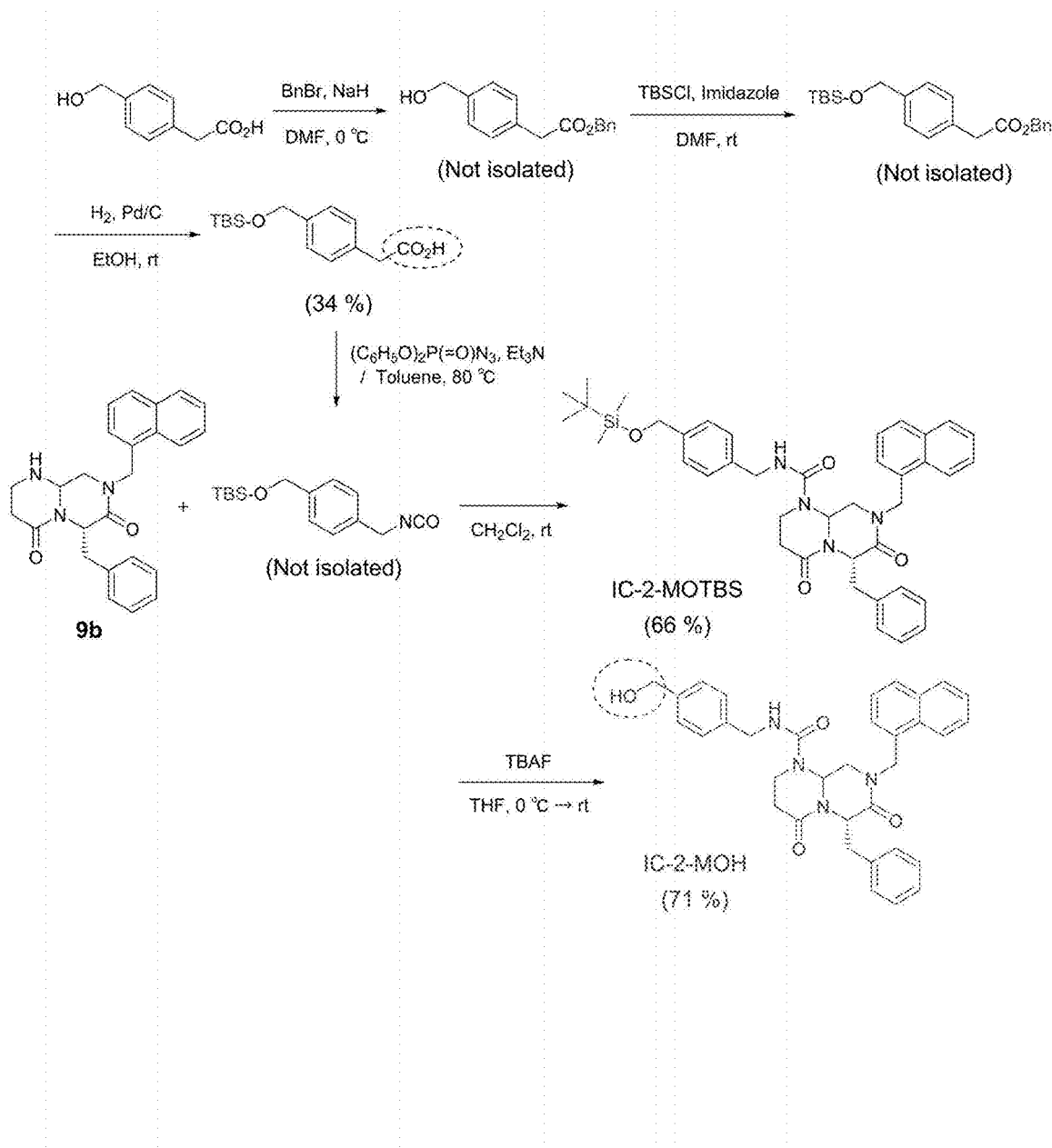
Figure 7:
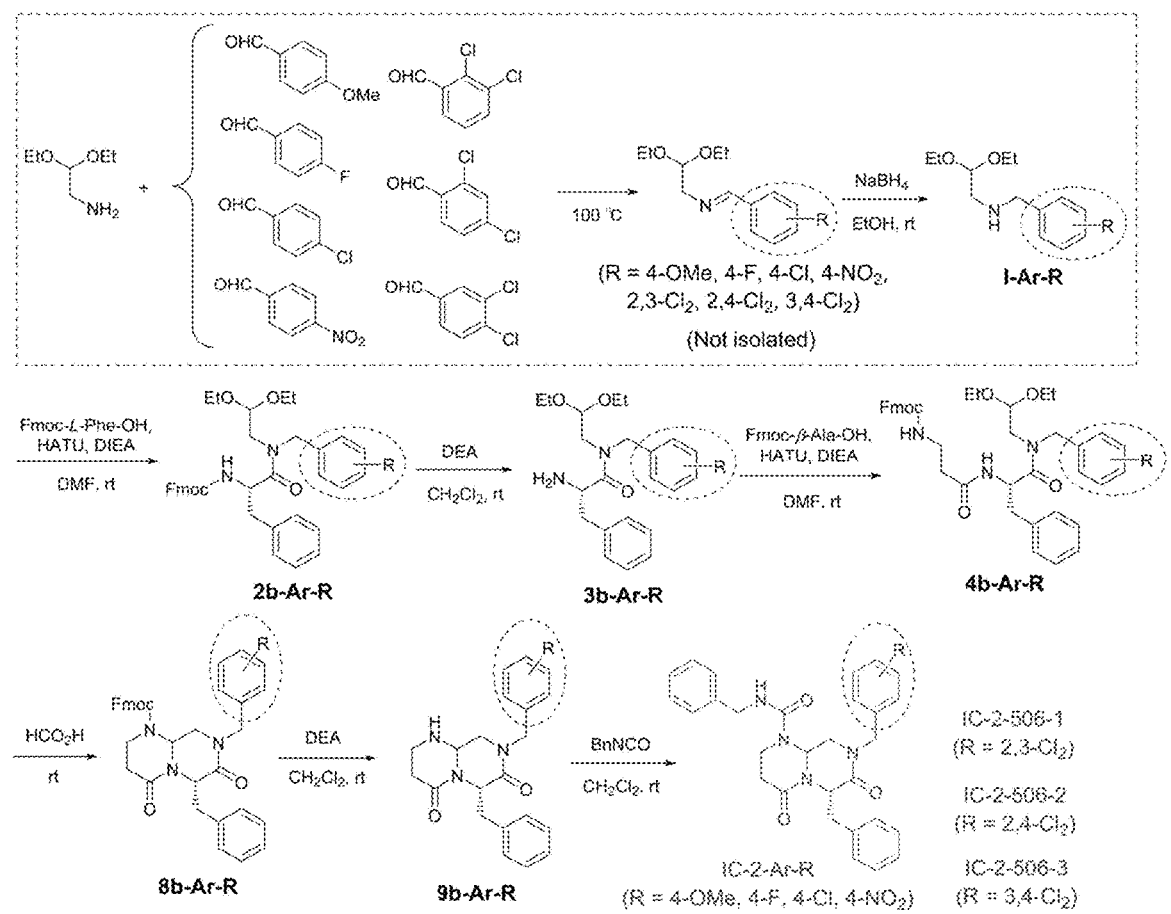
Figure 8:
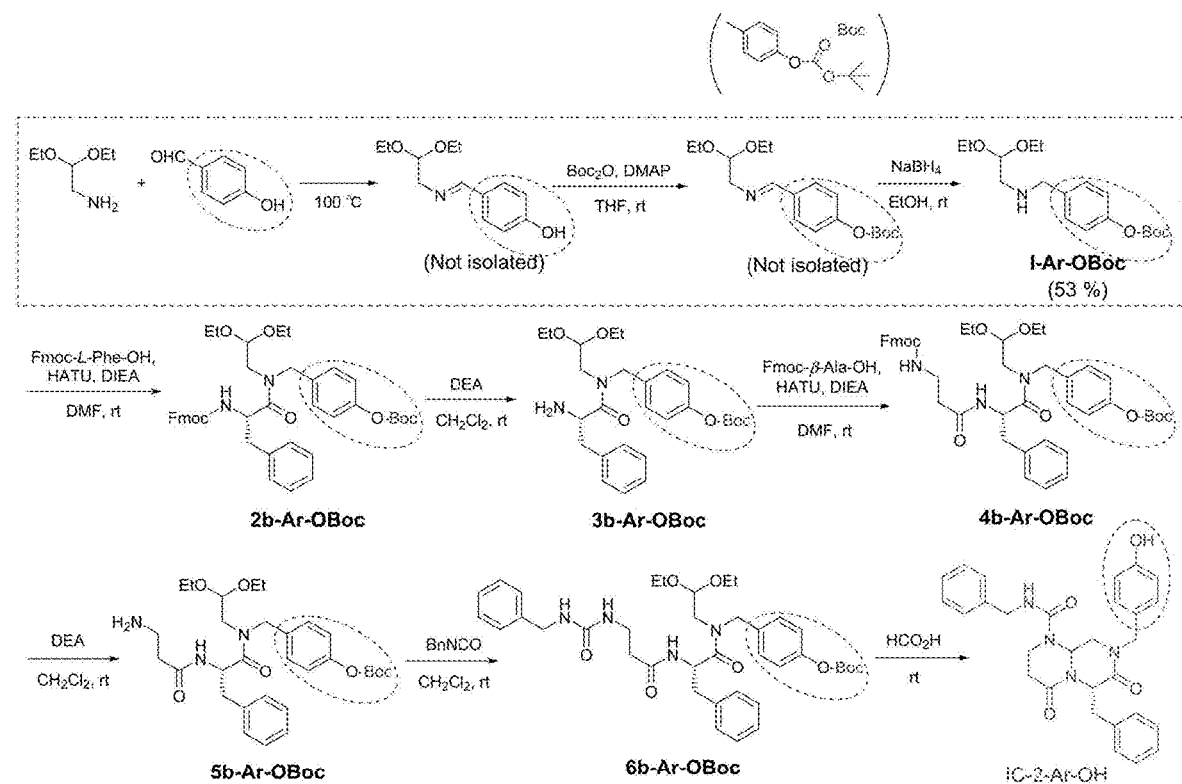
Figure 9:
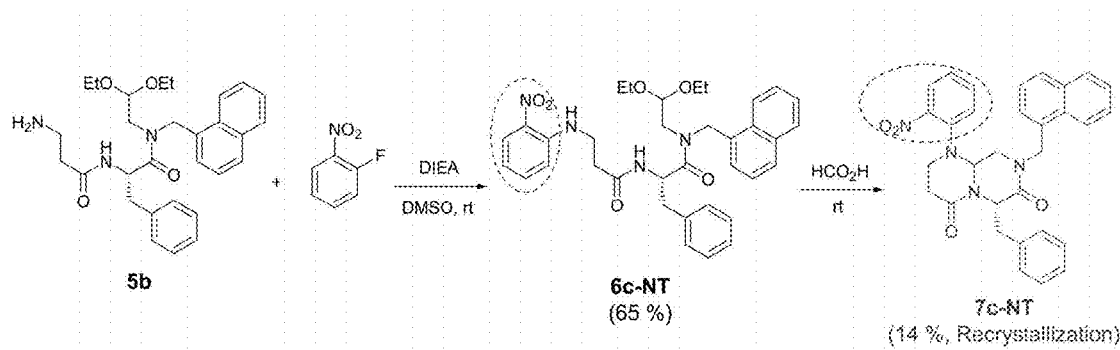

Hereinafter, embodiments of the present invention will be described in detail. Note that descriptions are not repeated so as to avoid redundancy.

An embodiment of the present invention provides a compound represented by formula (1), a salt thereof, or a solvate thereof. This compound, a salt thereof, or a solvate thereof may be used to treat malignant tumors or fibrosis. In addition, this compound, a salt thereof, or a solvate thereof may be used to induce differentiation of a mesenchymal stem cell into hepatocytes.

An embodiment of the present invention provides a therapeutic drug for a malignant tumor, comprising a compound represented by formula (1), a salt thereof, or a solvate thereof. This therapeutic drug may be used to treat malignant tumors.

An embodiment of the present invention provides a therapeutic drug for a cancer stem cell, comprising a compound represented by formula (1), a salt thereof, or a solvate thereof. This therapeutic drug may be used to treat cancer stem cells.

An embodiment of the present invention provides a therapeutic drug for inhibiting growth of a malignant tumor cell or a cancer stem cell, comprising a compound represented by formula (1), a salt thereof, or a solvate thereof. This therapeutic drug may be used to inhibit proliferation of malignant tumor cells or cancer stem cells.

An embodiment of the present invention provides a therapeutic drug for inhibiting relapse of a malignant tumor, comprising a compound represented by formula (1), a salt thereof, or a solvate thereof. This inhibitory drug may be used to inhibit the relapse of a malignant tumor.

An embodiment of the present invention provides a therapeutic drug for fibrosis, comprising a compound represented by formula (1), a salt thereof, or a solvate thereof. This therapeutic drug may be used to treat fibrosis.

An embodiment of the present invention provides a therapeutic drug for a fibrosis-associated disease, comprising a compound represented by formula (1), a salt thereof, or a solvate thereof. This therapeutic drug may be used to treat a disease accompanied by fibrosis.

An embodiment of the present invention provides an inducer of differentiation from a mesenchymal stem cell into hepatocytes, comprising a compound represented by formula (1), a salt thereof, or a solvate thereof. This inducer may be used to efficiently induce differentiation from mesenchymal stem cells into hepatocytes.

An embodiment of the present invention provides a method for producing hepatocytes, comprising the step of causing a compound represented by formula (1), a salt thereof, or a solvate thereof to contact cells. Use of this method makes it possible to efficiently produce hepatocytes. This method may further comprise a step of recovering the hepatocytes or a step of detecting a hepatocyte marker.

An embodiment of the present invention provides a compound represented by formula (1), wherein substituents $R^1$ and $R^2$ are represented by the following case (a) or (b):

(a) $R^1$ is optionally substituted phenyl, and
$R^2$ is H, optionally substituted phenyl, or —C(O)NHR$^3$ where the $R^3$ is H, $C_{1-6}$ alkyl, or optionally substituted benzyl; or (b) $R^1$ is optionally substituted naphthyl or optionally substituted phenyl, and
$R^2$ is optionally substituted phenyl or —C(O)NHR$^4$ where the $R^4$ is H, $C_{1-6}$ alkyl, or optionally substituted siloxybenzyl.

From the viewpoint of achieving a better anti-tumor effect, fibrosis resistance, or hepatocyte differentiation-inducing effect in accordance with an embodiment of the present invention, the above substituents $R^1$ and $R^2$ are preferably as follows.

The $R^1$ of case (a) is phenyl having a substituent $R^5$ where the $R^5$ is at least one substituent selected from the group consisting of H, halogen, nitro, amino, cyano, OH, $C_{1-6}$ alkyl, $C_{1-6}$ halogenoalkyl, $C_{1-6}$ hydroxyalkyl, $C_{1-6}$ alkylamino, $C_{1-6}$ alkoxy, $C_{1-6}$ halogenoalkoxy, $C_{1-6}$ hydroxyalkoxy, and $C_{1-6}$ alkoxyamino.

The $R^2$ of case (a) is H, phenyl having a substituent $R^5$, —C(O)NHR$^3$ where the $R^3$ is benzyl having a substituent $R^6$ where the $R^6$ is at least one substituent selected from the group consisting of H, halogen, nitro, amino, cyano, OH, $C_{1-6}$ alkyl, $C_{1-6}$ halogenoalkyl, $C_{1-6}$ hydroxyalkyl, $C_{1-6}$ alkylamino, $C_{1-6}$ alkoxy, $C_{1-6}$ halogenoalkoxy, $C_{1-6}$ hydroxyalkoxy, $C_{1-6}$ alkoxyamino, $C_{1-6}$ alkoxy-substituted $C_{1-6}$ alkoxy, $C_{1-6}$ alkoxyphenyl-substituted $C_{1-6}$ alkoxy, tri($C_{1-6}$ alkylsiloxy)$C_{1-6}$ alkyl, $C_{1-6}$ alkyldiphenylsiloxy $C_{1-6}$ alkyl, triphenylsiloxy $C_{1-6}$ alkyl, tri($C_{1-6}$ alkyl)siloxy, $C_{1-6}$ alkyldiphenylsiloxy, and triphenylsiloxy.

The $R^1$ of case (b) is phenyl having a substituent $R^5$ or naphthyl; and
the $R^2$ of case (b) is phenyl having a substituent $R^5$ or —C(O)NHR$^4$ where the $R^4$ is H, $C_{1-6}$ alkyl, or siloxybenzyl having a substituent $R^5$.

From the viewpoint of achieving a better anti-tumor effect, fibrosis resistance, or hepatocyte differentiation-inducing effect in accordance with an embodiment of the present invention, the above substituents $R^1$ and $R^2$ are preferably as follows.

The $R^1$ of case (a) is phenyl having a substituent $R^5$ where the $R^5$ is at least one substituent selected from the group consisting of H, halogen, nitro, amino, cyano, OH, $C_{1-6}$ alkyl, $C_{1-6}$ halogenoalkyl, $C_{1-6}$ hydroxyalkyl, $C_{1-6}$ alkylamino, $C_{1-6}$ alkoxy, $C_{1-6}$ halogenoalkoxy, $C_{1-6}$ hydroxyalkoxy, and $C_{1-6}$ alkoxyamino.

The $R^2$ of case (a) is —C(O)NH(CH$_2$C$_6$H$_5$).

The $R^1$ of case (b) is naphthyl.

The $R^2$ of case (b) is nitrophenyl or —C(O)NHR$^4$ where the $R^4$ is H or siloxybenzyl having a substituent $R^5$.

From the viewpoint of achieving a much better anti-tumor effect, fibrosis resistance, or hepatocyte differentiation-inducing effect in accordance with an embodiment of the present invention, the above substituents $R^1$ and $R^2$ are preferably as follows.

The $R^1$ of case (a) is phenyl having at least one substituent selected from the group consisting of F, Cl, nitro, OH, and methoxy.

The $R^2$ of case (a) is —C(O)NH(CH$_2$C$_6$H$_5$).

The $R^1$ of case (b) is naphthyl.

The $R^2$ of case (b) is —C(O)NH$_2$, nitrophenyl, or (tert-butyldimethylsiloxy)benzyl.

From the viewpoint of exerting a more potent anti-tumor effect by using a lower concentration than that of IC-2 in accordance with an embodiment of the present invention, it is preferable that (i) the $R^1$ is phenyl having Cl at position 2 and 3 and the $R^2$ is —C(O)NH(CH$_2$C$_6$H$_5$); or (ii) the $R^1$ is naphthyl and the $R^2$ is —C(O)NHR$^4$ where the $R^4$ is benzyl having tert-butyldimethylsiloxy at position 4 or benzyl having Cl at position 4. In the below-described Examples, IC-2-506-1, IC-2-OTBS, and IC-2-Cl exerted a more potent anti-tumor effect when the concentration thereof is even lower than that of IC-2.

From the viewpoint of having a lower IC50 than that of IC-2 in accordance with an embodiment of the present invention, it is preferable that (i) the $R^1$ is phenyl having Cl at positions 2 and 3, phenyl having Cl at positions 2 and 4, or phenyl having Cl at positions 3 and 4 and the $R^2$ is —C(O)NH(CH$_2$C$_6$H$_5$); or (ii) the $R^1$ is naphthyl and the $R^2$ is —C(O)NHR$^4$ where the $R^4$ is benzyl having tert-butyldimethylsiloxy at position 4, benzyl having F at position 4, benzyl having Cl at position 4, or benzyl having methoxymethoxy at position 4. In the below-described Examples, IC-2-506-1, IC-2-506-2, IC-2-506-3, IC-2-OTBS, IC-2-F, IC-2-Cl, and IC-2-OMOM had a lower IC50 than IC-2.

From the viewpoint of exerting a more potent inhibitory effect on cancer stem cells than IC-2, it is preferable that the $R^1$ is naphthyl and the $R^2$ is benzyl having NO$_2$ at position 4, benzyl having (4-methoxyphenyl)methoxy at position 4, or benzyl having F at position 4. In the below-described Examples, IC-2-NO2, IC-2-OPMB, and IC-2-F exerted a more potent inhibitory effect on cancer stem cells than IC-2.

From the viewpoint of exerting an inhibitory effect on cancer stem cells by using a lower concentration than that of IC-2, it is preferable that (i) the $R^1$ is naphthyl and the $R^2$ is —C(O)NHR$^4$ where the $R^4$ is benzyl having tert-butyldimethylsiloxy at position 4. The present inventors demonstrated that IC-2-OTBS exerted an inhibitory effect on cancer stem cells when a concentration even lower than that of IC-2 was used in the below-described Examples.

From the viewpoint of exerting a more potent anti-fibrosis effect by using a lower concentration than that of IC-2, it is preferable that (i) the $R^1$ is phenyl having Cl at positions 3 and 4 and the $R^2$ is —C(O)NH(CH$_2$C$_6$H$_5$); or (ii) the $R^1$ is naphthyl and the $R^2$ is —C(O)NHR$^4$ where the $R^4$ is benzyl having tert-butyldimethylsiloxy at position 4 or benzyl having F at position 4. The present inventors demonstrated that IC-2-506-3, IC-2-OTBS, and IC-2-F exerted a more potent anti-fibrosis effect when a concentration even lower than that of IC-2 was used in the below-described Examples.

From the viewpoint of exerting an anti-fibrosis effect by using a lower concentration than that of IC-2 in accordance with an embodiment of the present invention, it is preferable that (i) the $R^1$ is naphthyl and the $R^2$ is —C(O)NHR$^4$ where the $R^4$ is benzyl having Cl at position 4. The present inventors demonstrated that IC-2-Cl exerted a more potent anti-fibrosis effect when a concentration even lower than that of IC-2 was used in the below-described Examples.

From the viewpoint of exerting a more potent anti-fibrosis effect by using an equal or higher concentration than that of IC-2 in accordance with an embodiment of the present invention, it is preferable that (i) the $R^1$ is phenyl having Cl at position 4, phenyl having Cl at positions 2 and 3, or phenyl having Cl at positions 3 and 4 and the $R^2$ is —C(O)NH(CH$_2$C$_6$H$_5$); or (ii) the $R^1$ is naphthyl and the $R^2$ is —C(O)NHR$^4$ where the $R^4$ is benzyl having OH at position 4. The present inventors demonstrated that IC-2-Ar—Cl, IC-2-506-1, IC-2-506-2, and IC-2-OH exerted a more potent anti-fibrosis effect when a concentration equal to or higher than that of IC-2 was used in the below-described Examples.

From the viewpoint of exerting a hepatocyte-inducing effect by using a low concentration in accordance with an embodiment of the present invention, it is preferable that the $R^1$ is naphthyl and the $R^2$ is —C(O)NHR$^4$ where the $R^4$ is benzyl having tert-butyldimethylsiloxy at position 4, benzyl having Cl at position 4, benzyl having F at position 4, or benzyl having (4-methoxyphenyl)methoxy at position 4. The present inventors demonstrated that IC-2-OTBS, IC-2-Cl, IC-2-F, and IC-2-OPMB exerted a hepatocyte-inducing effect by using a low concentration thereof in the below-described Examples.

From the viewpoint of exerting a more potent hepatocyte-inducing effect by using a higher concentration than that of IC-2 in accordance with an embodiment of the present invention, it is preferable that the $R^1$ is phenyl having Cl at positions 2 and 4 and the $R^2$ is —C(O)NH(CH$_2$C$_6$H$_5$). The present inventors demonstrated that IC-2-506-2 exerted a more potent hepatocyte-inducing effect when a concentration higher than that of IC-2 was used in the below-described Examples.

From the viewpoint of more strongly inhibiting a Wnt/β-catenin signaling pathway in liver cancer cells by using a concentration equal to or lower than that of IC-2 in accordance with an embodiment of the present invention, it is preferable that (i) the $R^1$ is phenyl having Cl at position 4 or phenyl having Cl at positions 2 and 3 and the $R^2$ is —C(O)NH(CH$_2$C$_6$H$_5$); or (ii) the $R^1$ is naphthyl and the $R^2$ is —C(O)NHR$^4$ where the $R^4$ is benzyl having Cl at position 4, benzyl having OMe at position 4, benzyl having F at position 4, or benzyl having OH at position 4, benzyl having NO$_2$ at position 4, benzyl having (4-methoxyphenyl)methoxy at position 4, or benzyl having methoxymethoxy at position 4. The present inventors demonstrated that IC-2-Ar—Cl, IC-2-506-1, IC-2-Cl, IC-2-OMe, IC-2-F, IC-2-OH, IC-2-NO2, IC-2-OPMB, and IC-2-OMOM exerted a more potent inhibitory effect on a Wnt/β-catenin signaling pathway in liver cancer cells when a concentration equal to or lower than that of IC-2 was used in the below-described Examples.

From the viewpoint of more strongly inhibiting a Wnt/β-catenin signaling pathway in liver stellate cells by using a concentration equal to or lower than that of IC-2 in accordance with an embodiment of the present invention, it is preferable that (i) the $R^1$ is phenyl having Cl at positions 2 and 3, phenyl having Cl at positions 2 and 4, or phenyl having Cl at positions 3 and 4 and the $R^2$ is —C(O)NH(CH$_2$C$_6$H$_5$); (ii) the $R^1$ is naphthyl and the $R^2$ is —C(O)NHR$^4$ where the $R^4$ is benzyl having Cl at position 4; or (iii) the $R^1$ is naphthyl and the $R^2$ is phenyl having NO$_2$ at position 2. The present inventors demonstrated that IC-2-506-1, IC-2-506-2, IC-2-506-3, IC-2-Cl, and 7c-NT exerted a more potent inhibitory effect on a Wnt/β-catenin signaling pathway in liver stellate cells when a concentration equal to or lower than that of IC-2 was used in the below-described Examples.

From the viewpoint of more strongly inhibiting a Wnt/β-catenin signaling pathway in mesenchymal stem cells by using a concentration equal to or lower than that of IC-2 in accordance with an embodiment of the present invention, it is preferable that (i) the $R^1$ is phenyl having Cl at position 4 or phenyl having NO$_2$ at position 4 and the $R^2$ is —C(O)NH(CH$_2$C$_6$H$_5$); or (ii) the $R^1$ is naphthyl and the $R^2$ is —C(O)NHR$^4$ where the $R^4$ is benzyl having NO$_2$ at position 4 or benzyl having (4-methoxyphenyl)methoxy at position 4. The present inventors demonstrated that IC-2-Ar—Cl, IC-2-Ar—NO2, IC-2-NO2, and IC-2-OPMB exerted a more potent inhibitory effect on a Wnt/β-catenin signaling pathway in mesenchymal stem cells when a concentration equal to or lower than that of IC-2 was used in the below-described Examples.

In formula (1) according to an embodiment of the present invention, the $R^1$ is naphthyl and the $R^2$ is —C(O)NHR$^4$ where the $R^4$ is benzyl having a substituent $R^6$ where the $R^6$ is at least one substituent selected from the group consisting of H, halogen, nitro, amino, cyano, OH, $C_{1-6}$ alkyl, $C_{1-6}$ halogenoalkyl, $C_{1-6}$ hydroxyalkyl, $C_{1-6}$ alkylamino, $C_{1-6}$ alkoxy, $C_{1-6}$ halogenoalkoxy, $C_{1-6}$ hydroxyalkoxy, $C_{1-6}$ alkoxyamino $C_{1-6}$ alkoxy-substituted $C_{1-6}$ alkoxy, $C_{1-6}$ alkoxyphenyl-substituted $C_{1-6}$ alkoxy, tri($C_{1-6}$ alkylsiloxy) $C_{1-6}$ alkyl, $C_{1-6}$ alkyldiphenylsiloxy $C_{1-6}$ alkyl, triphenylsiloxy $C_{1-6}$ alkyl, tri($C_{1-6}$ alkyl)siloxy, $C_{1-6}$ alkyldiphenylsiloxy, and triphenylsiloxy.

As used herein, the "halogen" includes F, Cl, Br, and I.

As used herein, unless otherwise indicated, the terms "alkyl" and "alkenyl" mean a linear or branched hydrocarbon chain.

As used herein, the term "$C_{1-6}$" refers to hydrocarbon containing 1, 2, 3, 4, 5, or 6 carbon atoms. That is, the term "$C_{1-6}$ alkyl" refers to alkyl containing 1, 2, 3, 4, 5, or 6 carbon atoms. Examples of $C_{1-6}$ alkyl include methyl, ethyl, n-propyl, isopropyl, n-butyl, isobutyl, sec-butyl, tert-butyl, n-pentyl, and n-hexyl. As used herein, the term "tri-$C_{1-6}$" includes mono-$C_{1-6}$ di-$C_{1-6}$, di-$C_{1-6}$ mono-$C_{1-6}$, and mono-$C_{1-6}$ mono-$C_{1-6}$ mono-$C_{1-6}$.

As used herein, examples of "alkenyl" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, and 5-hexenyl.

As used herein, examples of "alkoxy" include methoxy, ethoxy, propoxy, isopropoxy, butoxy, isobutoxy, sec-butoxy, tert-butxy, pentoxy, isopentoxy, and hexoxy.

As used herein, the term "optionally substituted" means that there is no substitution or 1, 2, 3, 4, or 5 substituents are included at a substitutable position(s). In addition, as used herein, the term "having a substituent(s)" means that, for example, 1, 2, 3, 4, 5, 6, 7, or 13 substituents (e.g., $R^1$ to $R^6$) may be included at a substitutable position(s) and the number of substituents may be between any two of them. Note that when a plurality of substituents are included, these substituents may be the same or different. In addition, regarding a compound according to an embodiment of the present invention, if the substitution position of a substituent is not specified or if the term "having a substituent(s)" is clearly indicated, the substituent position may be position 1, 2, 3, 4, 5, 6, 7, 8, or 9. Examples of each substituent include H, halogen, nitro, amino, cyano, OH, $C_{1-6}$ alkyl, $C_{1-6}$ halogenoalkyl, $C_{1-6}$ hydroxyalkyl, $C_{1-6}$ alkylamino, $C_{3-6}$ cycloalkyl, $C_{2-6}$ alkenyl, $C_{2-6}$ halogenoalkenyl, $C_{2-6}$ hydroxyalkenyl, $C_{2-6}$ alkenylamino, $C_{3-6}$ cycloalkenyl, $C_{2-6}$ alkynyl, $C_{2-6}$ halogenoalkynyl, $C_{2-6}$ hydroxyalkynyl, $C_{2-6}$ alkynylamino, $C_{1-6}$ alkoxy, $C_{1-6}$ halogenoalkoxy, $C_{1-6}$ hydroxyalkoxy, $C_{1-6}$ alkoxyamino, $C_{1-6}$ alkoxyphenyl, trialkylsiloxy, alkyldiphenylsiloxy, aryl, heteroaryl, $C_{1-6}$ alkoxy-substituted $C_{1-6}$ alkoxy, $C_{1-6}$ alkoxyphenyl-substituted $C_{1-6}$ alkoxy, tri($C_{1-6}$ alkylsiloxy)$C_{1-6}$ alkyl, $C_{1-6}$ alkyldiphenylsiloxy $C_{1-6}$ alkyl, triphenylsiloxy $C_{1-6}$ alkyl, tri($C_{1-6}$ alkyl)siloxy, $C_{1-6}$ alkyldiphenylsiloxy, and triphenylsiloxy.

As used herein, the "$C_{1-6}$ halogenoalkyl" refers to $C_{1-6}$ alkyl that is substituted by one or more halogens. The number of halogens may be, for example, 1, 2, 3, 4, 5, 6, or 13. Also, the number may be between any two of the numbers indicated above. In addition, when two or more halogens are included, the kind of each halogen may be the same or different. Examples of $C_{1-6}$ halogenoalkyl include, chloromethyl, dichloromethyl, trichloromethyl, fluoromethyl, difluoromethyl, trifluoromethyl, bromomethyl, dibromomethyl, tribromomethyl, chloroethyl, dichloroethyl, trichloroethyl, fluoroethyl, difluoroethyl, and trifluoroehtyl.

As used herein, the "$C_{1-6}$ hydroxyalkyl" refers to $C_{1-6}$ alkyl that is substituted by one or more hydroxy groups. The number of the hydroxy groups may be, for example, 1, 2, 3, 4, 5, 6, or 13. Also, the number may be between any two of the numbers indicated above. Examples of $C_{1-6}$ hydroxyalkyl include hydroxymethyl, 1-hydroxyethyl, 2-hydroxyethyl, 2-hydroxy-n-propyl, and 2,3-dihydroxy-n-propyl.

As used herein, the "$C_{1-6}$ alkylamino" refers to $C_{1-6}$ alkyl that is substituted by one or more amino groups. The number of the amino groups may be, for example, 1, 2, 3, 4, 5, 6, or 13. Also, the number may be between any two of the numbers indicated above. Examples of $C_{1-6}$ alkylamino include methylamino and ethylamino.

As used herein, the "$C_{1-6}$ halogenoalkoxy" is equivalent to $C_{1-6}$ halogenoalkyl, the alkyl of which is replaced by alkoxy. Examples of $C_{1-6}$ halogenoalkoxy include fluoromethoxy, difluoromethoxy, trifluoromethoxy, 1-fluoroethoxy, 2-fluoroethoxy, 2-chloroethoxy, 2-bromoethoxy, (1,1-difluoro)ethoxy, (1,2-difluoro)ethoxy, (2,2,2-trifluoro)ethoxy, (1,1,2,2-tetrafluoro)ethoxy, (1,1,2,2,2-pentafluoro)ethoxy, 1-fluoron-n-propoxy, 1,1-difluoro-n-propoxy, 2,2-difluoro-n-propoxy, 3-fluoro-n-propoxy, (3,3,3-trifluoro)-n-propoxy, (2,2,3,3,3-pentafluoro)-n-propoxy, 4-fluoro-n-butoxy, (4,4,4-trifluoro)-n-butoxy, 5-fluoro-n-pentyloxy, (5,5,5-trifluoro)-n-pentyloxy, 6-fluoro-n-hexyloxy, (6,6,6-trifluoro)-n-hexyloxy, 2-fluorocyclopropoxy, and 2-fluorocyclobutoxy.

As used herein, the "$C_{1-6}$ hydroxyalkoxy" is equivalent to $C_{1-6}$ hydroxyalkyl, the alkyl of which is replaced by alkoxy. Examples of $C_{1-6}$ hydroxyalkoxy include 2-hydroxyethoxy, 2-hydroxy-n-propoxy, 3-hydroxy-n-propoxy, 2,3-dihydroxy-n-propoxy, and 2-hydroxycyclopropyl.

As used herein, the "$C_{1-6}$ alkoxyamino" is equivalent to $C_{1-6}$ alkylamino, the alkyl of which is replaced by alkoxy. Examples of $C_{1-6}$ alkoxyamino include methoxyamino and ethoxyamino.

As used herein, the term "aryl" refers to a $C_{6-14}$ monocyclic, dicyclic, or tricyclic aromatic hydrocarbon ring group. Examples of the aryl include phenyl, naphthyl (e.g., 1-naphthyl, 2-naphthyl), benzyl, tetrahydronaphthalenyl, indenyl, and fluorenyl. From the viewpoint of achieving, in particular, an excellent anti-tumor effect, anti-fibrosis effect, and hepatocyte differentiation-inducing effect, preferred is naphthyl, phenyl, or benzyl. Also, the aryl includes a ring group that is condensed with $C_{5-8}$ cycloalkene at its double bond position.

As used herein, the "heteroaryl" includes groups having 5 to 14 ring atoms within their rings, having a shared 7C electron system, and having 1 to 4 heteroatoms selected from the group consisting of N, S, and O. Examples of heteroaryl include thienyl, benzothienyl, furyl, benzofuryl, dibenzofuryl, pyrrolyl, imidazolyl, pyrazolyl, pyridyl, pyrazinyl, pyrimidinyl, pyridazinyl, tetrazolyl, oxazolyl, thiazolyl, and isooxazolyl.

As used herein, examples of the "salt" include, but are not particularly limited to, anionic salts that are formed by using any acidic group (e.g., carboxyl) and cationic salts that are formed by using any basic group (e.g., amino). Examples of the salts include inorganic salts, organic salts, and salts disclosed in the article (Berge, Bighley, and Monkhouse, J. Pharm. Sci., 1977, 66, 1-19). The examples further include metal salts, ammonium salts, salts of an organic base, salts of an inorganic acid, salts of an organic acid, and salts of a basic or acidic amino acid. Examples of the metal salts include alkali metal salts (e.g., sodium salts, potassium salts), alkali earth metal salts (e.g., calcium salts, magnesium salts, barium salts), and aluminum salts. Examples of the salts of an organic base include salts of trimethylamine, triethylamine, pyridine, picoline, 2,6-lutidine, ethanolamine, diethanolamine, triethanolamine, cyclohexylamine, dicyclohexylamine, or N,N'-dibenzylethylenediamine. Examples of the salts of an inorganic acid include salts of hydrochloric acid, hydrobromic acid, nitric acid, sulfuric acid, or phosphoric acid. Examples of the salts of an organic acid include salts of formic acid, acetic acid, trifluoro acetic acid, phthalic acid, fumaric acid, oxalic acid, tartaric acid, maleic acid, citric acid, succinic acid, malic acid, methanesulfonic acid, benzenesulfonic acid, or p-toluenesulfonic acid. Examples of the salts of a basic amino acid include salts of arginine, lysine, or ornithine. Examples of the salts of an acidic amino acid include salts of aspartic acid or glutamic acid.

As use herein, the term "solvate" refers to a compound formed by using a solute and a solvent. J. Honig et al., The Van Nostrand Chemist's Dictionary P650 (1953) can be consulted regarding the solvate. If the solvent is water, the solvate formed is a hydrate. Preferably, the solvent does not interfere with the biological activity of the solute. Examples of such a preferable solvent include, but are not limited to, water, ethanol, and acetic acid. The most preferred solvent is water. A compound or a salt thereof according to an embodiment of the present invention absorbs moisture when contacting the air or recrystallized. They may have hygroscopic moisture or become a hydrate. As used herein, the term "isomer" includes a molecule, the molecular formula of which is identical, but the structure of which is different. Examples of the isomer include enantiomers, geometric (cis/trans) isomers, and isomers (diastereomers) having one or more chiral centers that are not mirror images of one another. As used herein, the term "prodrug" includes a precursor compound in which when the above compound is administered to a subject, a chemical change occurs due to metabolic processes or various chemical reactions to give rise to a compound, a salt thereof, or a solvate thereof according to the present invention. With regard to the prodrug, the article (T. Higuchi and V. Stella, "Pro-Drugs as Novel Delivery Systems", A.C.S. Symposium Series, Volume 14) can be referred to.

As used herein, examples of a "malignant tumor" include tumors caused by a mutation in a normal cell. The malignant tumors occur in all the organs and tissues in the body. The malignant tumor is, for example, at least one kind selected from the group consisting of lung cancer, esophagus cancer, gastric cancer, liver cancer, pancreatic cancer, renal cancer, adrenal cancer, biliary tract cancer, breast cancer, colon cancer, small intestinal cancer, ovarian cancer, uterine cancer, bladder cancer, prostate cancer, ureteral cancer, renal pelvis cancer, ureteral cancer, penile cancer, testicular cancer, brain tumor, cancer in central nervous system, cancer in peripheral nervous system, head and neck carcinoma, glioma, glioblastoma multiforme, skin cancer, melanoma, thyroid cancer, salivary gland cancer, malignant lymphoma, carcinoma, sarcoma, and hematological malignancies. The above liver cancer may be, for example, an epithelial tumor or nonepithelial tumor, and may be hepatocyte carcinoma or cholangiocellular carcinoma. Examples of the above skin cancer include basal cell carcinoma, squamous cell carcinoma, and malignant melanoma.

Recently, the presence of a cancer stem cell has been elucidated in the research field of malignant tumors. The cancer stem cell is considered to differentiate into cancer cells. In some patients, cancer may relapse after cancer cells have been removed and a certain period has then passed. This seems to be due to a very small number of surviving cancer stem cells. This cancer stem cell is characterized in that many conventional anti-cancer drugs are ineffective. With regard to this point, Prof. Nakayama of Kyushu Univ. has reported the research results in which when Fbxw7-deficient model mice were treated with imatinib (anti-cancer drug), cancer stem cells were killed (Takeishi et al., Cancer Cell. 2013 Mar. 18; 23(3): 347-61). In this connection, however, no compound has been obtained that directly inhibits proliferation of a cancer stem cell.

As used herein, the term "cancer stem cell" includes a cell that generates cancer cells. This cancer stem cell includes a cell expressing a cancer stem cell marker. Examples of the cancer stem cell marker include CD44, CD90, CD133, and EpCAM.

The "fibrosis" has been known as a symptom caused by loss of normal function due to tissue sclerosis in which the volume of a connective tissue mass including tissue components such as collagen is increased and a normal tissue is replaced by the connective tissue. Fibrosis occurs in, for example, respective tissues such as the liver, lung, kidney, heart, and skin. Also, occurrence of a large amount of fibrosis in a hepatic tissue, for example, may result in hepatic cirrhosis, leading to liver cancer. Each tissue, other than a liver tissue, may harbor a malignant tumor while fibrosis progresses. The term "fibrosis" include a disease accompanied by fibrosis. Examples of the disease accompanied by fibrosis include the above tissue fibrosis, cirrhosis, and malignant tumors accompanied by fibrosis.

As used herein, the term "treatment" includes exerting a prophylactic effect, an inhibitory effect, or a symptom-improving effect on a disease of a patient or on one or more symptoms involving the disease. As used herein, the "therapeutic drug" may be a pharmaceutical composition containing an active ingredient and at least one pharmacologically acceptable carrier. The pharmaceutical composition can be produced by any process known in the art of drug formulation. Examples of the process include: mixing an active ingredient with the above carrier. In addition, the dosage form of the drug is not limited as long as the drug can be used for treatment. The drug may be an active ingredient alone or a mixture of an active ingredient and any component. Further, examples of the dosage form of the above carrier include, but are not particularly limited to, a solid and liquid (e.g., a buffer). Note that examples of a therapeutic drug for malignant tumors include: a drug (prophylactic) used for preventing a malignant tumor; a drug for inhibiting relapse of a malignant tumor; and a drug for inhibiting proliferation of a malignant tumor cell. Examples of a therapeutic drug for cancer stem cells include: an agent for treating a cancer stem cell as a target; a therapeutic drug for malignant tumors derived from a cancer stem cell; and an inhibitor for cancer stem cells.

A drug administration route effective in treatment is preferably used. Examples of the administration route include intravenous, subcutaneous, intramuscular, intraperitoneal, and oral administration. Examples of the dosage form may include an injection, a capsule, a tablet, and granules. In addition, an aqueous solution for an injection may be combined with, for example, a saline solution, sugar (e.g., trehalose), NaCl, or NaOH. Further, the drug may be formulated with, for example, a buffer (e.g., a phosphate buffer) and/or a stabilizer.

A dosage is not particularly limited, and may be, for example, 0.001, 0.01, 0.1, 1, 4, 5, 10, 20, 50, 100, or 1000 mg/kg body weight per administration. The dosage may be between any two of the above values. An administration interval is not particularly limited, and the drug may be dosed, for example, once or twice per 1, 7, 14, 21, or 28 days. The drug may be dosed once or twice per period between any two of the above values. In addition, the dosage, the administration interval, and the administration method can be appropriately selected depending on the age, body weight, symptom, affected organ, etc., of a patient. Further, the drug preferably contains a therapeutically effective amount or a dose, which is effective in exerting a desired effect, of an active ingredient.

The effect of treating malignant tumors may be evaluated by imaging, endoscopic examination, biopsy, or detection of a malignant tumor marker. In addition, the effect of treating cancer stem cells may be evaluated by imaging, endoscopic examination, biopsy, or detection of a cancer stem cell marker. In addition, the effect of treating fibrosis may be evaluated by imaging, endoscopic examination, biopsy, or detection of a fibrosis marker. One may make such a judgment that when the level of a marker in a patient or a patient-derived sample (e.g., a tissue, cells, a cell population, or blood) is significantly decreased after administration of a therapeutic drug, there is a therapeutic effect. At this time, the level of a marker after administration of a therapeutic drug may be 0.7, 0.5, 0.3, or 0.1 times the level before the administration (or of a control). Alternatively, one may make such a judgment that when the number of marker-positive cells in the patient-derived sample is significantly decreased after administration of the therapeutic drug, there is a therapeutic effect. At this time, the number of marker-positive cells after administration of the therapeutic drug may be 0.7, 0.5, 0.3, or 0.1 times the number before the administration (or of a control). Note that in Example 6 below, the therapeutic effect was evaluated using mice in which CD44-positive HuH-7 cells had been subcutaneously transplanted. The present inventors also replaced the above CD44-positive HuH-7 cells by unsorted HuH-7 cells. This experiment has demonstrated that IC-2 exhibits an effect of treating a malignant tumor.

In addition, with regard to the therapeutic effect of treating a malignant tumor, one may make such a judgment that when the growth rate of patient-derived test cells is significantly decreased after administration of the therapeutic drug, there is a therapeutic effect. At this time, the growth rate of patient-derived test cells after administration of the therapeutic drug may be reduced to 0.7, 0.5, 0.3, or 0.1 times of the rate before the administration (or of a control). In addition, as used herein, the term "significantly" may include a case of $p<0.05$ or $p<0.01$ when Student's t test (one-sided or two-sided), for example, is used to evaluate a statistically significant difference. Also, the term may include a state in which there is a substantial difference.

As used herein, examples of the "patient" include human and non-human mammals (e.g., at least one of a mouse, guinea pig, hamster, rat, mouse, rabbit, pig, sheep, goat, cow, horse, cat, dog, marmoset, monkey, and chimpanzee). Meanwhile, the patient may be a patient who is determined or diagnosed as having the onset of a malignant tumor or fibrosis. In addition, the patient may be a patient who needs treatment of a malignant tumor or fibrosis. Also, the patient may be a patient who is determined or diagnosed as having a significantly larger number of cancer stem cells in a tissue than healthy individuals. Note that the determination or diagnosis may be performed by imaging, endoscopic examination, biopsy, or detection of various markers.

As used herein, the wording "a state in which cell proliferation is inhibited" includes a state in which the growth rate of test cells is significantly less than that before drug treatment. The growth rate can be evaluated by measuring the level of proliferation of cells during a given period of time. The level of proliferation may be measured, for example, visually or by using absorbance as an index. Alternatively, the level of proliferation may be measured by using, as an index, the level of a malignant tumor marker in a patient or a patient-derived sample. As used herein, the wording "inhibiting a cancer stem cell" includes, for example, inhibiting proliferation of a cancer stem cell and inhibiting the function of a cancer stem cell (e.g., inhibiting sphere formation, inhibiting marker expression).

An embodiment of the present invention provides a malignant tumor, cancer stem cell, or fibrosis marker inhibitor comprising a compound represented by formula (1), a salt thereof, or a solvate thereof. An embodiment of the present invention provides an inhibitor for sphere formation of malignant tumor cells or cancer stem cells, comprising a compound represented by formula (1), a salt thereof, or a solvate thereof. This sphere formation inhibitor may be used for treatment of malignant tumors or cancer stem cells.

An embodiment of the present invention provides a treatment method comprising the step of administering, to a patient, a compound represented by formula (1), a salt thereof, or a solvate thereof. An embodiment of the present invention provides use of a compound represented by formula (1), a salt thereof, or a solvate thereof in the manufacture of a therapeutic drug. An embodiment of the present invention provides a method for inhibiting growth of a malignant tumor cell or a cancer stem cell, comprising the step of administering, to a patient, a compound represented by formula (1), a salt thereof, or a solvate thereof. An embodiment of the present invention provides use of a compound represented by formula (1), a salt thereof, or a solvate thereof in the manufacture of a therapeutic drug for inhibiting growth of a malignant tumor cell or a cancer stem cell.

An embodiment of the present invention provides a method for inhibiting relapse of a malignant tumor, comprising the step of administering, to a patient, a compound represented by formula (1), a salt thereof, or a solvate thereof. An embodiment of the present invention provides use of a compound represented by formula (1), a salt thereof, or a solvate thereof in the manufacture of a malignant tumor relapse inhibitor.

An embodiment of the present invention provides an inhibitor for a Wnt/β-catenin signaling pathway, comprising a compound represented by formula (1), a salt thereof, or a solvate thereof. This inhibitor may be used to inhibit a Wnt/β-catenin signaling pathway. This inhibitor may be used for treatment of a disease ameliorated by an inhibitory effect on a Wnt/β-catenin signaling pathway.

An embodiment of the present invention provides a therapeutic drug for a malignant tumor, comprising a compound represented by formula (2), a salt thereof, or a solvate thereof (hereinafter, sometimes referred to as the "compound, etc., represented by formula (2)"), wherein the therapeutic drug is used in combination therapy using 5-FU (5-fluorouracil) and the compound, etc., represented by formula (2). In addition, an embodiment of the present invention provides a 5-FU-containing therapeutic drug for a malignant tumor, wherein the therapeutic drug is used in combination therapy using 5-FU and a compound represented by formula (2), a salt thereof, or a solvate thereof.

In this case, the wording "used in combination therapy" means that the compound, etc., represented by formula (2) and 5-FU may be administered simultaneously or separately. In addition, the wording "used in combination therapy" means that the compound, etc., represented by formula (2) and 5-FU may be administered as a combination. Also, regarding the dosing order, the compound, etc., represented by formula (2) may be first administered or 5-FU may be first administered. In addition, an embodiment of the present invention provides a combination for treating a malignant tumor, comprising 5-FU and a compound, etc., represented by formula (2). In addition, an embodiment of the present invention provides a method for treating a malignant tumor, comprising the step of administering, to a patient, 5-FU and a compound, etc., represented by formula (2). In this case, the patient may be a patient who has already received the compound, etc., represented by formula (2) or 5-FU. In addition, an embodiment of the present invention provides use of an anti-malignant tumor therapeutic drug comprising a compound, etc., represented by formula (2), wherein the therapeutic drug is used in combination therapy using 5-FU and the compound, etc., represented by formula (2). The therapeutic drug, combination, or treatment method may be used to exert a synergistic anti-tumor effect obtained by using 5-FU and, for example, the compound, etc., represented by formula (2). For instance, use of the compound, etc., represented by formula (2) alone at a low concentration may not exert a significant therapeutic effect. However, even in this case, when 5-FU is administered in combination, it gives a higher therapeutic effect than when 5-FU is used singly. Also, when the compound, etc., represented by formula (2), in a low concentration at which the compound, etc., alone does not exhibit a significant therapeutic effect and 5-FU in a low concentration at which 5-FU alone does not exhibit a significant therapeutic effect are administered in combination, it exerts a significant therapeutic effect. Note that as used herein, the term "low concentration" means that the single dose may be, for example, 0.001, 0.01, 0.1, 1, 2, 3, 4, 5, 10, 15, or 20 mg/kg body weight and the dose may be between any two of them.

As used herein, the substituents $R^7$ and $R^8$ of formula (2) are the same or different and each represent optionally substituted $C_{1-6}$ alkyl or optionally substituted $C_{2-6}$ alkenyl. From the viewpoint of achieving an excellent anti-tumor effect in accordance with an embodiment of the present invention, the above substituents $R^7$ and $R^8$ are the same or different and each represent $C_{1-6}$ alkyl. From the viewpoint of achieving a better anti-tumor effect, it is more preferable that the above substituents $R^7$ and $R^8$ are the same or different and each represent $C_{1-3}$ alkyl. In addition, from the viewpoint of achieving a much better anti-tumor effect, it is still more preferable that the above substituents $R^7$ and $R^8$ are methyl.

Any of the method may further comprises a step of detecting a malignant tumor marker, a cancer stem cell marker, a fibrosis marker, or a hepatocyte marker. Any of the above drugs or methods is applicable in vitro or in vivo.

Any document and (patent or patent application) publication, which are cited herein, are incorporated by reference in its entirety.

As used herein, the term "or" may be used when "at least one" matter listed in the text of specification can be employed. The same applies to the term "or". As used herein, when the wording "between any two of the above values" is indicated, the two values are inclusive in the range. As used herein, the phrase "from A to B" means "A or more and B or less".

As described above, the embodiments of the present invention have been illustrated. These embodiments are examples of the present invention. Accordingly, various configurations other than the above embodiments can be adopted. In addition, combinations among the above-described embodiments can also be employed.

EXAMPLES

Hereinafter, the present invention is further illustrated by referring to Examples. The present invention, however, is not limited to them.

<Example 1> Compound Synthesis

Compounds were synthesized in accordance with the schemes shown in FIGS. 1 to 9. The details of the synthesis were illustrated below. FIGS. 10 to 14 show data on the structural formula and spectrum of each compound synthesized.

Compound 1

First, 1-naphtaldehyde (1.6 g, 10 mmol) and 2,2-dietoxyethanamine (1.3 g, 10 mmol) were mixed, and the mixture was stirred at 100° C. for from 30 min to 1 h. After allowed to cool, the reaction mixture was mixed with EtOH (25 mL), and the resulting mixture was stirred and made homogeneous. Next, a small amount of $NaBH_4$ (0.38 g, 10 mmol) was gradually added and the mixture was then stirred at room temperature for from 1 h to overnight. After completion of the reaction, EtOH was distilled away while the mixture was concentrated under reduced pressure. (An appropriate amount of) Water was added to the resulting residue, and a product was extracted with AcOEt. A separated organic layer was washed with saturated saline and dried with $Na_2SO_4$. After that, the sample was filtered and concentrated under reduced pressure. The resulting residue was purified by silica gel column chromatography (AcOEt/hexane=5/1) to yield compound 1 (2.3 g, 8.5 mmol, 85%) as colorless transparent liquid.

Compound 2b

HATU (0.76 g, 2.0 mmol) and diisopropylethylamine (DIEA) (0.26 g, 2.0 mmol) were added to a dry-DMF solution (7 mL) containing Fmoc-L-Phe-OH (0.54 g, 2.0 mmol), and the mixture was stirred at room temperature for 30 min. The compound 1 (0.54 g, 2.0 mmol) was added to the reaction mixture and then stirred overnight at room temperature. After completion of the reaction, water (20 mL) was added. Then, a product was extracted with AcOEt. A separated organic layer was washed twice with saturated saline and dried with $Na_2SO_4$. After that, the sample was filtered and concentrated under reduced pressure. The resulting residue was purified by silica gel column chromatography (AcOEt/hexane=1/2) to yield compound 2b (1.2 g, 1.9 mmol, 95%) as a colorless solid.

Compound 3b

Diethylamine (DEA) (10 mL) was added to a $CH_2Cl_2$ solution (20 mL) containing the compound 2b (1.1 g, 1.7 mmol), and the mixture was stirred at room temperature for 3 h. After completion of the reaction, $CH_2Cl_2$ and excessive DEA were distilled away while the mixture was concentrated under reduced pressure. The resulting residue was purified by silica gel column chromatography (AcOEt/EtOH=5/1) to yield compound 3b (0.55 g, 1.3 mmol, 76%) as colorless, transparent, viscous liquid.

Compound 4b

HATU (3.3 g, 8.7 mmol) and DIEA (1.1 g, 8.5 mmol) were added to a dry-DMF solution (15 mL) containing Fmoc-β-Ala-OH (2.5 g, 8.0 mmol), and the mixture was stirred at room temperature for 30 min. The compound 3b (3.3 g, 7.8 mmol) was added to the reaction mixture and then stirred overnight at room temperature. After completion of the reaction, water (30 mL) was added. Then, a product was extracted with AcOEt. A separated organic layer was washed twice with saturated saline and dried with $Na_2SO_4$. After that, the sample was filtered and concentrated under reduced pressure. The resulting residue was purified by silica gel column chromatography (AcOEt/hexane=3/1) to yield compound 4b (5.1 g, 7.1 mmol, 91%) as a colorless solid.

Compound 6b

DEA (6 mL) was added to a $CH_2Cl_2$ solution (10 mL) containing the compound 4b (2.8 g, 3.9 mmol), and the mixture was stirred at room temperature for from 3 to 4 h. $CH_2Cl_2$ and excessive DEA were distilled away while the mixture was concentrated under reduced pressure. (An appropriate amount of) $CH_2Cl_2$ was added to the resulting residue and the mixture was made a homogeneous solution. After that, the sample was again concentrated under reduced pressure. After this protocol was repeated twice, $CH_2Cl_2$ (10 mL) was added to the resulting residue. The mixture was stirred and made homogeneous. Then, benzyl isocyanate (0.78 g, 5.9 mmol) was added and the resulting mixture was stirred overnight at room temperature. After completion of the reaction, $CH_2Cl_2$ was distilled away while the mixture was concentrated under reduced pressure. The resulting residue was purified by silica gel column chromatography (AcOEt/EtOH=30/1) to yield compound 6b (1.5 g, 2.4 mmol, 62%) as a colorless solid.

Compound 8b

Formic acid (10 mL) was added to the compound 4b (1.6 g, 2.3 mmol), and the mixture was stirred overnight at room temperature. After completion of the reaction, formic acid was distilled away while the mixture was concentrated under reduced pressure. The resulting residue was purified by silica gel column chromatography (AcOEt/hexane=4/1) to yield compound 8b (1.3 g, 2.1 mmol, 91%) as a colorless solid.

Compound 9b

Diethylamine (1.3 g, 18 mmol, 1.8 mL) was added to a $CH_2Cl_2$ solution (5.5 mL) containing the compound 8b (1.1 g, 1.8 mmol), and the mixture was stirred at room temperature for 3 h. After completion of the reaction, $CH_2Cl_2$ was distilled away while the mixture was concentrated under reduced pressure. The resulting residue was purified by silica gel column chromatography (AcOEt/EtOH=7/1) to yield compound 9b (0.57 g, 1.4 mmol, 78%) as a colorless solid.

Compound IC-2 (Synthesized from Compound 6b)

Formic acid (8 mL, 0.21 mol) was added to the compound 6b (1.3 g, 2.1 mmol), and the mixture was stirred overnight at room temperature. After completion of the reaction, formic acid was distilled away while the mixture was concentrated under reduced pressure. The resulting residue was purified by silica gel column chromatography (AcOEt/EtOH=30/1) to yield IC-2 (1.0 g, 1.9 mmol, 90%) as a colorless solid.

Compound IC-2 (Synthesized from Compound 9b)

Benzyl isocyanate (1.4 g, 11 mmol) was added to a $CH_2Cl_2$ solution (10 mL) containing the compound 9b (3.3 g, 8.3 mmol), and the mixture was stirred overnight at room temperature. After completion of the reaction, $CH_2Cl_2$ was distilled away while the mixture was concentrated under reduced pressure. The resulting residue was purified by silica gel column chromatography (AcOEt/EtOH=30/1) to yield IC-2 (3.7 g, 6.9 mmol, 83%) as a colorless solid.

Compound 1-Ar—R (R=4-OMe, 4-Cl, 4-F, 4-$NO_2$, 2,3-$Cl_2$, 2,4-$Cl_2$, or 3,4-$Cl_2$)

The same synthesis protocol as for compound 1 was carried out except that instead of 1-naphtaldehyde, 4-substituted benzaldehyde (substituent R=OMe, Cl, F, $NO_2$), 2,3-substituted benzaldehyde (substituent R=Cl), 2,4-substituted benzaldehyde (substituent R=Cl), or 3,4-substituted benzaldehyde (substituent R=Cl) was used.

Compound 1-Ar-OBoc

First, 4-hydroxybenzaldehyde (1.9 g, 16 mmol) and 2,2-dietoxyethanamine (2.0 g, 15 mmol) were mixed, and the mixture was stirred at 100° C. for 1 h. After the mixture was allowed to cool, THF (30 mL) was added to the resulting reaction mixture under stirring to yield a homogeneous mixture. Then, 4-(dimethylamino)pyridine (DMAP) (0.55 g, 4.5 mmol) and di-tent-butyl dicarbonate ($Boc_2O$) (3.9 g, 18 mmol) were added thereto, and the resulting mixture was stirred at room temperature for 30 min. Subsequently, (an appropriate amount of) AcOEt was added to the reaction mixture, and an organic layer was washed twice with (an appropriate amount of) saturated $NH_4Cl$ aqueous solution and once with (an appropriate amount of) saturated saline, followed by drying with $Na_2SO_4$. After filtration and concentration under reduced pressure, EtOH (30 mL) was added to the resulting residue. The mixture was stirred and made homogeneous, and $NaBH_4$(0.43 g, 11 mmol) was then added portionwise. After that, the mixture was stirred at room temperature for 1 h. After completion of the reaction, the resulting mixture was concentrated under reduced pressure and EtOH was distilled away. Then, (an appropriate amount of) water was added to the resulting residue, and a product was extracted with AcOEt. A separated organic layer was washed with saturated saline, dried with $Na_2SO_4$, filtered, and concentrated under reduced pressure. The resulting residue was purified by silica gel column chromatography (AcOEt/hexane=3/1) to yield 1-Ar-OBoc (2.7 g, 8.0 mmol, 53%) as colorless, transparent liquid.

Compounds 2b-Ar—R and 2b-Ar-OBoc

The same synthesis protocol as for compound 2b was carried out except that instead of compound 1, compound 1-Ar—R (R=4-OMe, 4-Cl, 4-F, 4-$NO_2$, 2,3-$Cl_2$, 2,4-$Cl_2$, or 3,4-$Cl_2$) or compound 1-Ar-OBoc was used.

Compounds 3b-Ar—R and 3b-Ar-OBoc

The same synthesis protocol as for compound 3b was carried out except that instead of compound 2b, compound 2b-Ar—R or compound 2b-Ar-OBoc was used.

Compounds 4b-Ar—R and 4b-Ar-OBoc

The same synthesis protocol as for compound 4b was carried out except that instead of compound 3b, compound 3b-Ar—R or compound 3b-Ar-OBoc was used.

Compound 8b-Ar—R

The same synthesis protocol as for compound 8b was carried out except that instead of compound 4b, compound 4b-Ar—R was used.

Compound 9b-Ar—R

The same synthesis protocol as for compound 9b was carried out except that instead of compound 8b, compound 8b-Ar—R was used.

Compounds IC-2-Ar—R and IC-2-506-1 to -3

The same synthesis protocol as for compound IC-2 (synthesized from 9b) was carried out except that instead of compound 9b, compound 9b-Ar—R was used.

Compound 6b-Ar-OBoc

The same synthesis protocol as for compound 6b was carried out except that instead of compound 4b, compound 4b-Ar-OBoc was used.

Compound IC-2-Ar—OH

The same synthesis protocol as for compound IC-2 (synthesized from 6b) was carried out except that instead of compound 6b, compound 6b-Ar-OBoc was used.

Compound 6b-R (R=OMe, Cl, F)

The same synthesis protocol as for compound 6b was carried out except that instead of benzyl isocyanate, 4-substituted benzyl isocyanate (substituent R=OMe, Cl, or F) was used.

Compound IC-2-R

The same synthesis protocol as for compound IC-2 (synthesized from 6b) was carried out except that instead of compound 6b, 6b-R (R=OMe, Cl, F) was used.

IC-2-R (R=$NO_2$)

The same synthesis protocol as for IC-2 (synthesized from 9b) was carried out except that instead of benzyl isocyanate, 4-substituted benzyl isocyanate (substituent R=$NO_2$) was used.

4-(4-Methoxybenzyloxy)phenylacetic acid $K_2CO_3$ (4.4 g, 32 mmol) and 4-methoxybenzyl chloride (1.3 g, 8 mmol) were added to a dry-DMF solution (20 mL) containing methyl 4-hydroxyphenylacetate (2.7 g, 16 mmol), and the mixture was stirred at room temperature for 24 h. The reaction mixture was injected into ice-cold water (30 mL) and a product was then extracted with EtOAc. A separated organic layer was washed with saturated saline and dried with $Na_2SO_4$. After that, the sample was filtered and concentrated under reduced pressure. MeOH (24 mL) and THF (8 mL) were added to the resulting residue, and the mixture was stirred and made homogeneous. Next, a NaOH aqueous solution (0.96 g, 24 mmol, 6 mL) was slowly added, and the mixture was stirred at room temperature for 2 h. An organic solvent was distilled away while the mixture was concentrated under reduced pressure. Then, water (50 mL) was added and the mixture was made acidic with 1 M sulfuric acid. Subsequently, ethyl acetate and THF were used to extract a product. An organic layer was washed twice with saturated saline and dried with $Na_2SO_4$. After that, the sample was filtered and concentrated under reduced pressure. The resulting residue was recrystallized (using EtOAc-THF) to give pure 4-(4-methoxybenxyloxy)phenylacetic acid (1.8 g, 6.8 mmol, 85%).

4-Methoxymethoxyphenylacetic Acid

DIEA (3.9 g, 30 mmol) was added to a $CH_2Cl_2$ solution (15 mL) containing methyl 4-hydroxyphenylacetate (2.5 g, 15 mmol). While the mixture was cooled in an ice water bath, chloromethyl methyl ether (1.8 g, 23 mmol) was added. The mixture was stirred at that temperature for 10 min. Then, the temperature was returned to room temperature, and the mixture was further stirred overnight. $CH_2Cl_2$ and excessive chloromethyl methyl ether were removed while the mixture was concentrated under reduced pressure. After that, MeOH (25 mL) was added and the mixture was stirred and made homogeneous. Following that, a KOH aqueous solution (3.0 g, 45 mmol, 5 mL) was added, and the mixture was stirred at room temperature for 1.5 h. Water (20 mL) was added to the reaction mixture and an aqueous layer was separated. Thereafter, a saturated $NH_4Cl$ aqueous solution (20 mL) was added to adjust by using a diluted sulfuric acid a pH to about 4. EtOAc was then added thereto to separate an organic layer. After that, the organic layer was washed with saturated saline and dried with $Na_2SO_4$. The resulting sample was filtered, concentrated under reduced pressure, and dried under reduced pressure to give 4-methoxymethoxyphenylacetic acid (2.2 g, 11 mmol, 76%).

Benzyl 4-hydroxyphenylacetate

NaH (60% in oil, 0.88 g, 22 mmol) was added to a dry-DMF solution (20 mL) containing 4-hydroxyphenylacetic acid (3.0 g, 20 mmol) that was cooled under an Ar atmosphere in an ice water bath. The mixture was stirred at that temperature for 30 min. Next, benzyl bromide (6.8 g, 40 mmol) was added in several portions over 30 min. The mixture was stirred for 3 h while cooled in an ice water bath, and further stirred overnight at room temperature. Then, water (20 mL) and EtOAc (20 mL) were added to the reaction mixture and well stirred. After that, an organic layer was separated, washed with 5%-$NaHCO_3$ aqueous solution and saturated saline, and dried with $Na_2SO_4$. After the sample was filtered and concentrated under reduced pressure, hexane was added to the resulting solid. Subsequently, suction filtration was carried out and the resulting solid was dried under reduced pressure to give benzyl 4-hydroxyphenylacetate (3.4 g, 14 mmol, 70%).

4-(tert-Butyldimethylsiloxy)phenylacetic acid

To dry DMF solution (10 mL) containing benzyl 4-hydroxyphenylacetate (1.7 g, 7 mmol) were added tert-butyldimethylsilyl chloride (1.5 g, 9.8 mmol) and imidazole (1.1 g, 16.8 mmol). The mixture was stirred at room temperature for 2 h. Next, water (15 mL) and EtOAc (15 mL) were added to the reaction mixture. Then, an organic layer was separated, washed with saturated saline, dried with $Na_2SO_4$, filtered, and concentrated under reduced pressure. Subsequently, EtOH (15 mL) was added to the resulting reside, and the mixture was stirred to prepare a homogeneous solution. To this solution was added 5%-Pd/C (0.75 g). After that, the inside of the system was replaced by $H_2$. The mixture was stirred at room temperature for 4 h, and then filtered through two filter papers stacked to remove Pd/C. The resulting filtrate was concentrated under reduced pressure. The resulting residue was subjected to silica gel column chromatography (AcOEt/hexane=1/2) to yield 4-(tert-butyldimethylsiloxy)phenylacetic acid (0.78 g, 2.9 mmol, 42%).

4-(tert-Butyldimethylsiloxymethyl)phenylacetic acid

First, 4-hydroxymethylphenylacetic acid was used as a starting material, and the $CO_2H$ group was substituted by benzyl and the OH group was substituted by tert-butyldimethylsilyl by using a protocol similar to that in the case of benzyl 4-hydroxyphenylacetate and 4-(tert-butyldimethylsiloxy)phenylacetic acid. In this regard, however, a benzyl-substituted compound was not isolated. Silica gel column chromatography was conducted at AcOEt/hexane=1/2. The yield from 4-hydroxymethyl-phenylacetic acid was 34%.

Compound IC-2-OMOM

Diphenylphosphoryl azide (0.83 g, 3 mmol) and Et3N (0.36 g, 3.6 mmol) were added to a toluene solution (10 mL) containing 4-methoxymethoxyphenylacetic acid (0.59 g, 3 mmol), and the mixture was stirred at 80° C. for 2 h. After the mixture was allowed to cool, hexane (15 mL) was added and the mixture was stirred for a certain time. Next, a supernatant was collected by decantation. Hexane (7 mL) was again added to the residue, and the mixture was stirred for a certain time. Then, a supernatant was collected by decantation, and this operation was repeated one more time. The collected supernatant was concentrated under reduced pressure. After that, $CH_2Cl_2$ (8 mL) was added to the residue and the mixture was made homogeneous. Subsequently, compound 9b (0.40 g, 1 mmol) was added thereto. After the mixture was stirred overnight at room temperature, an organic solvent was distilled away while the mixture was concentrated under reduced pressure. The resulting residue was subject to silica gel column chromatography (AcOEt) to give IC-2-OMOM (0.50 g, 0.85 mmol, 84%).

Compound IC-2-NO2

The same protocol as for IC-2-OMOM and 4-nitrophenylacetic acid were used for the manipulation. In the protocol, however, the step of collecting a supernatant by adding hexane was omitted. After the sample was allowed to cool, $CH_2Cl_2$ and the compound 9b were added directly to the reaction mixture. Silica gel column chromatography was conducted at AcOEt/EtOH=8/1. The yield was 24%.

Compound IC-2-OPMB

The same protocol as for IC-2-OMOM and 4-(4-methoxybenzyloxy)phenylacetic acid were used for the manipulation. In this regard, however, addition of only toluene failed to convert 4-(4-methoxybenzyloxy)phenylacetic acid to a homogeneous solution. Thus, dry-THF (5 mL) was also added. Silica gel column chromatography was conducted at AcOEt/EtOH=30/1. The yield was 93%.

Compound IC-2-OTBS

The same protocol as for IC-2-OMOM was carried out except that 4-(tert-butyldimethylsiloxy)phenylacetic acid was used. Silica gel column chromatography was conducted by using AcOEt. The yield was 76%.

Compound IC-2-MOTBS

The same protocol as for IC-2-OMOM was carried out except that 4-(tert-butyldimethylsiloxymethyl)phenylacetic acid was used. Silica gel column chromatography was conducted by using AcOEt. The yield was 66%.

Compound 9b-CONH$_2$

To a CH$_2$Cl$_2$ (8 mL)-water (0.4 mL) solution containing IC-2-OPMB (0.27 g, 0.40 mmol) was added 2,3-dichloro-5,6-dicyano-1,4-benzoquinone (DDQ) (0.19 g, 0.84 mmol). The mixture was stirred overnight at room temperature. Next, 5% NaHCO$_3$ aqueous solution (10 mL) was added to the reaction mixture, and the resulting mixture was stirred for a while and a product was extracted with CH$_2$Cl$_2$. A separated organic layer was washed with saturated saline, dried with Na$_2$SO$_4$, filtered, and concentrated under reduced pressure. The resulting residue was purified by silica gel column chromatography (AcOEt/hexane=10/1) to yield 9b-CONH$_2$ (0.11 g, 0.25 mmol, 63%).

Compound IC-2-OH

A TBAF-containing THF solution (1 M, 1.4 mL, 1.4 mmol) was added, in an ice-cold water bath, to a dry THF solution (8 mL) containing IC-2-OTBS (0.46 g, 0.69 mmol). The mixture was stirred at that temperature for 30 min. Then, water (10 mL) was added to the reaction mixture, and a product was extracted with AcOEt. A separated organic layer was washed with saturated saline, dried with Na$_2$SO$_4$, filtered, and concentrated under reduced pressure. The resulting residue was purified by silica gel column chromatography (AcOEt/hexane=30/1) to yield IC-2-OH (0.35 g, 0.64 mmol, 93%).

Compound IC-2-MOH

The same protocol as for IC-2-OH was carried out except that IC-2-MOTBS was used. In this regard, however, a TBAF-containing THF solution was added; an ice-cold water bath was removed; the temperature was raised to room temperature; and then the mixture was stirred for 1.5 h. Silica gel column chromatography was conducted at AcOEt/EtOH=10/1. The yield was 71%.

Compound 6c-NT

To 5b (0.85 g, 1.7 mmol)-containing DMSO solution (8 mL) were added DIEA (0.50 g, 3.9 mmol) and 2-fluoronitrobenzene (0.37 g, 2.6 mmol). The mixture was stirred at room temperature for two overnights. Then, water (20 mL) was added to the reaction mixture, the mixture was stirred for a while, and a product was extracted with AcOEt. A separated organic layer was washed with saturated saline, dried with Na$_2$SO$_4$, filtered, and concentrated under reduced pressure. The resulting residue was purified by silica gel column chromatography (AcOEt/hexane=1/1) to yield 6c-NT (0.68 g, 1.1 mmol, 65%) as a yellow solid.

Compound 7c-NT

To 6c-NT (0.74 g, 1.2 mmol) was added formic acid (4.5 mL, 120 mmol). The mixture was stirred at room temperature for 1 h. After completion of the reaction, the resulting mixture was concentrated under reduced pressure and formic acid was distilled away. The resulting residue was purified by silica gel column chromatography (AcOEt/hexane=2/1) and then recrystallized (by using AcOEt-hexane) to yield 7c-NT (87 mg, 0.17 mmol, 14%) as a yellow needle crystal.

<Example 2> Anti-Tumor Effect 2.1 Examples of Reagents Used

DMEM: Dulbecco's Modified Eagle Medium 2 (Nissui Pharmaceutical CO., LTD., Tokyo): 2 mM L-glutamine, 0.2% NaHCO$_3$, 3500 mg/L D-glucose, 100 U/mL penicillin, 100 μg/mL streptomycin (Nacalai tesque, Kyoto), and 10% fetal bovine serum (FBS) (Sigma-Aldrich Corp., St. Louis, Mo.).
PBS(−): 8000 mg/L NaCl, 2900 mg/L Na$_2$HPO$_4$.12H$_2$O, 200 mg/L KCl, and 200 mg/L KH$_2$PO$_4$ (Nacalai tesque).
0.25% Trypsin/1 mM EDTA solution (Nacalai tesque).

2.2. Cell Culture

HuH-7 cells, a human liver cancer cell line, were cultured on 10-cm cell culture dishes (TPP Techno Plastic Products AG, Trasadingen, Switzerland) by using DMEM under conditions at 5% CO$_2$, 37° C., and 100% humidity. When the cells were 70 to 90% confluent, 200 μL of 0.25% Trypsin/1 mM EDTA solution, which had been prepared by diluting the stock solution 10-fold with PBS (−), was added to detach the cells. Then, the cells were centrifuged at 1000 rpm for 3 min at room temperature. The cells recovered were subcultured at a 1:4 split ratio.

A pTCF4-CMVpro-GL4.20 plasmid vector, which had been constructed by inserting 3 copies of TCF4 motifs (CCT TTG ATC) upstream of a CMV promoter into a multiple cloning site of pGL4.20 (Promega Corp., Fitchburg, Wis.), was linearized and stably transfected into the HuH-7 cells. The resulting stable cells (HuH7-TCF4 cells) and HuH-7 cells were likewise cultured.

2.3. Growth Inhibitory Effect on Cancer Cells (WST Assay)

First, 70 to 90% confluent HuH-7 cells were harvested and seeded (n=3) at 5×10$^3$ cells/well of a 96-well plate (TPP). After 24 h, each compound was added to the cells and the mixture was cultured at 37° C. The concentrations of each compound were 0, 10, 20, 30, 40, and 50 μM. For IC-2-506-1, however, the concentrations used were 0, 10, 20, 25, 30, 40, and 50 μM. Each control sample (0 μM) used was 0.1% DMSO, a solvent for each compound.

Next, 0, 24, 48, and 96 h after the compound treatment, 100 μL of DMEM-diluted 10% Cell Counting Kit-8 (DOJINDO LABORATORIES, Kumamoto) was added. The mixture was incubated at 37° C. for 60 min and its absorbance (at a measurement wavelength of 450 nm/control wavelength of 600 nm) was measured by using a Sunrise Rainbow RC (Tecan Group Ltd., Mannedorf, Switzerland). Absorbance for the cells alone was calculated by subtracting, from the reading obtained, absorbance for 10% Cell Counting Kit-8 alone.

Meanwhile, IC50 of each compound was calculated as $IC50=10^{\{LOG(A/B)\times(50-C)/(D-C)+LOG(B)\}}$ wherein A is a higher concentration which gives more than 50% inhibition; B is a lower concentration which gives less than 50% inhibition; C is the level of inhibition at the concentration B; and D is the level of inhibition at the concentration A. Note that a significant difference was evaluated by using (two-tailed) Student's t-test. The "*" in figures indicates a significant difference of $p<0.05$ between 0.1% DMSO and each compound; and the "**" indicates a significant difference of $p<0.01$ (the same applies to all the figures in Examples).

The results demonstrated that all the compounds exhibited a significant growth inhibitory effect over control (FIGS. 15 to 31). The IC50 of each compound was as follows. IC-2-Ar—Cl: 45.07 μM; IC-2-506-1: 14.10 μM; IC-2-506-2: 25.63 μM; IC-2-506-3: 18.32 μM; IC-2-OTBS: 11.76 μM; 7c-NT: 36.11 μM; IC-2-OMe: 34.89 μM; IC-2-F: 22.20 μM; IC-2-Cl: 14.37 μM; IC-2-NO2: 28.07 μM; IC-2-OPMB: 50 μM; IC-2-OMOM: 20.28 μM; IC-2-OH: 33.47 μM.

2.4. Inhibitory Effect on Cancer Stem Cells (FCM Analysis)

CD44, a cancer stem cell marker, was used as an indicator to examine an inhibitory effect of each compound on cancer stem cells. The concentrations of the respective compounds were as described in FIG. 32. Each control sample used was 0.1% DMSO, a solvent for each compound. In the figures, the "‡" indicates a significant difference of $p<0.01$.

First, 70 to 90% confluent HuH-7 cells were harvested and seeded at $1.5\times10^6$ cells per 10-cm cell culture dish. After 24 h, each compound was added to the cells and the mixture was cultured at 37° C. At 48 h after the compound treatment, the cells were harvested from each culture dish. The cells were centrifuged at 1000 rpm and at 4° C. for 3 min to remove a supernatant and were then washed twice with 1 mL of 0.5% FBS/2 mM EDTA/PBS. Next, the cells were suspended in 500 μL of 5% BSA/0.5% FBS/2 mM EDTA/PBS for blocking at 4° C. for 15 min. Then, 5 μL of a mouse anti-human CD44 monoclonal antibody (156-3C11, Cell Signaling Technology Inc., Danvers, Mass.) was added to 500 μL of the cell suspension. The mixture was resuspended and subjected to a primary antibody reaction in a dark room at 4° C. for 30 min. After that, the cells were washed 3 times with 1 mL of 0.5% FBS/2 mM EDTA/PBS. Subsequently, 100 μL of Alexa Fluor 488-labeled IgG (H+L) (ab150113, Abcam Ltd., Cambridge, UK), which had been diluted 200-fold with 5% BSA/0.5% FBS/2 mM EDTA/PBS, was added and the cells were suspended. Then, a secondary antibody reaction was carried out in a dark room at 4° C. for 30 min. After that, the cells were washed 3 times with 1 mL of 0.5% FBS/2 mM EDTA/PBS. Thereafter, the cells were suspended in 500 μL of 0.5% FBS/2 mM EDTA/PBS and were made to pass through a 40 μm-mesh column (Becton, Dickinson and Company, Franklin Lakes, N.J.). A Beckman Coulter-Moflo XDP (Beckman Coulter Inc., Fullerton, Calif.) was used for analysis. Following the analysis, further analysis was conducted by adding 2 μL of 0.25 mg/mL Propidium Iodide (PI). The same experiment was repeated four times.

Figure 32:
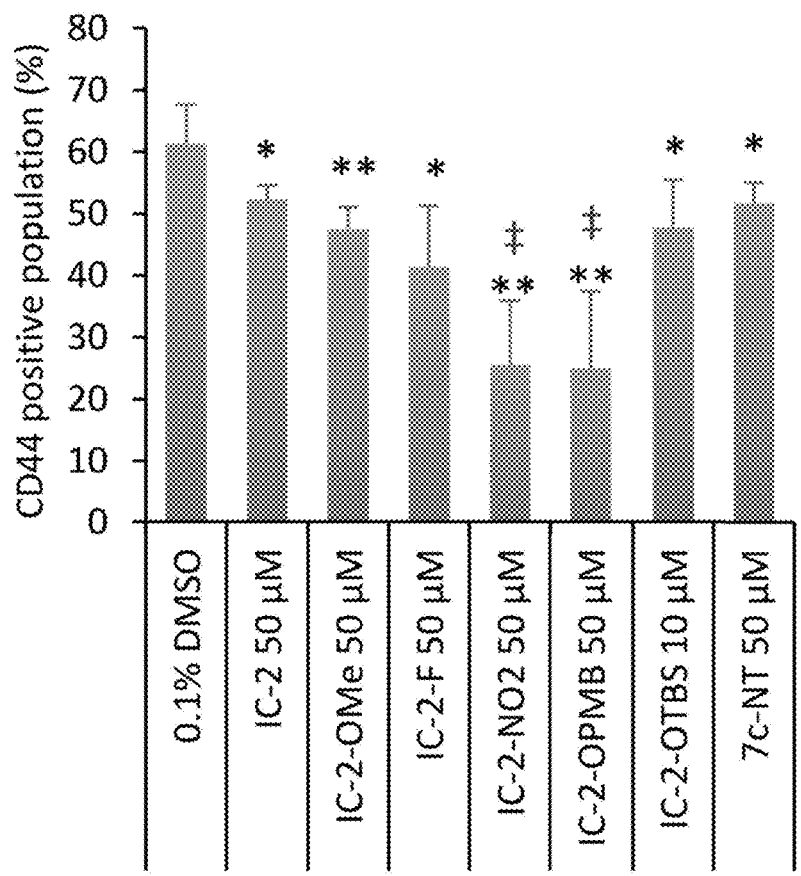
FIG. 32 is a graph showing the results of examining an inhibitory effect of each low-molecular-weight compound on cancer stem cells.

The results demonstrated that all the compounds significantly reduced the percentage of cancer stem cells when compared with control 0.1% DMSO (FIG. 32). Cancer stem cells are known to be able to cause relapse and metastasis of malignant tumors. Thus, any of these novel compounds, which can inhibit the proliferation of cancer stem cells, can be said to be an excellent compound as an active ingredient for anti-malignant tumor therapeutic drugs.

<Example 3> Anti-Fibrosis Effect

3.1. Examples of Reagents Used

DMEM: Dulbecco's Modified Eagle Medium 2 (Nissui Pharmaceutical CO., LTD., Tokyo): 2 mM L-glutamine, 0.2% $NaHCO_3$, and 3500 mg/L D-glucose (Nacalai tesque, Kyoto).

FBS: Fetal bovine serum (Sigma-Aldrich Corp., St. Louis, Mo.).

PBS(−): 8000 mg/L NaCl, 2900 mg/L $Na_2HPO_4.12H_2O$, 200 mg/L KCl, and 200 mg/L $KH_2PO_4$ (Nacalai tesque).

0.25% Trypsin/1 mM EDTA solution (Nacalai tesque).

3.2. Cell Culture

LX-2 cells, a human liver stellate cell line, were cultured and maintained on 10-cm cell culture dishes (TPP Techno Plastic Products AG, Trasadingen, Switzerland) by using 10% FBS/DMEM under conditions at 5% $CO_2$, 37° C., and 100% humidity. When the cells were 70 to 80% confluent, 200 μL of 0.25% Trypsin/1 mM EDTA solution, which had been prepared by diluting the stock solution 10-fold with PBS (−), was added to detach the cells. Then, the cells were centrifuged at 1000 rpm for 3 min at room temperature. The cells recovered were subcultured at a 1:2 split ratio.

3.3. Gene Expression Analysis (Real-Time RT-PCR)

α-Smooth muscle actin (α-SMA), a fibrosis marker, was used as an indicator, and RNA was collected from LX-2 cells treated with each low-molecular-weight compound. Next, an inhibitory effect on fibrosis was examined by real-time RT-PCR.

Figure 33:
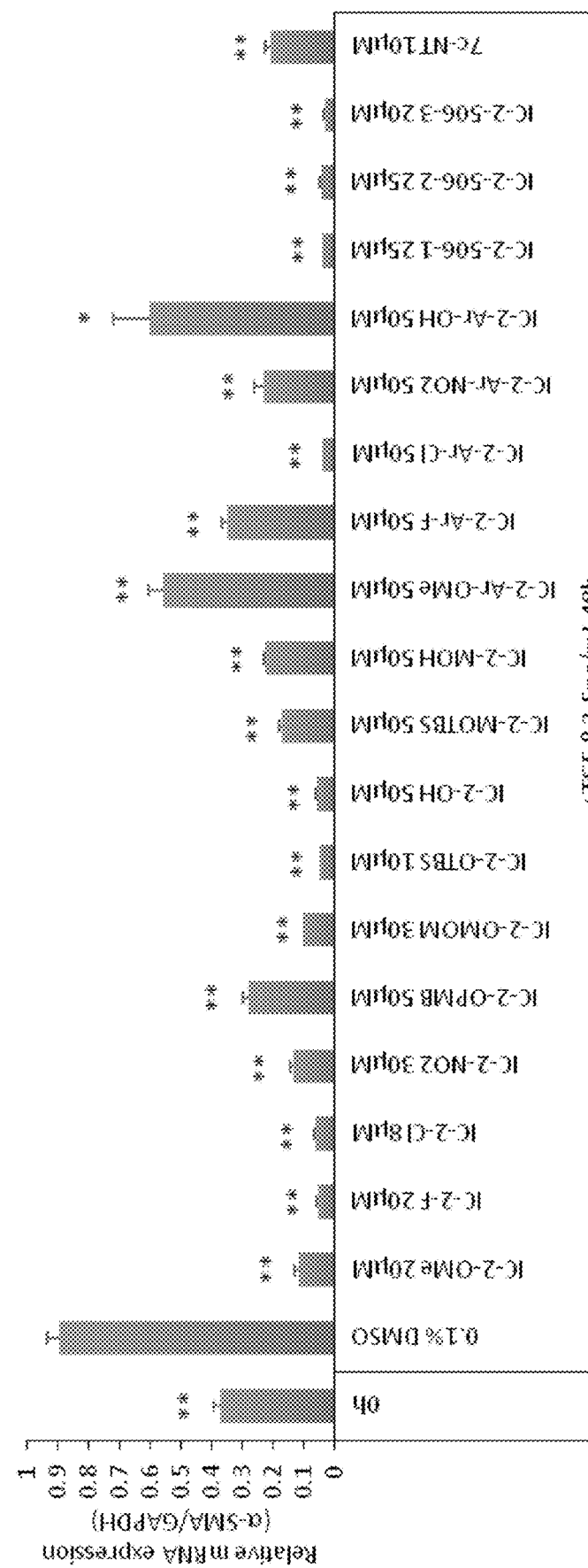
FIGS. 33 to 34 are graphs showing the results of testing an anti-fibrosis effect of each low-molecular-weight compound.

The concentrations of each compound used were as described in FIG. 33. Each control sample used was 0.1% DMSO, a solvent for each compound.

LX-2 cells, which were cultured and maintained in 10% FBS/DMEM, were harvested and seeded (n=3) at $2.0\times10^5$ cells per well of a 6-well plate (TPP) by using 1% FBS/DMEM. After 24 h, 2.5 ng/mL of TGF-β and each compound were added to the cells and the mixture was cultured at 37° C. At 24 h after the compound addition, the culture medium was changed. The culture medium was discarded at 0 and 48 h after the compound treatment. Then, 1 mL of TRIzol (Ambion, Life Technologies Corp., Carlsbad, Calif.) was used to collect RNA.

Next, 0.5 μL of 10 mM Oligo $(dT)_{18}$ primer and 0.5 μL of 10 mM dNTP Mix (PCR Grade, Invitrogen, Life Technologies Corp., Carlsbad, Calif.) were added per μg of the RNA and the total amount was adjusted to 6.5 μL by using MilliQ water. The mixture was incubated at 65° C. for 5 min. Immediately after that, the mixture was cooled on ice. Subsequently, 2 μL of 5×First-Strand Buffer, 1 μL of DTT, and 0.5 μL of 200 U/μL SuperScript II Reverse Transcriptase (Invitrogen) were added. Then, a reverse transcription reaction at 42° C. for 60 min and at 72° C. for 10 min was carried out to synthesize cDNA.

To 2 µL of the cDNA, which had been diluted 10-fold with MilliQ water, were added 0.5 µL of each of 10 µM primers, 0.8 µL of 25 mM $MgCl_2$ stock solution, 2.7 µL of PCR grade $H_2O$, and 1.0 µL of LightCycler FastStart DNA Master SYBER Green I (Roche Diagnostics GmbH, Mannheim, Germany). GAPDH primers used were 5'-AGC CAC ATC GCT CAG ACA C-3' and 5'-GCC CAA TAC GAC CAA ATC C-3'. α-SMA primers used were 5'-CTG TTC CAG CCA TCC TTC AT-3' and 5'-CCG TGA TCT CCT TCT GCA TT-3'.

Equal volumes of 3 samples of cDNA from cells treated with 0.1% DMSO were mixed, and the mixture was diluted to prepare a 5-fold dilution series (up to 6250-fold dilution) as a standard. Then, a 7900HT (Applied Biosystems, Life Technologies Corp., Carlsbad, Calif.) was used to perform a PCR consisting of 1 cycle of 95° C. for 20 sec and 40 cycles of 95° C. for 10 sec, annealing, and 72° C. for 10 sec. The annealing condition for each gene was as follows. GAPDH: 60° C. for 10 sec; and α-SMA: 56° C. for 5 sec. The measurement results were obtained by dividing the calculated value for the α-SMA gene by the calculated value for the GAPDH gene. Note that a significant difference was evaluated by using (two-tailed) Student's t-test. The "*" in figures indicates a significant difference of $p<0.05$ between 0.1% DMSO and each compound; and the "**" indicates a significant difference of $p<0.01$ (the same applies to all the figures in Examples).

The results demonstrated that all the compounds exhibited a significant inhibitory effect on α-SMA expression when compared with control 0.1% DMSO (FIG. 33).

In addition, instead of α-SMA, another fibrosis marker collagen, type I, alpha 1 (COL1A1) was used as an indicator, and substantially the same protocol was repeated. The concentrations of each compound used were as described in FIG. 34. Each control sample used was 0.1% DMSO, a solvent for each compound. Here, COL1A1 primers used were 5'-CCT CCA GGG CTC CAA CGA G-3' and 5'-TCA ATC ACT GTC TTG CCC CA-3'. The annealing was performed at 58° C. for 5 sec. The measurement results were obtained by dividing the calculated value for the COL1A1 gene by the calculated value for the GAPDH gene.

Figure 34:
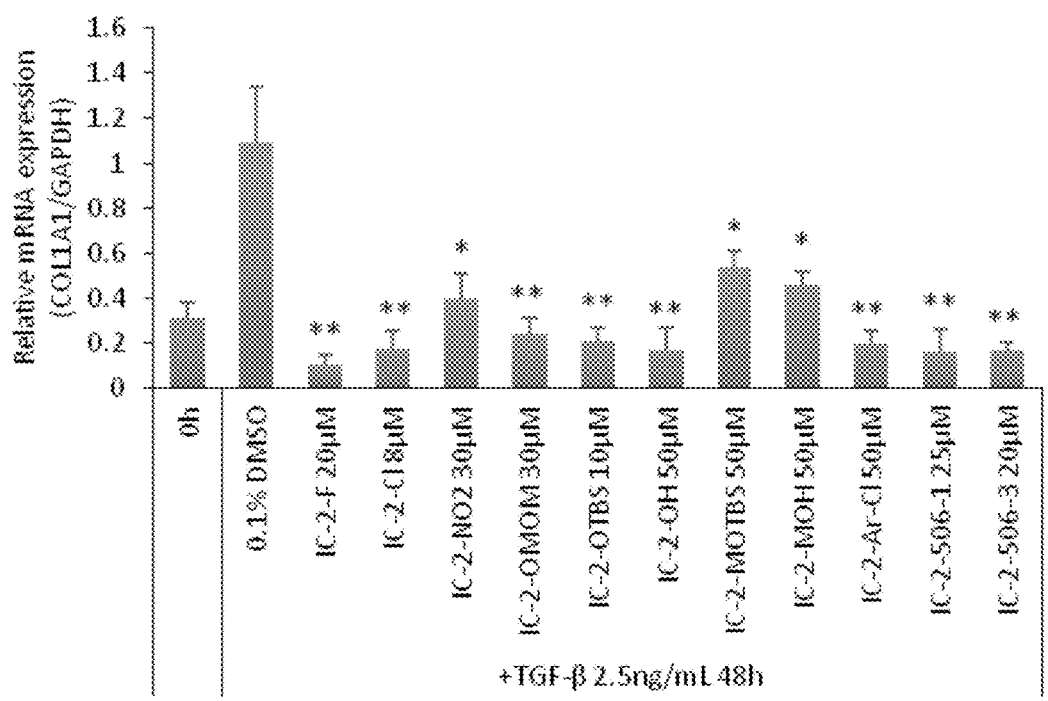

The results demonstrated that all the compounds exhibited a significant inhibitory effect on COL1A1 expression when compared with control 0.1% DMSO (FIG. 34).

<Example 4> Effect of Inducing Differentiation into Hepatocytes 4.1. Examples of Reagents Used DMEM: Dulbecco's Modified Eagle Medium 2 (Nissui Pharmaceutical CO., LTD., Tokyo): 2 mM L-glutamine, 0.2% $NaHCO_3$, 3500 mg/L D-glucose, 100 U/mL penicillin, and 100 µg/mL streptomycin (Nacalai tesque, Kyoto).
FBS: Fetal bovine serum (Sigma-Aldrich Corp., St. Louis, Mo.).
Differentiation-inducing FBS: Fetal bovine serum (Biowest SAS, Nuaille, France).
PBS(-): 8000 mg/L NaCl, 2900 mg/L $Na_2HPO_4 \cdot 12H_2O$, 200 mg/L KCl, and 200 mg/L $KH_2PO_4$ (Nacalai tesque).
PBST: 0.2% Tween-20 (Nacalai tesque)/PBS(-).
0.25% Trypsin/1 mM EDTA solution (Nacalai tesque).
0.1 M Phosphate Buffer (pH 6.8): 0.1 M disodium hydrogenphosphate (Nacalai tesque) aqueous solution was added to 0.1 M sodium dihydrogenphosphate to prepare a phosphate buffer at pH 6.8.
Sulfurous Acid Water: 6 mL of 10% sodium bisulfite (Nacalai tesque) and 5 mL of 1 N hydrochloric acid (Wako Pure Chemical Industries, Ltd., Osaka) were added to 100 mL of MilliQ water to prepare sulfurous acid water.

4.2. Cell Culture

UE7T-13 cells, a human bone marrow-derived mesenchymal stem cell line, were cultured and maintained on 10-cm cell culture dishes (TPP Techno Plastic Products AG, Trasadingen, Switzerland) by using 10% FBS/DMEM under conditions at 5% $CO_2$, 37° C., and 100% humidity. When the cells were 70 to 90% confluent, 200 µL of 0.25% Trypsin/1 mM EDTA solution, which had been prepared by diluting the stock solution 10-fold with PBS (-), was added to detach the cells. Then, the cells were centrifuged at 1000 rpm for 3 min at room temperature. The cells recovered were subcultured at a 1:4 split ratio.

A pTCF4-CMVpro-GL4.20 plasmid vector, having 3 copies of TCF4 motifs (CCT TTG ATC) upstream of aCMV promoter in a multiple cloning site of pGL4.20 (Promega Corp., Fitchburg, Wis.), was linearized and stably transfected into UE7T-13 cells to prepare E7-TCF4 cells. Also, a pCMVpro-GL4.20 plasmid vector, having a CMV promoter in a multiple cloning site of pGL4.20, was linearized and stably transfected into UE7T-13 cells. The resulting stable cells (E7-CMV cells) were cultured, like UE7T-13 cells, in 10% FBS/DMEM containing 0.25 µg/mL puromycin.

4.3. Gene Expression Analysis (Real-Time RT-PCR)

Albumin, a hepatocyte marker, was used as an indicator, and RNA was collected from cells treated with each compound. Next, a hepatocyte differentiation-inducing effect was examined by real-time RT-PCR. The concentrations of the respective compounds were as described in FIG. 35. Each control sample used was 0.1% DMSO, a solvent for each compound.

First, 70 to 90% confluent UE7T-13 cells were harvested and seeded in 10% FBS-containing DMEM at $8.064 \times 10^4$ cells/well of a 6-well plate (TPP) ($9.0 \times 10^3$ cells/cm$^2$). One day after that, each compound was added to the cells in DMEM containing differentiation-inducing 10% FBS and the mixture was cultured at 37° C. Day 4 after the compound addition, the culture medium was changed. Days 0 and 7 after the compound treatment, the culture medium was discarded, and RNA was recovered by using RNeasy Mini (Qiagen GmbH, Hilden, Germany). Then, the sample was treated with DNase on the column.

Next, 0.5 µL of 10 mM Oligo $(dT)_{18}$ primer and 0.5 µL of 10 mM dNTP Mix (PCR Grade, Invitrogen, Life Technologies Corp., Carlsbad, Calif.) were added per µg of the RNA and the total amount was adjusted to 6.5 µL by using MilliQ water. The mixture was incubated at 65° C. for 5 min. Immediately after that, the mixture was cooled on ice. Subsequently, 2 µL of 5×First-Strand Buffer, 1 µL of DTT, and 0.5 µL of 200 U/µL SuperScript II Reverse Transcriptase (Invitrogen) were added. Then, a reverse transcription reaction at 42° C. for 60 min and at 72° C. for 10 min was carried out to synthesize cDNA.

To 2 µL of the cDNA, which had been diluted 10-fold with MilliQ water, were added 0.9 µL of each of 10 µM primers, 1.2 µL of each probe, and 5.0 µL of EXPRESS qPCR SuperMix with Premixed ROX (Invitrogen). GAPDH primers used were 5'-AGC CAC ATC GCT CAG ACA C-3' and 5'-GCC CAA TAC GAC CAA ATC C-3'. In addition, Probe #60 of Universal Probe Library (Roche Diagnostics GmbH, Mannheim, Germany) was used as a probe for detecting GAPDH. Albumin primers used were 5'-CAA AGA TGA CAA CCC AAA CCT C-3' and 5'-GGA TGT CTT CTG GCA ATT TCA-3'. In addition, Probe #54 of Universal Probe Library was used as a probe for detecting albumin.

The cDNA from HuH-7 cells were used to prepare a 5-fold dilution series as a standard. Then, a 7900HT (Applied Biosystems, Life Technologies Corp., Carlsbad, Calif.) was used to perform a PCR consisting of 1 cycle of 50° C. for 2 min and 95° C. for 20 sec and 45 cycles of 95° C. for 1 sec and 60° C. for 20 sec. The measurement results were obtained by dividing the calculated value for the albumin gene by the calculated value for the GAPDH gene. Note that a significant difference was evaluated by using (two-tailed) Student's t-test. The "*" in figures indicates a significant difference of p<0.05 between 0.1% DMSO and each compound; and the "**" indicates a significant difference of p<0.01 (the same applies to all the figures in Examples).

Figure 35:
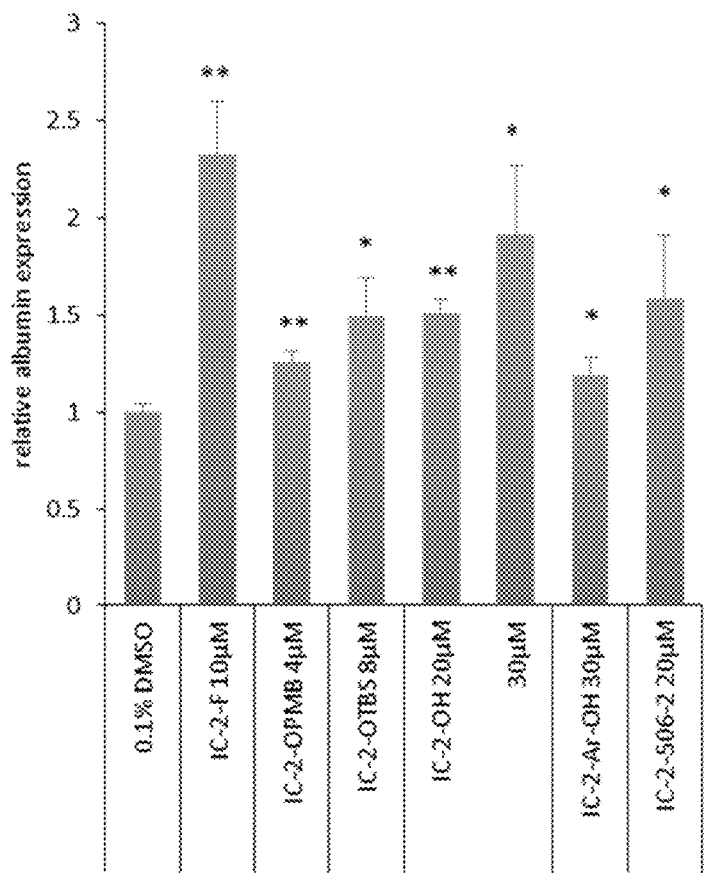
FIGS. 35 to 39 are graphs and photographs showing the results of testing a hepatocyte differentiation-inducing effect of each low-molecular-weight compound.

The results demonstrated that when the cells were treated with any of the compounds, significant albumin gene expression was exhibited over control 0.1% DMSO (FIG. 35).

4.4. Hepatocyte Function Analysis (Urea Assay)

By using urea synthesis, a hepatocyte function, as an indicator, a hepatocyte differentiation-inducing effect of each compound was investigated.

Figure 36:
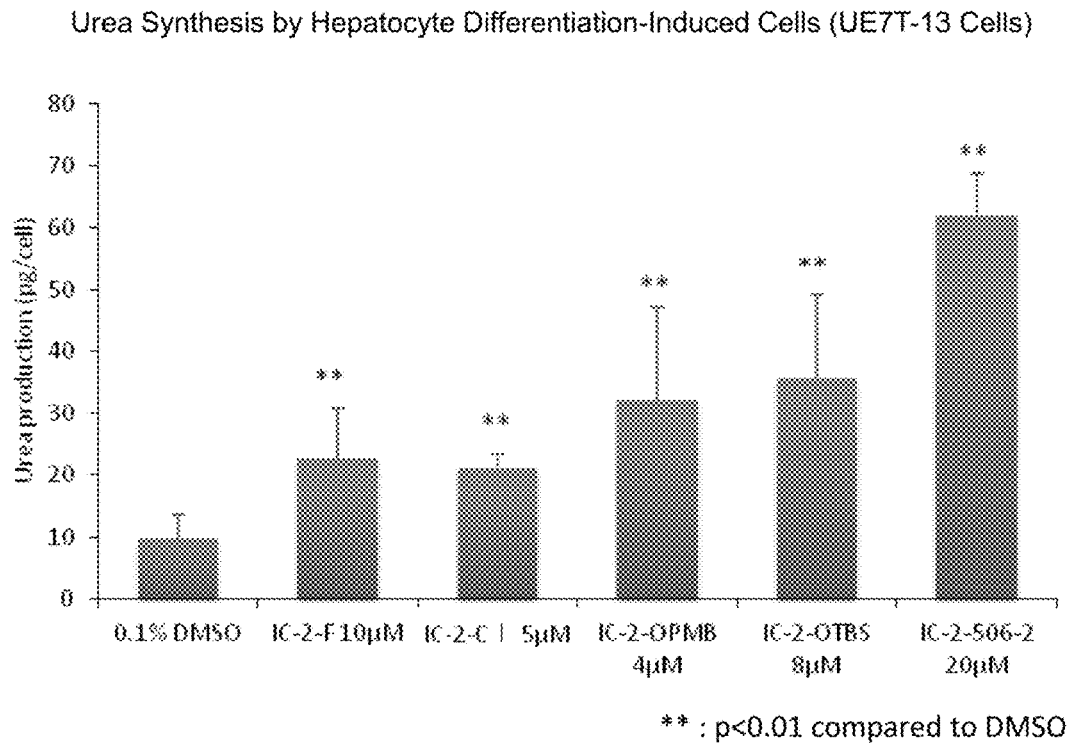

The concentrations of the respective compounds were as described in FIG. 36. Each control sample used was 0.1% DMSO, a solvent for each compound.

First, 70 to 90% confluent UE7T-13 cells were harvested and seeded (n=6) in 10% FBS/DMEM at $1.6758 \times 10^4$ cells/well of a 24-well plate (TPP) ($9.0 \times 10^3$ cells/cm$^2$). One day after that, each compound was added to the cells in differentiation-inducing 10% FBS/DMEM and the mixture was cultured at 37° C. Day 4 after the compound addition, the culture medium was changed.

Day 7 after the compound treatment, the cells were further cultured for 4 days in differentiation-inducing 10% FBS/DMEM containing 5 mM ammonium chloride (Nacalai tesque) and each compound. The urea content of the culture medium was determined by using a QuantiChrom Urea Assay Kit (BioAssay Systems LLC, Hayward, Calif.) and its absorbance (at a measurement wavelength of 430 nm) was measured by using a Sunrise Rainbow RC (Tecan Group Ltd., Mannedorf, Switzerland). The measurement results were calculated by subtracting, from the reading, absorbance obtained by adding a kit reagent to the differentiation-inducing 10% FBS/DMEM. The respective cells were detached by using 50 µL of 0.25% Trypsin/1 mM EDTA solution, which had been prepared by diluting the stock solution 10-fold with PBS (−). Then, the number of the cells was counted. The measurement results were obtained by dividing the urea content in each well by the cell count.

The results demonstrated that all the compounds induced significant urea synthesis when compared with control 0.1% DMSO (FIG. 36).

4.5. Hepatocyte Function Analysis (Immunofluorescence Staining)

The cells treated with each compound were subjected to immunofluorescence analysis of albumin, a hepatocyte marker, to investigate a hepatocyte differentiation-inducing effect. The concentrations of the respective compounds were as described in FIG. 37. Each control sample used was 0.1% DMSO, a solvent for each compound.

Next, 70 to 90% confluent UE7T-13 cells were harvested and seeded (n=3) in 10% FBS/DMEM at $1.53 \times 10^4$ cells/well of a Lab-Tek II chamber slide (Nunc, Thermo Fisher Scientific Inc., Madison, Mass.) ($9.0 \times 10^3$ cells/cm$^2$). One day after that, each compound was added to the cells in differentiation-inducing 10% FBS/DMEM and the mixture was cultured at 37° C. Day 4 after the compound addition, the culture medium was changed.

Days 0 and 7 after the compound treatment, the culture medium was discarded, and the cells were washed once with 800 µL of PBS(−). Next, the cells were fixed for 20 min in 500 µL of PBS(−) containing 4% paraformaldehyde (Nacalai tesque) and 8% sucrose (Wako Pure Chemical Industries, Ltd.). Then, the cells were washed twice with 1 ml of PBS(−) and were subjected to permeabilization by using 0.2% Triton X-100 (Wako Pure Chemical Industries, Ltd.) for 10 min. After washed once with 1 mL of PBS(−), the cells were blocked for 30 min in 500 µL of 3% BSA (Nacalai tesque)-containing PBS(−). Then, an excessive blocking solution was removed, and a primary antibody reaction was carried out at 4° C. overnight by adding 75 µL of a mouse anti-human albumin monoclonal antibody (HAS-11, Sigma-Aldrich), which had been diluted 1000-fold with 0.1% BSA/PBS(−). After the cells were washed 5 times with 0.1% BSA/PBS(−), 100 µL of Alexa Fluor 488-labeled goat anti-mouse IgG (H+L) (ab150113, Abcam Ltd., Cambridge, UK), which had been diluted 1000-fold with 1% BSA/PBST, was added. Then, a secondary antibody reaction was carried out at room temperature for 1 h. For nuclear staining, 2 mg/mL DAPI (Cell Signaling Technology Inc., Danvers, Mass.) was diluted 1000-fold for usage. After completion of the reaction, the cells were washed 5 times with 1 mL of PBST and once with 1 mL of MilliQ water. Each sample was sealed with a manicure and sealant containing a color fading inhibitor and was observed under a FV1000D IX81 (Olympus Corporation, Tokyo). As a positive control, used were HuH-7 cells seeded at $2.5 \times 10^4$ cells/cm$^2$. The image data acquired were analyzed by using image analysis software inForm 2.0.4 (PerkinElmer, Waltham, Mass.), and the percentage of positive cells was calculated.

Figure 37:
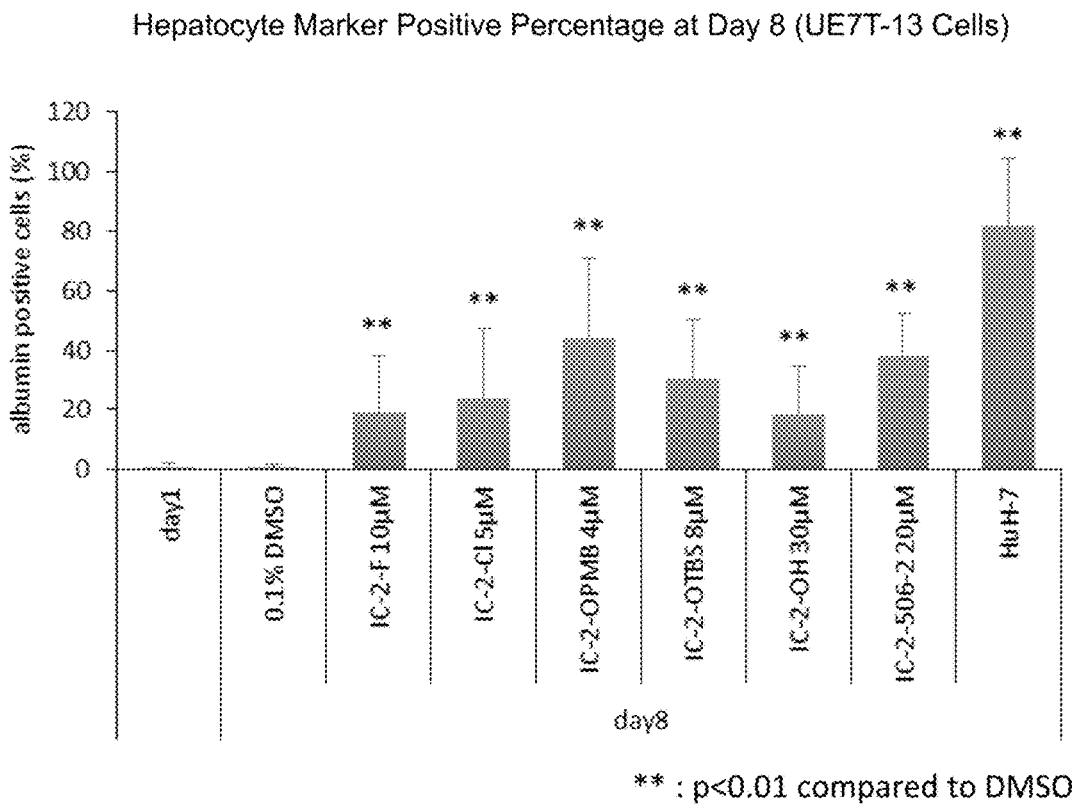
Figure 38:
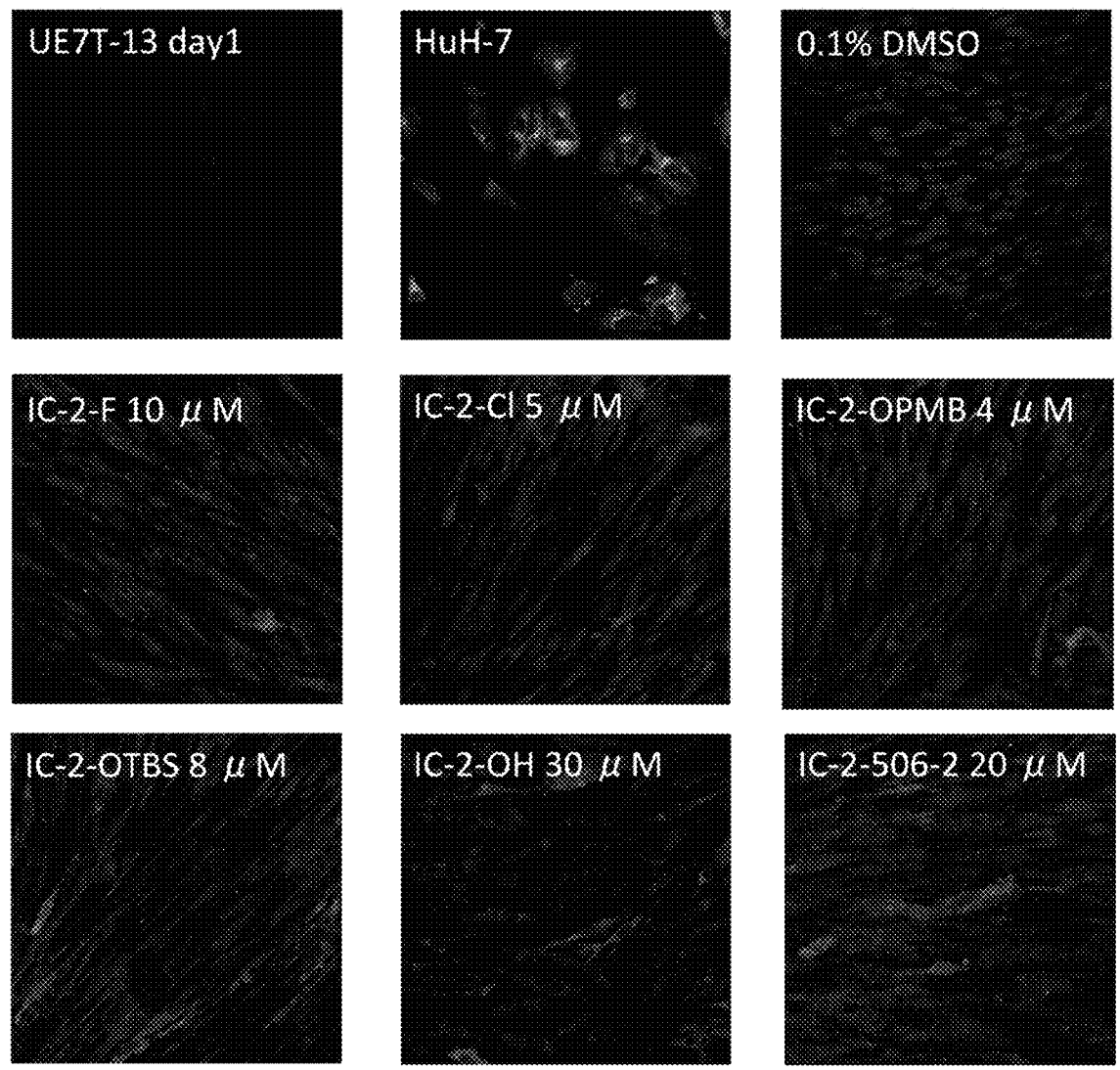

The results demonstrated that all the compounds induced significant albumin protein expression when compared with control 0.1% DMSO (FIGS. 37 and 38).

4.6. Hepatocyte Function Analysis (PAS Staining)

By using glycogen synthesis, a hepatocyte function, as an indicator, a hepatocyte differentiation-inducing effect of each compound was investigated.

Figure 39:
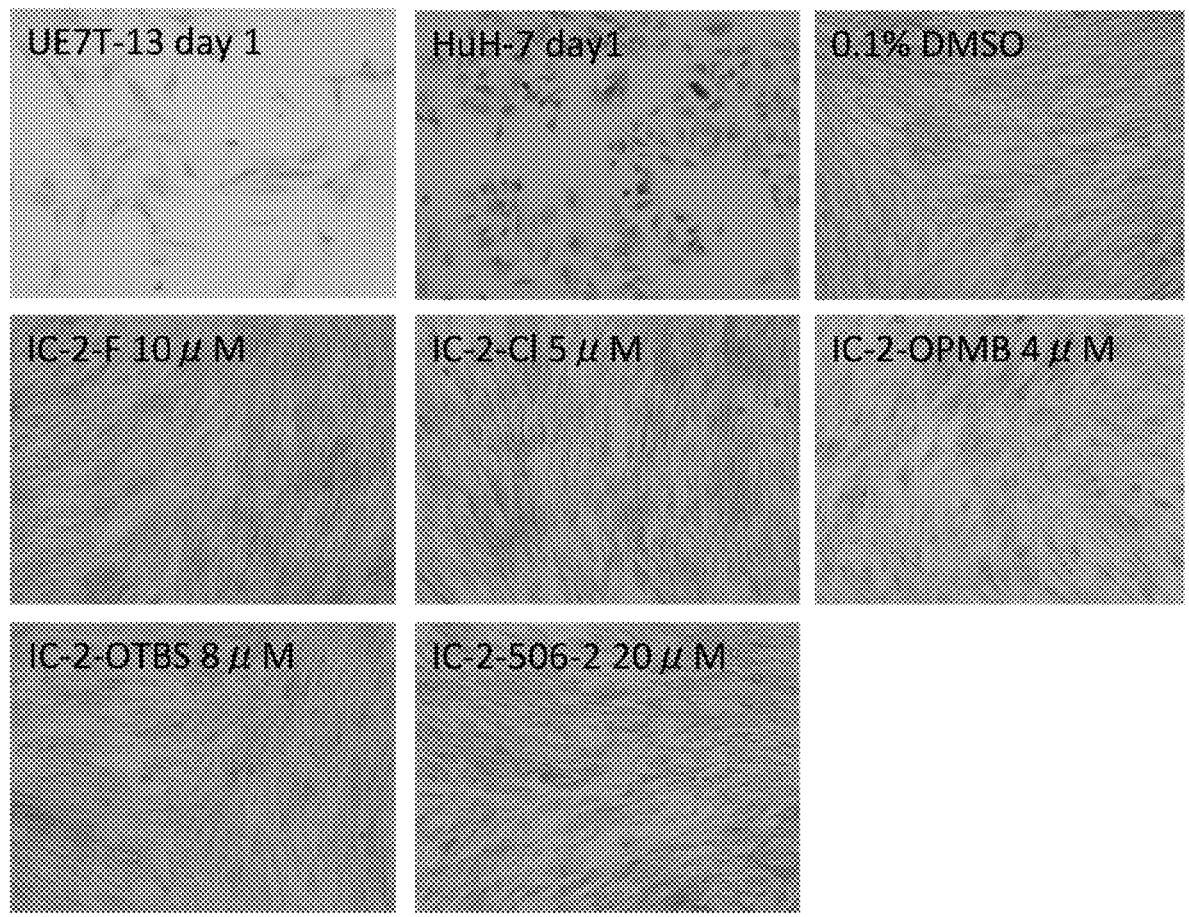

The concentrations of the respective compounds were as described in FIG. 39. Each control sample used was 0.1% DMSO, a solvent for each compound.

Next, 70 to 90% confluent UE7T-13 cells were harvested and seeded (a total of 4 wells per sample: n=3+negative control) in 10% FBS/DMEM at $1.53 \times 10^4$ cells/well of a Lab-Tek II chamber slide ($9.0 \times 10^3$ cells/cm$^2$). One day after that, each compound was added to the cells in differentiation-inducing 10% FBS/DMEM and the mixture was cultured at 37° C. Day 4 after the compound addition, the culture medium was changed.

Days 0 and 7 after the compound treatment, the culture medium was discarded, and the cells were washed twice with 1 µL of PBS(−). Next, the cells were fixed for 30 min in 500 µL of 4% paraformaldehyde/PBS(−). After the cells were washed twice with 1 mL of PBS(−), 450 µL of 0.1 M phosphate buffer (pH 6.8) was added. For negative control, 50 µL of 10 mg/mL α-amylase (Nacalai tesque) was added. Then, the mixture was incubated at 37° C. for 1 h to digest glycogen. Subsequently, the cells were washed 3 times with 1 mL of MilliQ water and were treated for 10 min with 500 µL of 1% periodic acid aqueous solution (Nacalai tesque) to oxidize saccharides. The cells were then washed 3 times with 1 mL of MilliQ water and were treated for 15 min with 500 µL of Schiff's Reagent Solution (Nacalai tesque) to stain glycogen. The resulting cells were washed 3 times with 1 mL of sulfurous acid water and 3 times with 1 mL of MilliQ water. The nuclei were stained for 1 min with Mayer's Hematoxylin (MUTO PURE CHEMICALS CO., LTD., Tokyo). Then, the cells were washed 3 times with 1 mL of MilliQ water. After sealing with Entellan new (Merck Millipore Corporation, Darmstadt, Germany), the cells were observed under a BZ-9000 (KEYENCE CORPORATION, Osaka). As a positive control, used were HuH-7 cells seeded at $2.5 \times 10^4$ cells/cm$^2$.

The results demonstrated that all the compounds induced glycogen synthesis (FIG. 39).

<Example 5> Inhibitory Effect on Wnt/β-Catenin Signaling 5.1. Inhibitory Effect on Wnt/β-Catenin Signaling in Liver Cancer Cells While each compound was added at concentrations where the growth of HuH-7 cells was reduced to about 50% or less, Wnt/β-catenin signaling activity was measured. The concentrations of the respective compounds were as described in FIG. 40. Control samples used were 0.1% DMSO, a solvent for each compound, and 0.5 µM 5-FU.

First, 70 to 90% confluent HuH7-TCF4 cells were harvested and seeded (n=3) at $5.0 \times 10^4$ cells/well of a 24-well plate (TPP). After 24 h, each compound was added to the cells and the mixture was cultured at 37° C.

At 48 h after the compound treatment, the culture medium was discarded, and 100 µL of room temperature 5×Passive Lysis Buffer (PLB) (Promega Corp., Fitchburg, Wis.), which had been diluted 5-fold with MilliQ water, was added to each well. Next, the plate was shaken at room temperature for 15 min and was then frozen at −30° C. overnight. A Luciferase Assay Substrate was diluted with 10 mL of room temperature Luciferase Assay Buffer II to prepare Luciferase Assay Reagent II (LARII) (Promega). The frozen PLB lysate samples were thawed and permeabilized for 15 min. Then, 10 µL aliquots were added to wells of a 96-well white plate (Corning Inc., Corning, N.Y.). While 50 µL aliquots of LARII were each added to each well, luminescence was quantified by using a 1420 multi-label counter ARVO MX (PerkinElmer Singapore Pte Ltd., Singapore) to determine firefly luciferase activity. Note that a significant difference was evaluated by using (two-tailed) Student's t-test. The "*" in figures indicates a significant difference of p<0.05 between 0.1% DMSO and each compound; and the "**" indicates a significant difference of p<0.01 (the same applies to all the figures in Examples).

Figure 40:
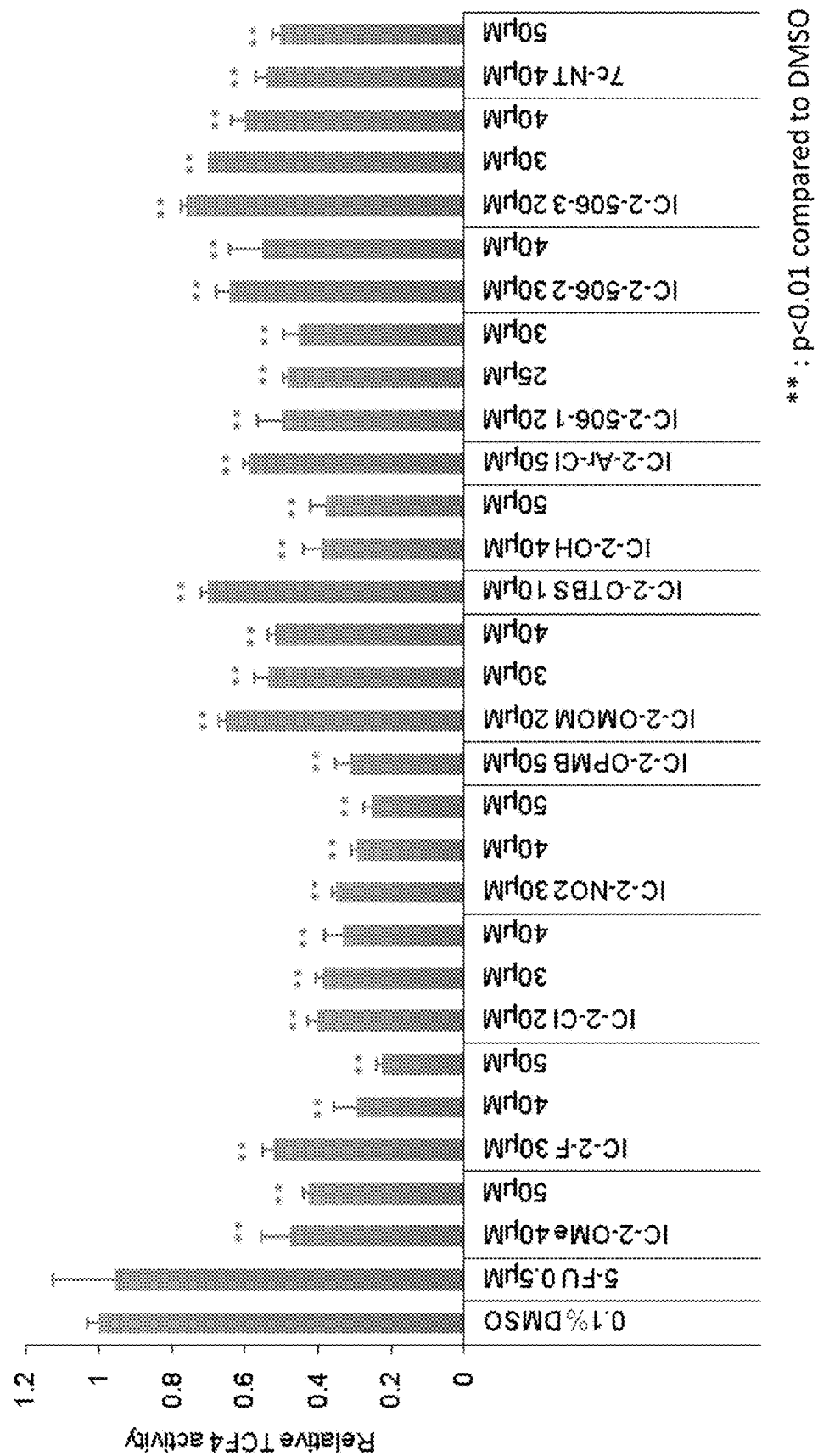
FIGS. 40 to 42 are graphs showing the results of examining an inhibitory effect of each low-molecular-weight compound on Wnt/β-catenin signaling.

The results demonstrated that all the compounds exhibited a significant inhibitory effect on Wnt/β-catenin signaling when compared with control 0.1% DMSO (FIG. 40).

5.2. Inhibitory Effect on Wnt/β-Catenin Signaling in Liver Stellate Cells

While each compound was added at concentrations where the cell growth of fibrosis-causing liver stellate LX-2 cells was reduced to about 50 to 80%, Wnt/β-catenin signaling activity was measured. Neither 100 µM of 9b nor 9b-CONH$_2$ exhibited a growth inhibitory effect on LX-2 cells. The concentrations of the respective compounds were as described in FIG. 41. Each control sample used was 0.1% DMSO, a solvent for each compound.

LX-2 cells, which were cultured and maintained by using 10% FBS/DMEM, were harvested and seeded (n=3) in 1% FBS/DMEM at $4.0 \times 10^4$ cells per well of a 24-well plate. Next, 25 µL of Opti-MEM (Gibco, Life Technologies Corp., Carlsbad, Calif.) containing 50 ng of pTCF4-CMVpro-GL4.20, having 3 copies of TCF motifs (CCT TTG ATC) upstream of a CMV promoter in a multiple cloning site of pGL4.20 (Promega), and 5 ng of pRL-CMV Vector (Promega) and 25 µL of Opti-MEM containing 0.4 µL of Lipofectamine 2000 (Invitrogen, Life Technologies Corp., Carlsbad, Calif.) were mixed and incubated at room temperature for 20 min. At 20 h after the cell seeding, the mixture was added to each well, so that both reporter plasmids were transiently transfected into the cells. After additional 4 h, 2.5 ng/mL of TGF-β and each compound were added to the cells and the mixture was cultured at 37° C.

At 24 and 48 h after the compound treatment, the culture medium was discarded, and 100 µL of room temperature 5×Passive Lysis Buffer (PLB), which had been diluted 5-fold with MilliQ water, was added to each well. Next, the plate was shaken at room temperature for 15 min and was then frozen at −30° C. overnight. A Luciferase Assay Substrate was diluted with 10 mL of room temperature Luciferase Assay Buffer II to prepare Luciferase Assay Reagent II (LARII). Then, 1 µL of Stop&Glo Substrate was diluted with 49 µL of room temperature Stop&Glo Buffer to prepare Stop&Glo (Promega) in a quantity enough for samples.

The frozen PLB lysate samples were thawed and permeabilized for 15 min. After that, 50 µl aliquots of LARII were dispensed into 3.5 mL test tubes (Sarstedt, AG & Co., Numbrecht, Germany) and 10 µL of each frozen PLB lysate sample was added and mixed well. Subsequently, luminescence was quantified by using a MiniLumat LB 9506 (Berthold Technologies GmbH & Co, Bad Wildbad, Germany) to measure firefly luciferase activity. After the measurement, 50 µL of Stop&Glo was added and mixed well and luminescence was then quantified by using the MiniLumat LB 9506 to determine *Renilla* luciferase activity. The measurement results were obtained by dividing the firefly luciferase activity by the *Renilla* luciferase activity.

Figure 41:
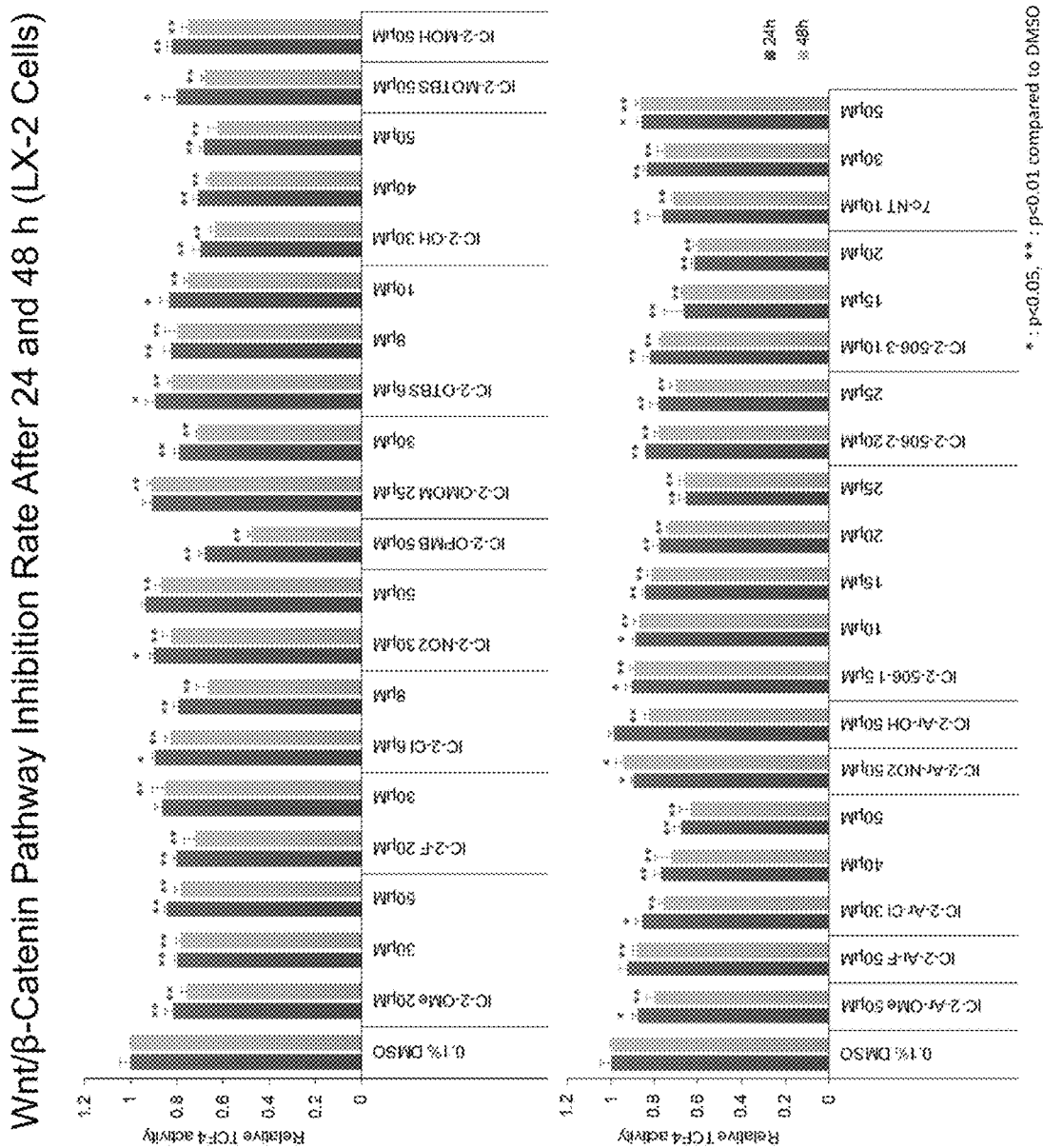

The results demonstrated that all the compounds exhibited a significant inhibitory effect on Wnt/β-catenin signaling when compared with control 0.1% DMSO (FIG. 41).

5.3. Inhibitory Effect on Wnt/β-catenin Signaling in Mesenchymal Stem Cells

UE7T-13 cells were used to measure Wnt/β-catenin signaling activity. The concentrations of the respective compounds were as described in FIG. 42. Each control sample used was 0.1% DMSO, a solvent for each compound.

First, 70 to 90% confluent E7-TCF4 cells and E7-CMV cells were harvested and seeded (n=3) at $1.6758 \times 10^4$ cells/well of a 24-well plate ($9.0 \times 10^3$ cells/cm$^2$). One day after that, each compound was added to the cells and the mixture was cultured at 37° C. Day 4 after the compound addition, the culture medium was changed.

At day 1, 4, or 8 after the compound treatment, the culture medium was discarded, and 100 μL of room temperature 5×Passive Lysis Buffer (PLB), which had been diluted 5-fold with MilliQ water, was added to each well. Next, the plate was shaken at room temperature for 15 min and was then frozen at −30° C. overnight. A Luciferase Assay Substrate was diluted with 10 mL of room temperature Luciferase Assay Buffer II to prepare Luciferase Assay Reagent II (LARII). The frozen PLB lysate samples were thawed and permeabilized for 15 min. Then, 10 μL aliquots were added to wells of a 96-well white plate. While 50 μL aliquots of LARII were each added to each well, luminescence was quantified by using a 1420 multi-label counter ARVO MX to determine firefly luciferase activity.

Figure 42:
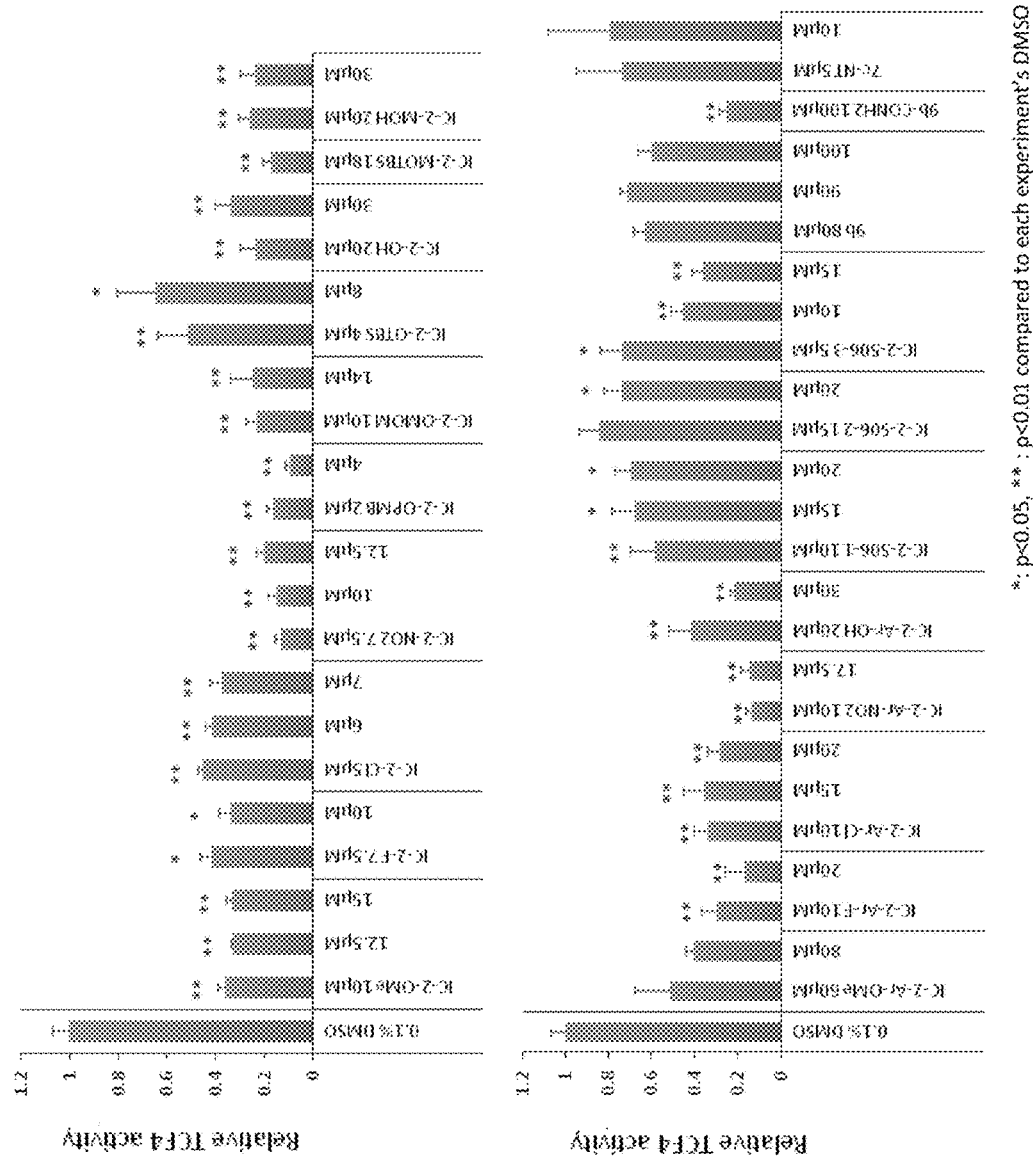

The results demonstrated that at day 8 after the compound addition, all the compounds except for IC-2-Ar-OMe, 9b, and 7c-NT exhibited a significant inhibitory effect on Wnt/β-catenin signaling when compared with control 0.1% DMSO (FIG. 42).

<Example 6> Anti-Tumor Effect on Liver Cancer 6.1. Examples of Reagents Used

DMEM: Dulbecco's Modified Eagle Medium 2 (Nissui Pharmaceutical CO., LTD., Tokyo): 2 mM L-glutamine, 0.2% NaHCO$_3$, 3500 mg/L D-glucose (Nacalai tesque, Kyoto), and 10% fetal bovine serum (FBS) (Sigma-Aldrich Corp., St. Louis, Mo.).
PBS(−): 8000 mg/L NaCl, 2900 mg/L Na$_2$HPO$_4$.12H$_2$O, 200 mg/L KCl, and 200 mg/L KH$_2$PO$_4$ (Nacalai tesque).
0.25% Trypsin/1 mM EDTA solution (Nacalai tesque).
IC-2: synthesized in accordance with the process described in WO2012/141038.

6.2. Cell Culture

HuH-7 cells, a human liver cancer cell line, were cultured on 10-cm cell culture dishes (TPP Techno Plastic Products AG, Trasadingen, Switzerland) by using DMEM under conditions at 5% CO$_2$, 37° C., and 100% humidity. When the cells were 70 to 90% confluent, 200 μL of 0.25% Trypsin/1 mM EDTA solution, which had been prepared by diluting the stock solution 10-fold with PBS (−), was added to detach the cells. Then, the cells were centrifuged at 1000 rpm for 3 min at room temperature. The cells recovered were subcultured at a 1:4 split ratio.

A pTCF4-CMVpro-GL4.20 plasmid vector, having a CMV promoter and 3 copies of upstream TCF4 motifs (CCT TTG ATC) in a multiple cloning site of pGL4.20 (Promega Corp., Fitchburg, Wis.), was linearized and stably transfected into the HuH-7 cells. The resulting stable cells(HuH7-TCF4 cells) and HuH-7 cells were likewise cultured.

6.3. Growth Inhibitory Effect on Cancer Cells (WST Assay)

First, 70 to 90% confluent HuH-7 cells were harvested and seeded (n=3) at $1 \times 10^4$ cells/well of a 96-well plate (TPP). After 24 h, IC-2 was added to the cells and the mixture was cultured at 37° C. Each control sample (0 μM) used was 1% DMSO, a solvent for each compound. The concentrations of IC-2 used were 0, 1, 5, 10, 25, and 50 μM.

Next, day 4 after the IC-2 treatment, 100 μL of DMEM-diluted 10% Cell Counting Kit-8 (DOJINDO LABORATORIES, Kumamoto) was added. The mixture was incubated at 37° C. for 60 min and its absorbance (at a measurement wavelength of 450 nm/control wavelength of 600 nm) was measured by using a Sunrise Rainbow RC (Tecan Group Ltd., Mannedorf, Switzerland). Absorbance for the cells alone was calculated by subtracting, from the reading obtained, absorbance for 10% Cell Counting Kit-8 alone.

Meanwhile, IC50 of each compound was calculated as $IC50=10^{\{LOG(A/B) \times (50-C)/(D-C)+LOG(B)\}}$ wherein A is a higher concentration which gives more than 50% inhibition; B is a lower concentration which gives less than 50% inhibition; C is the level of inhibition at the concentration B; and D is the level of inhibition at the concentration A. Note that a significant difference was evaluated by using (two-tailed) Student's t-test. The "*" in figures indicates a significant difference of p<0.05 between 0.1% DMSO and each compound; and the "**" indicates a significant difference of p<0.01 (the same applies to all the figures in Experimental Examples).

Figure 43:
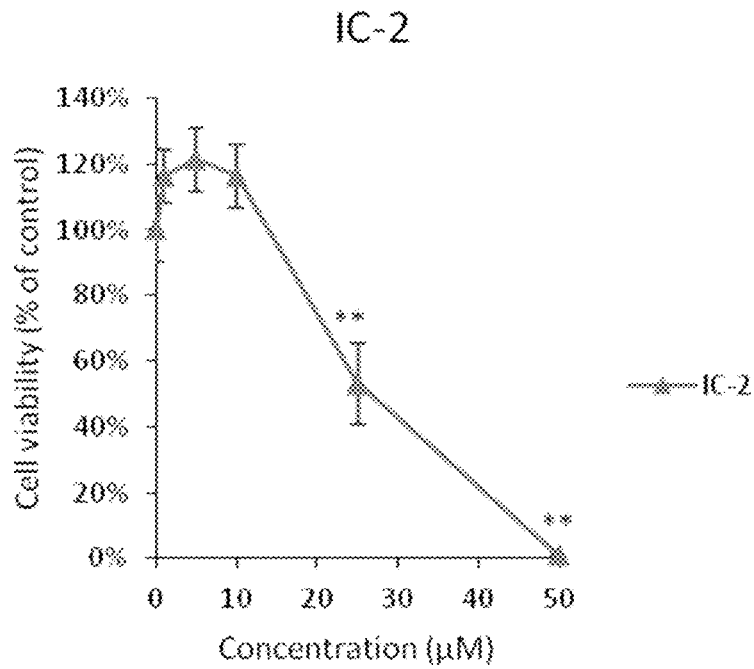
FIG. 43 is a graph showing the results of examining an anti-tumor effect of one of the low-molecular-weight compounds.

The results demonstrated that IC-2 treatment inhibited the growth of HuH-7 cells (FIG. 43). The IC50 of IC-2 was 25.95 μM.

6.4. Inhibitory Effect on Cancer Stem Cells (FCM Analysis)

CD44, a cancer stem cell marker, was used as an indicator to examine an inhibitory effect of IC-2 on cancer stem cells. First, 70 to 90% confluent HuH-7 cells were harvested and seeded at $1.5 \times 10^6$ cells per 10-cm cell culture dish. After 15 h, the cells were treated with hexachlorophene (15 μM), ICG-001 (15 μM), PKF118-310 (5 μM), IC-2 (50 μM), or 5-FU (0.5 μM), and the mixture was cultured at 37° C. Each control sample used was 1% DMSO, a solvent for each compound or the anti-cancer drug. Day 2 after the drug treatment, the cells were harvested from each culture dish. The cells were centrifuged at 1000 rpm and at 4° C. for 5 min to remove a supernatant and were then washed twice with 1 mL of 0.5% FBS/2 mM EDTA/PBS. Next, the cells were suspended in 500 μL of 5% BSA/0.5% FBS/2 mM EDTA/PBS for blocking at 4° C. for 15 min.

Then, 5 μL of a mouse anti-human CD44 monoclonal antibody (156-3C11, Cell Signaling Technology Inc., Danvers, Mass.) was added to 500 μL of the cell suspension. The mixture was resuspended and subjected to a primary antibody reaction in a dark room at 4° C. for 10 min. After that, the cells were washed 3 times with 1 mL of PBS. Subsequently, 1.0 μg of Alexa Fluor 488-labeled IgG (H+L) (Life Technologies Corp., Carlsbad, Calif.) was added and the mixture was suspended. Then, a secondary antibody reaction was carried out in a dark room at 4° C. for 10 min. After that, the cells were washed 3 times with 1 mL of FBS, followed by washing once with 0.5% FBS/2 mM EDTA/PBS. Thereafter, the cells were suspended in 500 μL of 0.5% FBS/2 mM EDTA/PBS and were made to pass through a 40 μm-mesh column (Becton, Dickinson and Company, Franklin Lakes, N.J.). A Beckman Coulter-Moflo XDP (Beckman Coulter Inc., Fullerton, Calif.) was used for analysis. Following the analysis, further analysis was conducted by adding 2 μL of 0.25 mg/mL Propidium Iodide (PI). The same experiment was repeated five times.

Figure 44:
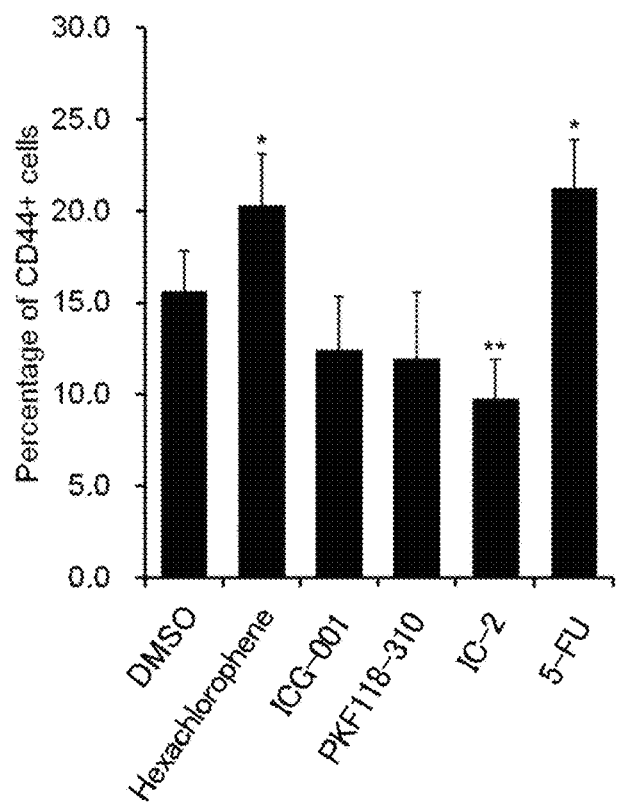
FIG. 44 is a graph showing the results of examining an inhibitory effect of each low-molecular-weight compound on cancer stem cells.

The results demonstrated a significant reduction in the number of cancer stem cells in the case of using IC-2, compared with the case of using control 1% DMSO (FIG. 44). However, use of 5-FU, a representative anti-cancer drug, rather increased the number of cancer stem cells.

6.5. Liver Cancer Model Mouse Used to Evaluate Anti-Malignant Tumor Therapeutic Effect CD44-positive HuH-7 cells were subcutaneously transplanted in mice. Next, the engrafted mice were divided into 3 groups (DMSO group: 5 mice; 5-FU group: 4 mice; and IC-2 group: 4 mice). Then, DMSO was added to prepare 30 mg/kg of 5-FU and 50 mg/kg of IC-2 such that each liquid volume was 100 µL; and 100% DMSO, a solvent for each drug, was used as a control sample. Subsequently, each drug was dosed intraperitoneally every three days. The body weight of each mouse and the long and short diameters of a tumor were measured every three days. The tumor volume was calculated by using the following equation: Tumor volume=Long diameter×(Short diameter)$^2$×0.5. The volume at Day 0 was used to normalize each tumor volume, and then a graph was created. To fully evaluate a 5-FU effect, the 5-FU dose was set to an amount 2 times the regular amount 15 mg/kg used in research articles. The concentration of IC-2 corresponding to a concentration at which Wnt/β-catenin signaling was inhibited in vitro was calculated. Then, the concentration was doubled to set an IC-2 dose.

Figure 45:
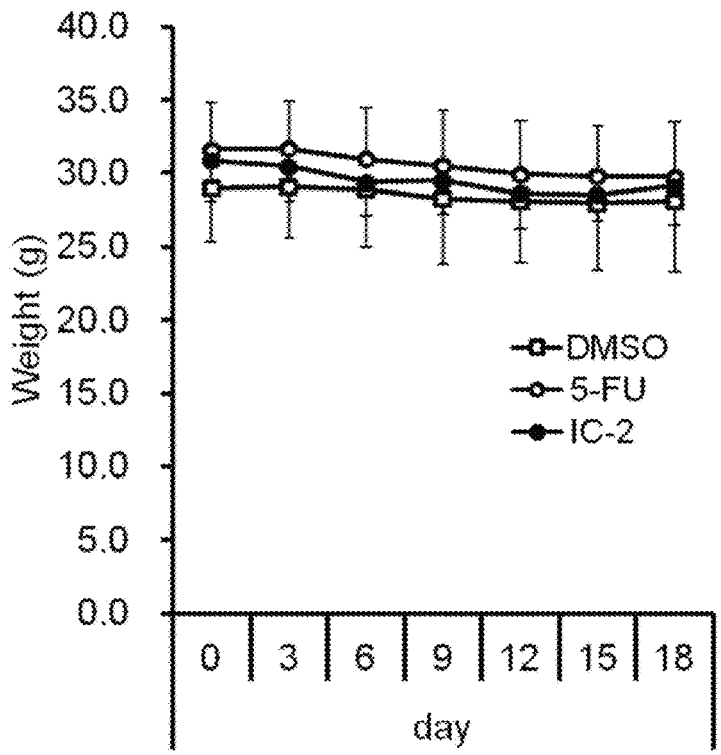
FIG. 45 is a graph showing the time-course of the change in the body weight of each of liver cancer model mice after dosing each low-molecular-weight compound.
Figure 46:
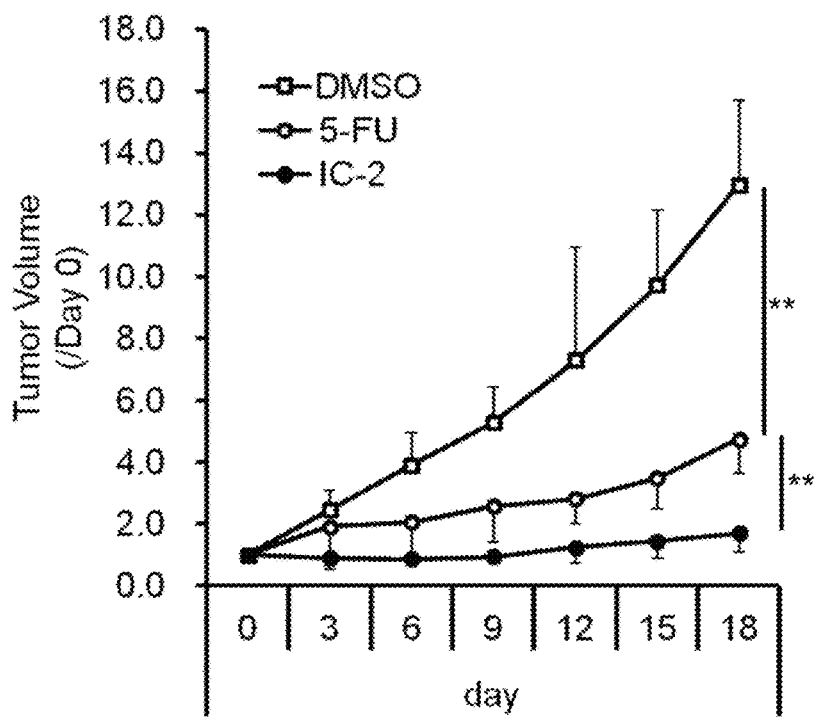

The results demonstrated no change in the body weight when either IC-2 or 5-FU was dosed (FIG. 45). This means that it is possible to safely administer any of IC-2 and 5-FU. Further, IC-2 exhibited a more remarkable anti-malignant tumor therapeutic effect than 5-FU (FIG. 46).

<Example 7> Anti-Tumor Effect on Squamous Cell Carcinoma

HSC2 cells (squamous cell carcinoma cells) were seeded at 2.5×10$^3$ cells/well of a 96-well plate (TPP Techno Plastic Products AG, Trasadingen, Switzerland). After 24 h, IC-2 was added at concentrations indicated in FIG. 47. Next, 0, 24, 72, and 96 h after that, 100 µL of 10% Cell Counting Kit-8 (DOJINDO LABORATORIES, Kumamoto) was added. The mixture was incubated at 37° C. and its absorbance (at a measurement wavelength of 450 nm/control wavelength of 600 nm) was measured by using a Sunrise Rainbow RC (Tecan Group Ltd., Mannedorf, Switzerland).

The results demonstrated that IC-2 exhibited a growth inhibitory effect on squamous cell carcinoma cells (FIG. 47).

In addition, HSC2 cells were seeded at 5×10$^5$ cells/10-cm cell culture dish (TPP). After 24 h, the cells were treated with 0.5 µM of 5-FU or 25 µM of IC-2. Also prepared were cells without low-molecular-weight compound treatment (0 µM). After additional 48 h, the respective cells were harvested. As a primary antibody, used was a mouse anti-human CD44 antibody (Abcam Ltd., Cambridge, UK). Then, Alexa Fluor 488-labeled goat anti-mouse IgG (H+L) (Life Technologies Corp., Carlsbad, Calif.) was used. After that, a cell sorter BD bioscience FACS Aria (Becton, Dickinson and Company, Franklin Lakes, N.J.) was used for analysis. Note that the concentration of each low-molecular-weight compound was determined on the basis of the IC50 concentration at 48 h in a WST assay.

The results demonstrated that while the percentage of CD44-expressing cells was 83.9% in the case without low-molecular-weight treatment, the percentage was reduced to 71.4% in the case of IC-2 treatment. That is, IC-2 exhibited an inhibitory effect on cancer stem cells. In contrast, the percentage was 83.3% in the case of 5-FU treatment, indicating no change observed.

<Example 8> Anti-Tumor Effect on Colon Cancer

DLD-1 cells (colon cancer cells) were cultured on 10-cm cell culture dishes (TPP Techno Plastic Products AG, Trasadingen, Switzerland) by using DMEM under conditions at 5% $CO_2$, 37° C., and 100% humidity. For passage, 70 to 90% confluent cells were washed with PBS(−), and 300 µL of 0.25% Trypsin/1 mM EDTA per 2 mL of PBS(−) was added thereto. The cells were incubated at 37° C. for 5 min and were then detached. After that, 5 mL of DMEM was used to collect the cells. The cells collected were centrifuged at 1000 rpm for 3 min to remove a supernatant. The cells were then suspended in DMEM and were split at a 1:4 ratio.

DLD-1 cells were seeded at 5×10$^5$ cells/well of a 96-well plate (TPP). After 24 h, the cells were treated with 0, 10, or 50 µM of IC-2. Next, 48 h after the treatment, 100 µL of 10% Cell Counting Kit-8 (DOJINDO LABORATORIES, Kumamoto) was added. The mixture was incubated at 37° C. and its absorbance (at a measurement wavelength of 450 nm/control wavelength of 600 nm) was measured by using a Sunrise Rainbow RC (Tecan Group Ltd., Mannedorf, Switzerland).

Figure 48:
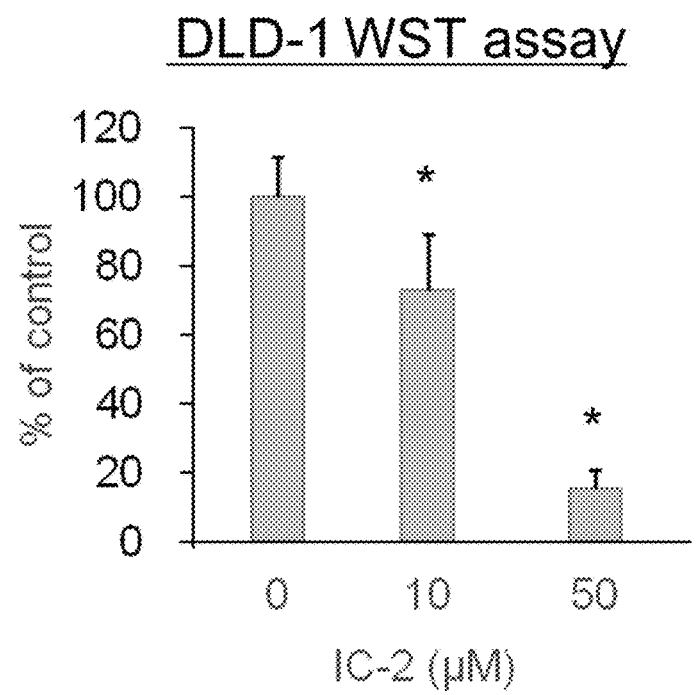

The results demonstrated that IC-2 elicited a growth inhibitory effect on colon cancer cells (FIG. 48).

In addition, DLD-1 cells were seeded at 1×10$^6$ cells/10-cm cell culture dish. After 24 h, the cells were treated with 0.5 or 5 µM of 5-FU or 50 µM of IC-2. At additional 48 h, the cells were harvested. As a primary antibody, used was a mouse anti-human CD44 antibody (Abcam Ltd., Cambridge, UK). Then, Alexa Fluor 488-labeled goat anti-mouse IgG (H+L) (Life Technologies Corp., Carlsbad, Calif.) was used. After that, a MoFlo XDP (Beckman Coulter Inc., Fullerton, Calif.) was used for analysis.

Figure 49:
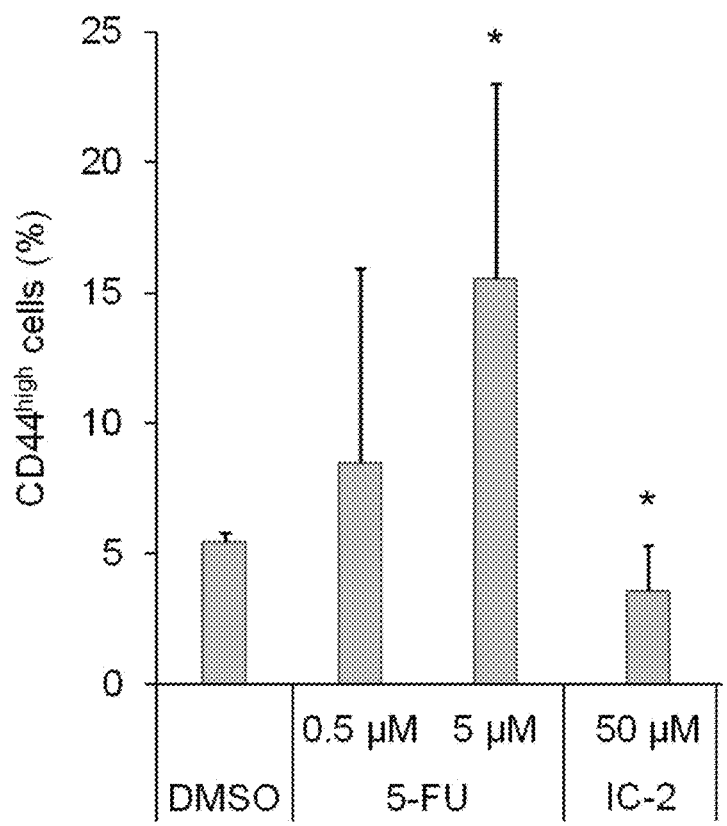
FIG. 49 is a graph showing the results of examining an inhibitory effect of each low-molecular-weight compound on cancer stem cells.

The results demonstrated that IC-2 treatment significantly reduced the percentage of CD44$^{high}$ cells (cells strongly expressing CD44) when compared with control (FIG. 49). That is, IC-2 exerted an inhibitory effect on cancer stem cells. In contrast, 5-FU treatment rather increased the percentage.

<Example 9> Liver Disease Model Mouse Used to Evaluate Inhibitory Effect on Fibrosis

9.1. Evaluation Method

9.1.1. Liver Resection

To induce anesthesia, 1-mL disposable syringe with a 27-G needle was used to intraperitoneally inject, into a mouse, 1 µL/g body weight of a systemic anesthetic somnopentyl (Kyoritsuseiyaku Corporation, Tokyo). After the anesthesia induction, a 1-mL syringe with a 27-G needle was used to collect whole blood from inferior vena cava and the whole liver was then removed.

9.1.2. Sirius Red Staining

The liver tissue sample, as so resected, was fixed in 4% paraformaldehyde (Nacalai tesque, Kyoto) at room temperature for 16 h, embedded in paraffin, and sectioned with a microtome to prepare tissue sections, which were then stained by using a Picosirius Red Stain Kit (Polysciences Inc., Warrington, Pa.) in accordance with the attached protocol. After that, a BZ-9000 (KEYENCE CORPORATION, Osaka) was used to take 10 photographs of light-field enlarged images (100×) per tissue sample. The ratio of the red-stained fiber area to the total tissue area of each photographed image was quantified to calculate a fibrosis-positive area ratio.

9.1.3. Azan Staining

The liver tissue sample, as so resected, was fixed in 4% paraformaldehyde at room temperature for 16 h, embedded in paraffin, and sectioned with a microtome to prepare tissue sections. The tissue sections were subjected to deparaffinization using xylene (Nacalai tesque) and a hydration reaction with ethanol (Nacalai tesque), and were then allowed to stand in 5% potassium dichromate/trichloroacetic acid aqueous solution (Wako Pure Chemical Industries, Ltd.) for 20 min. After washing in running water for 5 min, the tissue sections were stained with Azocarmine G (Wako Pure Chemical Industries, Ltd.) at 60° C. for 1 h, washed with water, and then destained for 3 min in 5% aniline (Nacalai tesque)-containing ethanol solution. Next, 5% acetic acid (Nacalai tesque)-containing ethanol solution was used to stop the destaining reaction. After washing with water, the tissue sections were allowed to stand in 5% phosphotungstic acid aqueous solution (Alfa Aesar, Ward Hill, Mass.) for 1 h. After washing with water, the tissue sections were stained for 30 min in 1% Orange G/0.25% Aniline Blue (Wako Pure Chemical Industries, Ltd.)/4% acetic acid aqueous solution. Then, the tissue sections were destained in ethanol until red color and blue color became distinguishable. After the solution had been replaced by xylene, each tissue section was covered with a caver glass and sealed. Subsequently, a BZ-9000 was used to take 10 photographs of light-field enlarged images (100×) of the stained sections prepared per tissue sample. The ratio of the blue-stained fiber area to the total tissue area of each photographed image was quantified to calculate a fibrosis-positive area ratio.

9.2. Carbon Tetrachloride-Induced Fibrosis Model Mouse Used to Evaluate Anti-Fibrosis Therapeutic Effect

9.2.1. Animal Experiments and Rearing Conditions

Seven-week-old C57BL/6 male mice (Japan SLC, Inc., Shizuoka) were subjected to 1-week preparatory rearing and healthy ones were then used. The mice were housed in animal cages at a room temperature of 22±1° C. and a humidity of 50±5% throughout the preparatory rearing and experimental period and were given ad libitum access to food and water.

9.2.2. Carbon Tetrachloride Administration Protocol and Drug Dosing Protocol A microsyringe (ITO CORPORATION, Shizuoka) was used to intraperitoneally administer 0.2 ml/kg of carbon tetrachloride ($CCl_4$; Wako Pure Chemical Industries, Ltd.) 3 times a week for 4, 6, or 8 weeks. Carbon tetrachloride was dissolved in corn oil (Wako Pure Chemical Industries, Ltd.) to prepare 10% solution for usage. This carbon tetrachloride solution was administered for four weeks. Next, the mice were divided into a total of 4 groups: vehicle dosing group, glycyrrhizin dosing group, ICG-001 dosing group, and IC-2 dosing group. Carbon tetrachloride and each drug solution, as prepared by the process below at the same time, were intraperitoneally dosed 3 times a week for 4 weeks by using a microsyringe. Note that the carbon tetrachloride and the drug solution were alternately dosed with one day interval.

Glycyrrhizin (TOKYO CHEMICAL INDUSTRY CO., LTD., Tokyo) was dissolved in physiological saline to prepare a solution at a concentration of 30 mg/mL while 4 M NAOH liquid was used to adjust the pH to 7.0. IC-2 and ICG-001 (AdooQ BioScience, Irvine, Calif.) were each dissolved in WellSolve (Celeste Corporation, Tokyo) at a concentration of 40 mg/mL and 10 mg/mL, respectively. Each mixture was further heated in a hot water bath at 60° C. for 10 min and was then dissolved completely. A 9-fold volume of physiological saline was added to the WellSolve solution in which each drug had been dissolved. Next, an amount of glycyrrhizin required to prepare a drug solution at 150 mg/kg was weighed, and physiological saline was added thereto to adjust the liquid volume to 200 μL. Then, an amount of IC-2 or ICG-001 required to prepare a drug solution at 10.6 mg/kg or 5 mg/kg, respectively, was weighed, and a solution, in which WellSolve and physiological saline had been mixed at a 1:9 ratio, was added thereto to adjust the liquid volume to 200 μL. In addition, a solution in which WellSolve and physiological saline were mixed at 1:9 was prepared as a vehicle.

9.2.3. Results

FIG. 50 are Sirius Red staining images at 8 weeks after carbon tetrachloride administration and a graph showing the results of quantifying each fibrosis area. Red-stained regions each indicate a fibrosis area. While carbon tetrachloride was administered for 8 weeks, each drug was dosed for the last 4 weeks. Then, the fibrosis area of the IC-2 dosing group was found to decrease more than that of the vehicle group.

9.3. Non-Alcoholic Steatohepatitis Model Mouse Used to Evaluate Anti-Fibrosis Therapeutic Effect

9.3.1. Animal Experiments and Rearing Conditions

Seven-week-old C57BL/6JHamSlc-ob/ob male mice (Charles River Laboratories Japan Inc., Kanagawa) were subjected to preparatory rearing for 1 week. Next, the mice were divided into 2 groups and each group was fed with high fat diet D09100301 or control diet D09100304 (Research Diets Inc., New Brunswick, N.J.). The mice were housed in animal cages at a room temperature of 22±1° C. and a humidity of 50±5% throughout the preparatory rearing and experimental period and were given ad libitum access to food and water.

9.3.2. Non-Alcoholic Steatohepatitis-Inducing Protocol and Drug Dosing Method First, high fat diet was fed for six weeks. Next, the mice were divided into a total of 4 groups: vehicle dosing group, sodium ursodeoxycholate dosing group, ICG-001 dosing group, and IC-2 dosing group. Then, the vehicle, ICG-001, and IC-2 drug solutions, as prepared by the process below, were each intraperitoneally dosed 3 times a week for 3 or 6 weeks by using a microsyringe. In addition, a single daily dose of sodium ursodeoxycholate was orally administered by using a 1-mL disposable syringe with a conductor.

Sodium ursodeoxycholate (Mitsubishi Tanabe Pharma Corporation, Osaka) was dissolved in a 1 M NaOH aqueous solution; and the pH was adjusted with aqueous HCl to 8.3 to prepare a solution at a concentration of 60 mg/mL. IC-2 or ICG-001 was dissolved in WellSolve at a concentration of 40 mg/mL or 10 mg/mL, respectively. Each mixture was further heated in a hot water bath at 60° C. for 10 min and was then dissolved completely. A 4-fold volume of physiological saline was added to the WellSolve solution in which each drug had been dissolved. Next, an amount of sodium ursodeoxycholate required to prepare a drug solution at 150 mg/kg was weighed, and sterilized water was added thereto to adjust the liquid volume to 200 μL. Then, an amount of IC-2 or ICG-001 required to prepare a drug solution at 21.2 mg/kg or 5 mg/kg, respectively, was weighed, and a solution, in which WellSolve and physiological saline had been mixed at a 1:9 ratio, was added thereto to adjust the liquid volume to 200 pt. As a vehicle, prepared was a solution in which WellSolve and physiological saline had been mixed at a 1:9 ratio.

9.3.3. Results

Figure 51:
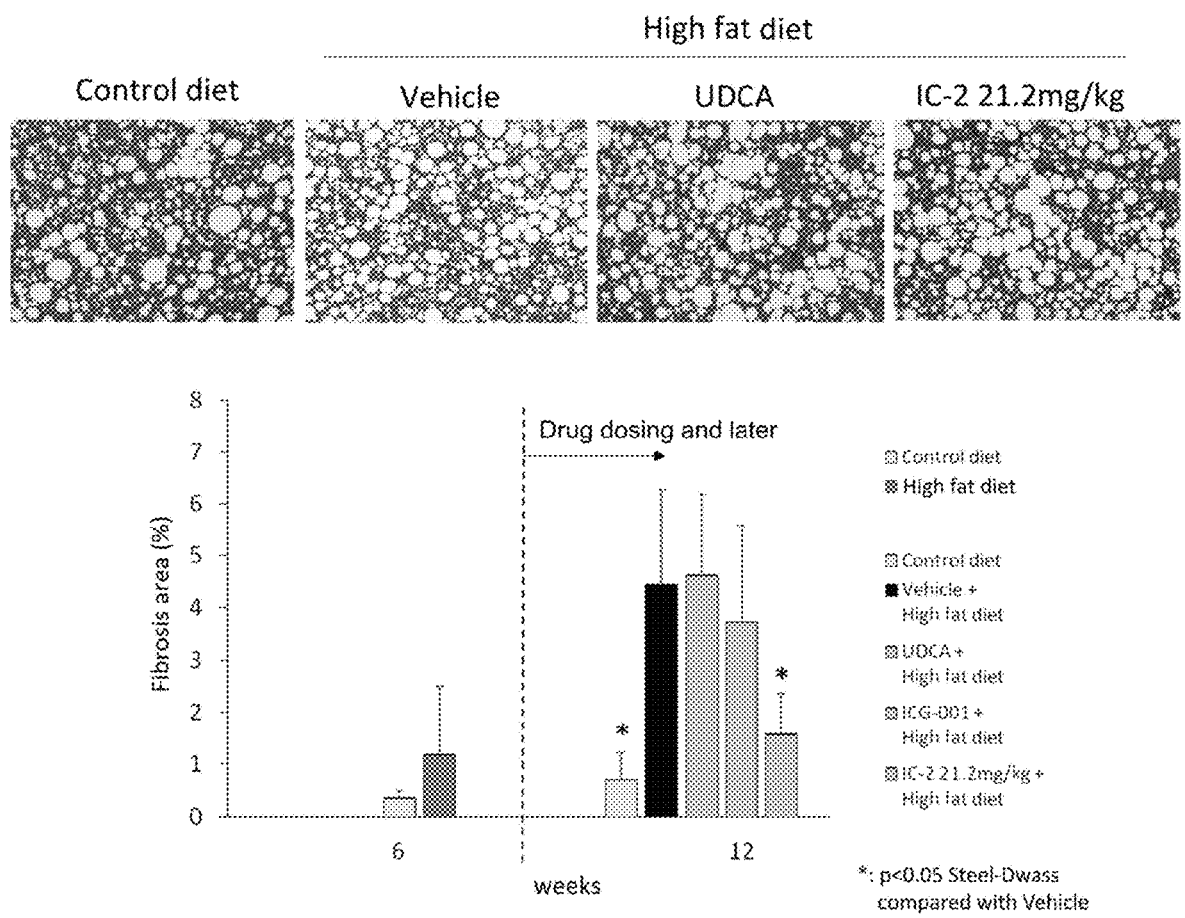

FIG. 51 are Azan staining images after high fat diet was fed for 12 weeks and a graph showing the results of quantifying each fibrosis area. Blue-stained regions each indicate a fibrosis area. While high fat diet was fed for 12 weeks, each drug was dosed for the last 6 weeks. Then, the fibrosis area of the IC-2 dosing group was found to decrease more than that of the vehicle group.

<Example 10> Effect of Combination of HC-1 and 5-FU

HC-1 (hexachlorophene methyl ether bis(2,3,5-trichloro-6-methoxyphenyl)methane) was synthesized by the process described in WO2012/141038. HSC2 cells were seeded at $2.5 \times 10^3$ cells/well of a 96-well plate (TPP Techno Plastic Products AG, Trasadingen, Switzerland). After 24 h, the cells were treated with HC-1 or 5-FU at different concentrations and for periods indicated in FIG. 52. Next, 100 μL of 10% Cell Counting Kit-8 (DOJINDO LABORATORIES, Kumamoto) was added. The mixture was incubated at 37° C. and its absorbance (at a measurement wavelength of 450 nm/control wavelength of 600 nm) was measured by using a Sunrise Rainbow RC (Tecan Group Ltd., Mannedorf, Switzerland). FIG. 52 shows the results.

HSC2 cells were seeded at $2.5 \times 10^3$ cells/well of a 96-well plate. After 24 h, the cells were treated for 48 h with 50 μM HC-1 and 5-FU at different concentrations indicated in FIG. 53. Next, 100 μL of 10% Cell Counting Kit-8 was added. The mixture was incubated at 37° C. and its absorbance (at a measurement wavelength of 450 nm/control wavelength of 600 nm) was measured by using a Sunrise Rainbow RC.

Figure 53:
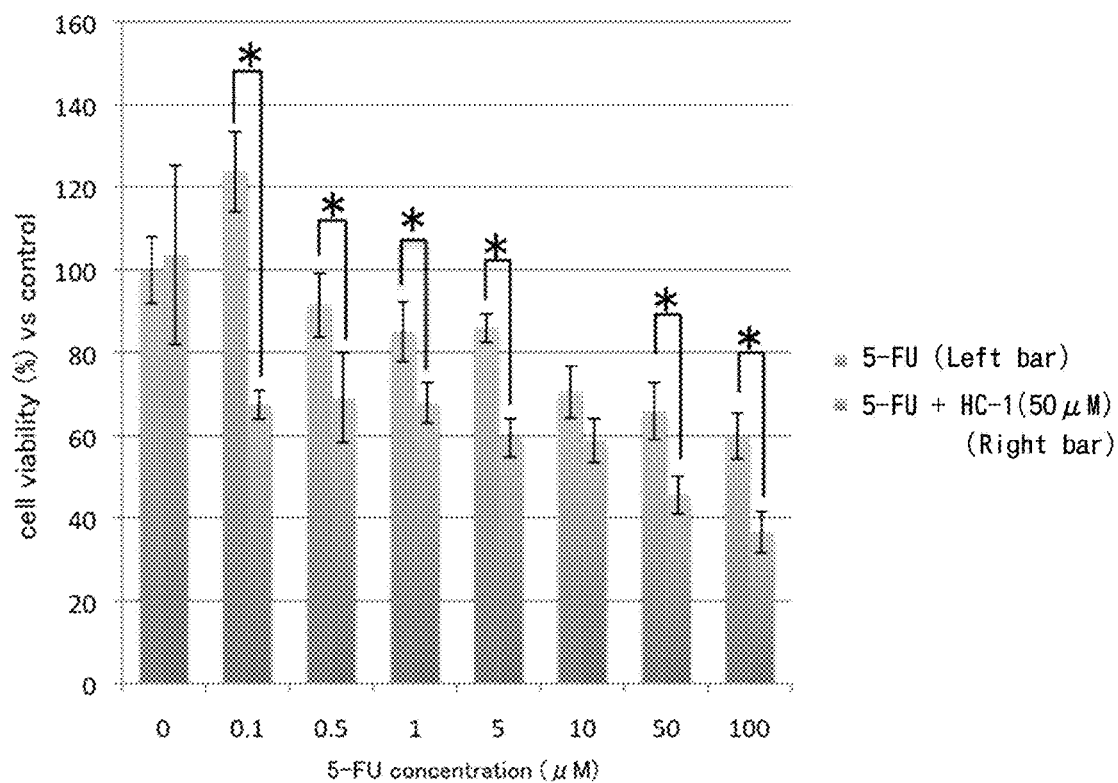
FIGS. 53 to 55 are graphs and photographs showing the results of examining an anti-tumor effect when HC-1 was combined with 5-FU.

FIG. 53 shows the results. The combination of HC-1 and 5-FU exerted a synergistic anti-tumor effect.

HSC2 cells were seeded at $1 \times 10^5$ cells/well of a 6-well plate (TPP). After 24 h, the cells were treated for 48 h with 5-FU, HC-1, or 5-FU and HC-1 at concentrations indicated in FIG. 54. Next, the cells were treated with an Annexin-V-FLUOS Staining Kit (Roche Diagnostics GmbH, Mannheim, Germany). Then, the Annexin-V- and PI-stained cells were observed under an IX71 (Olympus Corporation, Tokyo). After that, 10 fields per staining were analyzed by image analysis software inForm 2.0.4 (PerkinElmer, Waltham, Mass.) to calculate the percentage of apoptotic cells and the percentage of dead cells.

Figure 54:
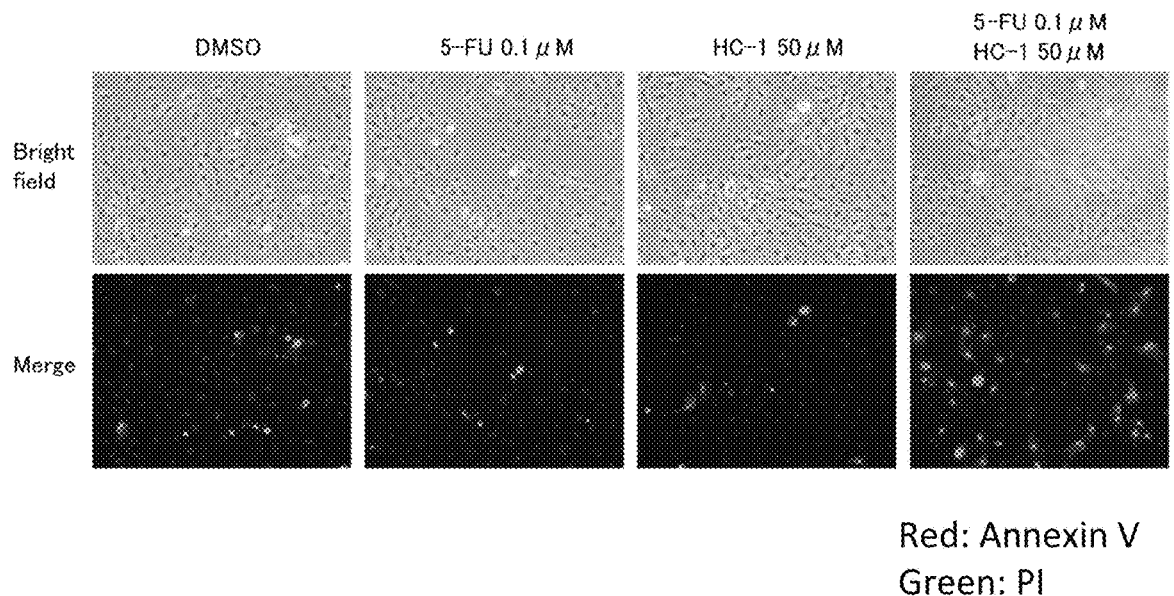
Figure 55:
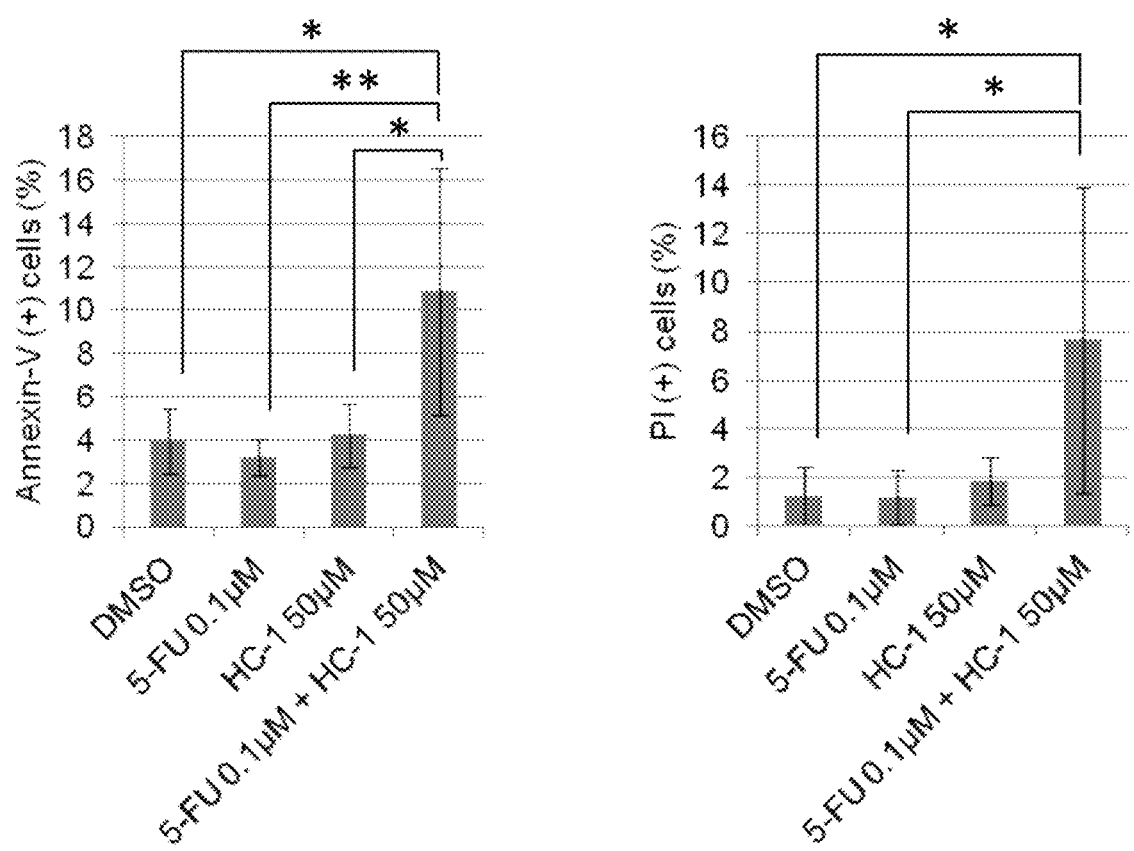

FIGS. 54 to 55 show the results. The combination of HC-1 and 5-FU induced cell death.

<Discussion>

The above demonstrated that use of each novel compound suppressed the growth of cancer cells. In addition, each novel compound exerted a growth inhibitory effect on cancer stem cells. Further, each novel compound exerted an inhibitory effect on fibrosis, which may cause development of cancer. Furthermore, each novel compound exerted an effect of inducing differentiation from a mesenchymal stem cell into hepatocytes. Moreover, the combination of HC-1 and 5-FU elicited a synergistic anti-tumor effect.

Hereinabove, the present invention has been described based on the Examples. These Examples are absolutely examples. It should be understood by those skilled in the art that various modifications are allowed, and those modifications are also within the scope of the present invention.

The invention claimed is:
1. A compound, a salt thereof, or a solvate thereof, the compound represented by formula (1):

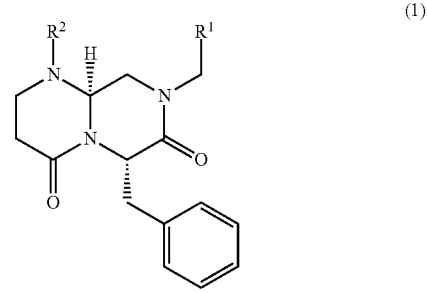

wherein substituents $R^1$ and $R^2$ are represented by the following case (a) or (b):
(a) $R^1$ is optionally substituted phenyl, and
$R^2$ is H, optionally substituted phenyl, or —C(O)NHR$^3$ where the $R^3$ is H, $C_{1-6}$ alkyl, or optionally substituted benzyl; or
(b) $R^1$ is optionally substituted naphthyl or optionally substituted phenyl, and
$R^2$ is optionally substituted phenyl or —C(O)NHR$^4$ where the $R^4$ is H, $C_{1-6}$ alkyl, or optionally substituted siloxybenzyl, and
wherein the term "optionally substituted" means that the respective group is unsubstituted or has a substituent selected from H, halogen, nitro, amino, cyano, OH, $C_{1-6}$ alkyl, $C_{1-6}$ halogenoalkyl, $C_{1-6}$ hydroxyalkyl, $C_{1-6}$ alkylamino, $C_{3-6}$ cycloalkyl, $C_{2-6}$ alkenyl, $C_{2-6}$ halogenoalkenyl, $C_{2-6}$ hydroxyalkenyl, $C_{2-6}$ alkenylamino, $C_{3-6}$ cycloalkenyl, $C_{2-6}$ alkynyl, $C_{2-6}$ halogenoalkynyl, $C_{2-6}$ hydroxyalkynyl, $C_{2-6}$ alkynylamino, $C_{1-6}$ alkoxy, $C_{1-6}$ halogenoalkoxy, $C_{1-6}$ hydroxyalkoxy, $C_{1-6}$ alkoxyamino, $C_{1-6}$ alkoxyphenyl, trialkylsiloxy, alkyldiphenylsiloxy, aryl, heteroaryl, $C_{1-6}$ alkoxy-substituted $C_{1-6}$ alkoxy, $C_{1-6}$ alkoxyphenyl-substituted $C_{1-6}$ alkoxy, tri($C_{1-6}$ alkylsiloxy)$C_{1-6}$ alkyl, $C_{1-6}$ alkyldiphenylsiloxy $C_{1-6}$ alkyl, triphenylsiloxy $C_{1-6}$ alkyl, tri($C_{1-6}$ alkyl)siloxy, $C_{1-6}$ alkyldiphenylsiloxy, and triphenylsiloxy, and
the solvate is water, ethanol, or acetic acid.
2. The compound, the salt thereof, or the solvate thereof according to claim 1, wherein
the $R^1$ of case (a) is phenyl having a substituent $R^5$ where the $R^5$ is at least one substituent selected from the group consisting of H, halogen, nitro, amino, cyano, OH, $C_{1-6}$ alkyl, $C_{1-6}$ halogenoalkyl, $C_{1-6}$ hydroxyalkyl, $C_{1-6}$ alkylamino, $C_{1-6}$ alkoxy, $C_{1-6}$ halogenoalkoxy, $C_{1-6}$ hydroxyalkoxy, and $C_{1-6}$ alkoxyamino;

the $R^2$ of case (a) is H, phenyl having a substituent $R^5$, —C(O)NHR$^3$ where the $R^3$ is benzyl having a substituent $R^6$ where the $R^6$ is at least one substituent selected from the group consisting of H, halogen, nitro, amino, cyano, OH, $C_{1-6}$ alkyl, $C_{1-6}$ halogenoalkyl, $C_{1-6}$ hydroxyalkyl, $C_{1-6}$ alkylamino, $C_{1-6}$ alkoxy, $C_{1-6}$ halogenoalkoxy, $C_{1-6}$ hydroxyalkoxy, $C_{1-6}$ alkoxyamino, $C_{1-6}$ alkoxy-substituted $C_{1-6}$ alkoxy, $C_{1-6}$ alkoxyphenyl-substituted $C_{1-6}$ alkoxy, tri($C_{1-6}$ alkylsiloxy)$C_{1-6}$ alkyl, $C_{1-6}$ alkyldiphenylsiloxy $C_{1-6}$ alkyl, triphenylsiloxy $C_{1-6}$ alkyl, tri($C_{1-6}$ alkyl)siloxy, $C_{1-6}$ alkyldiphenylsiloxy, and triphenylsiloxy;

the $R^1$ of case (b) is phenyl having a substituent $R^5$ or naphthyl; and the $R^2$ of case (b) is phenyl having a substituent $R^5$ or —C(O)NHR$^4$ where the $R^4$ is H, $C_{1-6}$ alkyl, or siloxybenzyl having a substituent $R^5$.

3. The compound, the salt thereof, or the solvate thereof according to claim 2, wherein the $R^2$ of case (a) is —C(O)NH(CH$_2$C$_6$H$_5$);

the $R^1$ of case (b) is naphthyl; and the $R^2$ of case (b) is nitrophenyl or —C(O)NHR$^4$ where the $R^4$ is H or siloxybenzyl having a substituent $R^5$.

4. The compound, the salt thereof, or the solvate thereof according to claim 1, wherein the $R^1$ of case (a) is phenyl having at least one substituent selected from the group consisting of F, Cl, nitro, OH, and methoxy;

the $R^2$ of case (a) is —C(O)NH(CH$_2$C$_6$H$_5$);

the $R^1$ of case (b) is naphthyl; and the $R^2$ of case (b) is —C(O)NH$_2$, nitrophenyl, or (tert-butyldimethylsiloxy)benzyl.

* * * * *